US010479999B2

(12) United States Patent
Kerfeld et al.

(10) Patent No.: US 10,479,999 B2
(45) Date of Patent: Nov. 19, 2019

(54) ENGINEERED SHELL PROTEINS FOR MICROCOMPARTMENT SHELL ELECTRON TRANSFER AND CATALYSIS

(71) Applicant: Board of Trustees of Michigan State University, East Lansing, MI (US)

(72) Inventors: Cheryl A. Kerfeld, Okemos, MI (US); Clement Aussignargues, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 124 days.

(21) Appl. No.: 15/851,382

(22) Filed: Dec. 21, 2017

(65) Prior Publication Data

US 2018/0216117 A1     Aug. 2, 2018

Related U.S. Application Data

(60) Provisional application No. 62/438,655, filed on Dec. 23, 2016.

(51) Int. Cl.
| | |
|---|---|
| *C12N 15/52* | (2006.01) |
| *C12N 15/113* | (2010.01) |
| *C12N 15/74* | (2006.01) |
| *C12N 15/67* | (2006.01) |
| *C12N 15/65* | (2006.01) |
| *C07K 14/195* | (2006.01) |

(52) U.S. Cl.
CPC ............ *C12N 15/52* (2013.01); *C07K 14/195* (2013.01); *C12N 15/113* (2013.01); *C12N 15/65* (2013.01); *C12N 15/67* (2013.01); *C12N 15/74* (2013.01); *C07K 2319/01* (2013.01); *C07K 2319/735* (2013.01)

(58) Field of Classification Search
None
See application file for complete search history.

(56) References Cited

U.S. PATENT DOCUMENTS

| | | | |
|---|---|---|---|
| 9,187,766 | B2 | 11/2015 | Prentice et al. |
| 2012/0210459 | A1 | 8/2012 | Kerfeld et al. |
| 2013/0133102 | A1 | 5/2013 | Kerfeld et al. |
| 2015/0026840 | A1 | 1/2015 | Kerfeld et al. |

OTHER PUBLICATIONS

Adams, Paul D., et al., "Phenix: a comprehensive Python-based system for macromolecular structure solution", Acta Crystallogr. D Biol. Crystallogr., 66(Part 2), (.2010), 213-221.
Antonkine, Mikhail L., et al., "Synthesis and characterization of de novo designed peptides modelling the binding sites of [4Fe—4S] clusters in photosystem I", Biochim. Biophys. Acta (BBA)-Bioenergetics, 1787(8), (2009), 995-1008.

Aussignargues, Clément, et al., "Structure and Function of a Bacterial Microcompartment Shell Protein Engineered to Bind a [4Fe—4S] Cluster", J. Am. Chem. Soc., 138, (2016), 5262-5270.
Axen, Seth D., et al., "A Taxonomy of Bacterial Microcompartment Loci Constructed by a Novel Scoring Method", PLOS Comput. Biol. 10(10), e1003898., (Oct. 2014), 1-20.
Beinert, Helmut, et al., "Iron-Sulfur Clusters: Nature's Modular, Multipurpose Structures", Science, 277(5326), (1997), 653-659.
Bobik, T. A., et al., "Bacterial microcompartments: widespread prokaryotic organelles for isolation and optimization of metabolic pathways", Mol. Microbiol., 98(2), (2015), 193-207.
Broderick, Joan B., et al., "Radical S-Adenosylmethionine Enzymes", Chem. Rev., 114(8), (2014), 4229-4317.
Capozzi, Francesco, et al., "Coordination Sphere Versus Protein Environment as Determinates of Electronic and Functional Properties of Iron-Sulfur Proteins", In: Metal Sites in Proteins and Models Redox Centres—Structure and Bonding, vol. 90, Hill, H. A., et al., Eds., Springer Berlin, Heidelberg, (1998), 127-160.
Cleland, W. W., et al., "Dithiothreitol, a New Protective Reagent for SH Groups", Biochemistry, 3(4), (1964), 480-482.
Coldren, Christopher D., et al., "The rational design and construction of a cuboidal iron-sulfur-protein", Proc. Natl. Acad. Sci. USA, 94(13), (1997), 6635-6640.
Dutton, P. Leslie, et al., "[23] Redox potentiometry: determination of midpoint potentials of oxidation-reduction components of biological electron-transfer systems", Methods Enzymol. , 54, (1978), 411-435.
Emsley, Paul, et al., "Coot: model-building tools for molecular graphics", Acta Crystallogr. D Biol. Crystallogr. 60, (2004), 2126-2132.
Erikson, Brent, et al., "Perspective on opportunities in industrial biotechnology in renewable chemicals", Biotechnology J , 7(2), (2012), 176-185.
Fan, Chenguang, et al., "Short N-terminal sequences package proteins into bacterial microcompartments", Proc. Natl. Acad. Sci. USA, 107(16), (2010), 7509-7514.
Fontecave, Marc, et al., "Iron-sulfur clusters: ever-expanding roles", Nat. Chem. Biol., 2, (2006), 171-174.
Frank, Stefanie, et al., "Bacterial microcompartments moving into a synthetic biological world", J. Biotechnol., 163(2), (2013), 273-279.
Giastas, Petros, et al., "The structure of the 2[4Fe—4S] ferredoxin from Pseudomonas aeruginosa at 1.32-Å resolution: comparison with other high-resolution structures of ferredoxins and contributing structural features to reduction potential values", J. Biol. Inorg. Chem., 11(4), (2006), 445-458.
Gibney, Brian R., et al., "Ferredoxin and ferredoxin-heme maquettes", Proc. Natl. Acad. Sci. USA. , 93, (1996), 15041-15046.

(Continued)

*Primary Examiner* — Robert A Zeman
(74) *Attorney, Agent, or Firm* — Schwegman Lundberg & Woessner, P.A.

(57) ABSTRACT

Described herein are bacterial microcompartments shell proteins modified to stably incorporate iron-sulfur clusters. Such bacterial microcompartments shell proteins exhibit redox cycling and confer electron transfer functionality to bacterial microcompartment shells.

11 Claims, 24 Drawing Sheets
(22 of 24 Drawing Sheet(s) Filed in Color)
Specification includes a Sequence Listing.

(56) References Cited

OTHER PUBLICATIONS

Grzyb, Joanna, et al., "De novo design of a non-natural fold for an iron-sulfur protein: Alpha-helical coiled-coil with a four-iron four-sulfur cluster binding site in its central core", Biochim. Biophys. Acta (BBA)—Bioeneretics, 1797(3), (2010), 406-413.

Guigliarelli, Bruno, et al., "Application of EPR Spectroscopy to the Structural and Functional Study of Iron-Sulfur Proteins", Adv. Inorg. Chem., vol. 47, (1999), 421-497.

Herskovitz, T., et al., "Structure and Properties of a Synthetic Analogue of Bacterial Iron-Sulfur Proteins", Proc. Natl. Acad. Sci. USA. , 69(9), (1972), 2437-2441.

Hoppe, Alessandra, et al., "[$Fe_4S_4$]-and [$Fe_3S_4$]-cluster formation in synthetic peptides", Biochim. Biophys. Acta, 1807(11), (2011), 1414-1422.

Huseby, Douglas L., et al., "Evidence that a Metabolic Microcompartment Contains and Recycles Private Cofactor Pools", J Bacteriol., 195(12), (2013), 2864-2879.

Imlay, James A., "Iron-sulphur clusters and the problem with oxygen", Mol. Microbiol., 59(4), (2006), 1073-1082.

Johnson, Mickael K., et al., "Iron-Sulfer Proteins", In: Encyclopedia of Inorganic and Bioinorganic Chemistry, Online (c) 2011 John Wiley & Sons, Ltd., (2011), 1-31.

Kabsch, Wolfgang, et al., "XDS", Acta Crystallogr. D Biol. Crystallogr., 66, (2010), 125-132.

Kerfeld, Cheryl A., et al., "Bacterial microcompartments and the modular construction of microbial metabolism", Trends Microbiol., 23, (2015), 22-34.

Kerfeld, Cheryl A., et al., "Protein Structures Forming the Shell of Primitive Bacterial Organelles", Science, 309(5736), (2005), 936-938.

Kinney, James N., et al., "Comparative analysis of carbonoxysome shell proteins", Photosynth. Res., 109(1-3), (2011), 21-32.

Klein, Michael G., et al., "Identification and Structural Analysis of a Novel Carboxysome Shell Protein with Implications for Metabolite Transport", J. Mol. Biol, 392(2), (2009), 319-333.

Kuchenreuther, Jon M., et al., "High-Yield Expression of Heterologous [FeFe] Hydrogenases in *Escherichia coli*", PloS One , 5(11), e15491, (2010), 1-7.

Lanz, N. D., et al., "Chapter 7-RlmN and AtsB as Models for the Overproduction and Characterization of Radical SAM Proteins", Methods Enzymol., 516, (2012), 125-152.

Lassila, Jonathan K., et al., "Assembly of Robust Bacterial Microcompartment Shells Using Building Blocks from an Organelle of Unknown Function", J. Mol. Biol.,426(11), (2014), 2217-2228.

Lawrence, Andrew D., et al., "Solution Structure of a Bacterial Microcompartment Targeting Peptide and Its Application in the Construction of an Ethanol Bioreactor", ACS Synthetic Biology, 3(7), (2014), 454-465.

Mayhew, Stephen G., et al., "The Redox Potential of Dithionite and $So_{-2}$ from Equilibrium Reactions with Flavodoxins, Methyl Viologen and Hydrogen plus Hydrogenase", Eur J. Biochem, 85, (1978), 535-547.

Mccoy, Airlie J., et al., "Phaser crystallographic software", J. Appl. Crystallogr., 40, (2007), 658-674.

Mitra, Devrani, et al., "Characterization of [4Fe—4S] Cluster Vibrations and Structure in Nitrogenase Fe Protein at Three Oxidation Levels via Combined NRVS, EXAFS, and DFT Analyses", J. Am. Chem. Soc., 135(7), (2013), 2530-2543.

Moura, José J. G., et al., "[12] Ferredoxins", Methods Enzymol., 243, (1994), 165-188.

Nanda, Vikas, et al., "De Novo Design of a Redox-Active Minimal Rubredoxin Mimic", J. Am. Chem. Soc., 127(16), (2005), 5804-5805.

Pang, Allan, et al., "Structure of PduT, a trimeric bacterial microcompartment protein with a 4Fe—4S cluster-binding site", Acta Crystallogr. D Biol. Crystallogr., 67(2), (2011), 91-96.

Parsons, J. B., et al., "Characterisation of PduS, the pdu Metabolosome Corrin Reductase, and Evidence of Substructural Organisation within the Bacterial Microcompartment", PloS One, 5(11), e14009, (2010), 1-8.

Parsons, Joshua B., et al., "Biochemical and Structural Insights into Bacterial Organelle Form and Biogenesis", j. Biol. Chem., 283, (2008), 14366-14375.

Petros, Amy K, et al., "Femtomolar Zn(II) Affinity in a Peptide-Based Ligand Designed To Model Thiolate-Rich Metalloprotein Active Sites", Inorg. Chem., 45(25), (2006), 9941-9958.

Robbins, A. H., et al., "Structure of activated aconitase: formation of the [4Fe—4S] cluster in the crystal", Proc. Natl. Acad. Sci. USA., 86(10), (1989), 3639-3643.

Roy, Anindya, et al., "A De Novo Designed 2[4Fe—4S] Ferredoxin Mimic Mediates Electron Transfer", J. Am. Chem. Soc., 136(49), (2014), 17343-17349.

Sagermann, Martin, et al., "Crystal structure of the EutL shell protein of the ethanolamine ammonia lyase microcompartment", Proc. Natl. Acad. Sci. USA, 106(22), (2009), 8883-8867.

Saridakis, E., et al., "Insight into the protein and solvent contributions to the reduction potentials of [4Fe—4S]$^{2+/+}$ clusters: crystal structures of the *Allochromatium vinosum* ferredoxin variants C57A and V13G and the homologous *Escherichia coli* ferredoxin", J. Biol. Inorg. Chem., 14(5), (2009), 783-799.

Stoll, Stefan, et al., "EasySpin, a comprehensive software package for spectral simulation and analysis in EPR", J. Magn. Reson., 178(1), (2006), 42-55.

Stookey, Lawrence L., et al., "Ferrozine—A New Spectrophotometric Reagent for Iron", Anal. Chem. , 42(7), (1970), 779-781.

Sutter, Markus, et al., "Two new high-resolution crystal structures of carboxysome pentamer proteins reveal high structural conservation of CcmL orthologs among distantly related cyanobacterial species", Photosynth. Res., 118(1-2), (2013), 9-16.

Sweeney, William V., et al., "Proteins Containing 4Fe—4S Clusters: An Overview", Annu. Rev. Biochem., 49, (1980), 139-161.

Tanaka, Shiho, et al., "Atomic-Level Models of the Bacterial Carboxysome Shell", Science, 319((5866), (2008), 1083-1086.

Thompson, Michael C., et al., "Identification of a Unique Fe—S Cluster Binding Site in a Glycyl-Radical Type Microcompartment Shell Protein", J. Mol. Biol. , 426(19), (2014), 3287-3304.

Tsai, Sophia J., et al., "Chapter 1—Bacterial Microcompartments: Insights into the Structure, Mechanism, and Engineering Applications", Prog Mol Biol Transl Sci, 103 (Progress in Molecular Biology and Translational Science—Science Direct, (2011), 1-20.

Wheatley, Nicole M., et al., "Bacterial microcompartment shells of diverse functional types possess pentameric vertex proteins.", Protein Sci., 22(5), (2013), 660-665.

Winn, Martyn' D., et al., "Overview of the CCP4 suite and current developments", Acta Crystallogr. D Biol. Crystallogr., 67(Part 4), (2011), 235-242.

Yu, Fangting, et al., "Protein Design: Toward Funcitional Metalloenzymes", Chem. Rev., 114, (2014), 3495-3578.

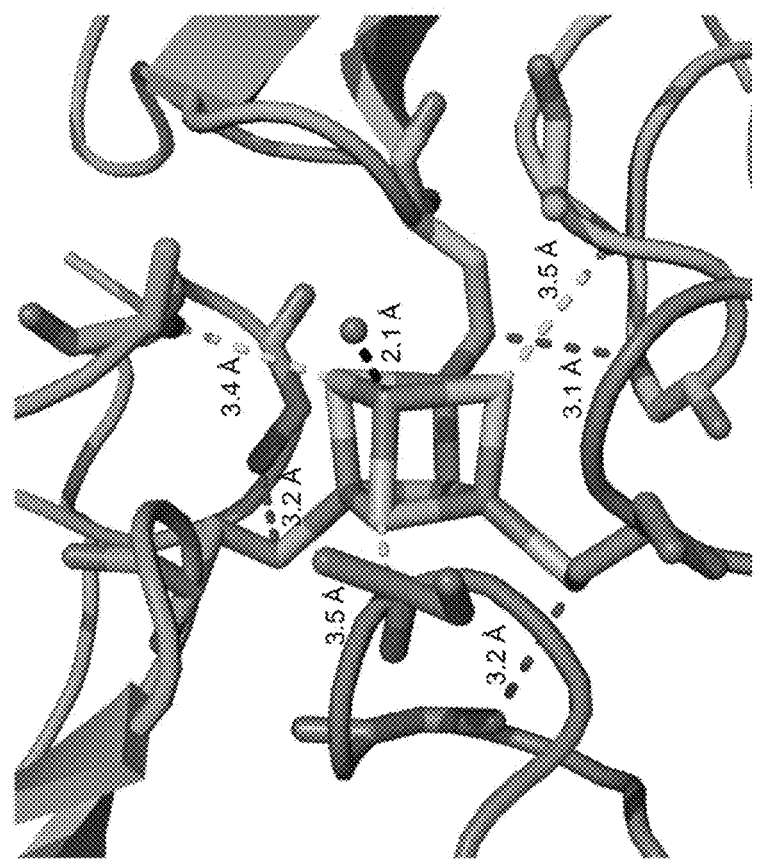
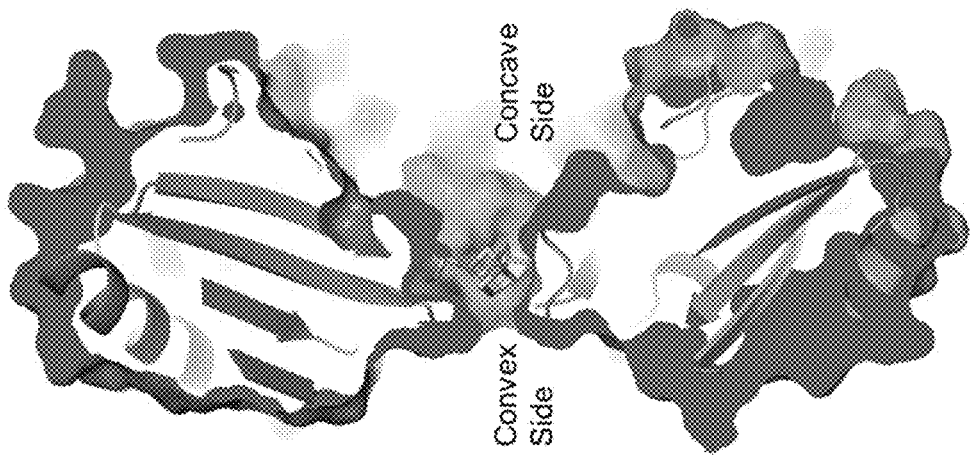
FIG. 3B
FIG. 3A

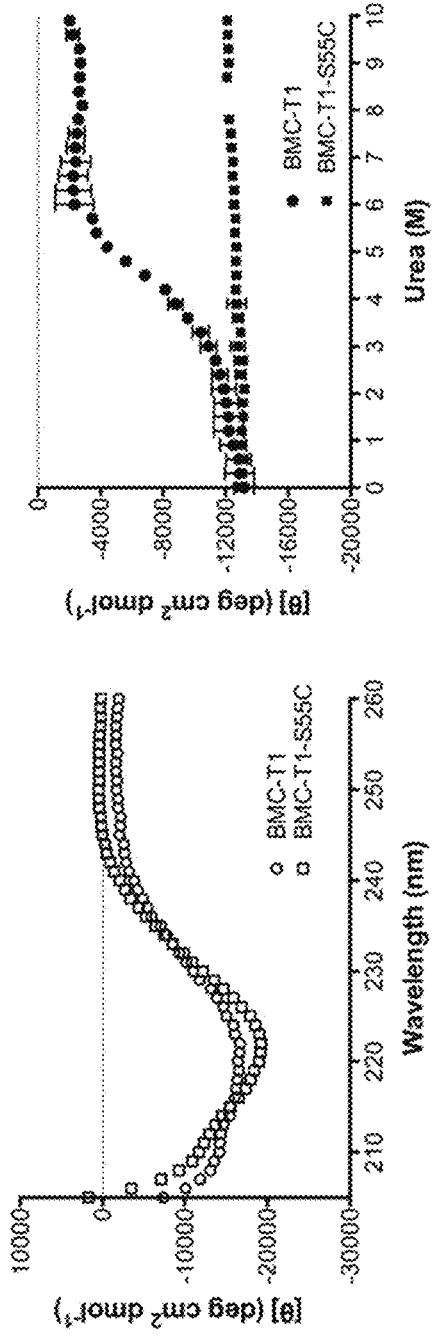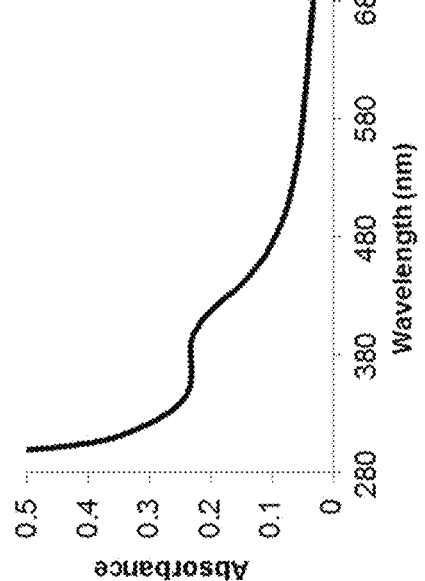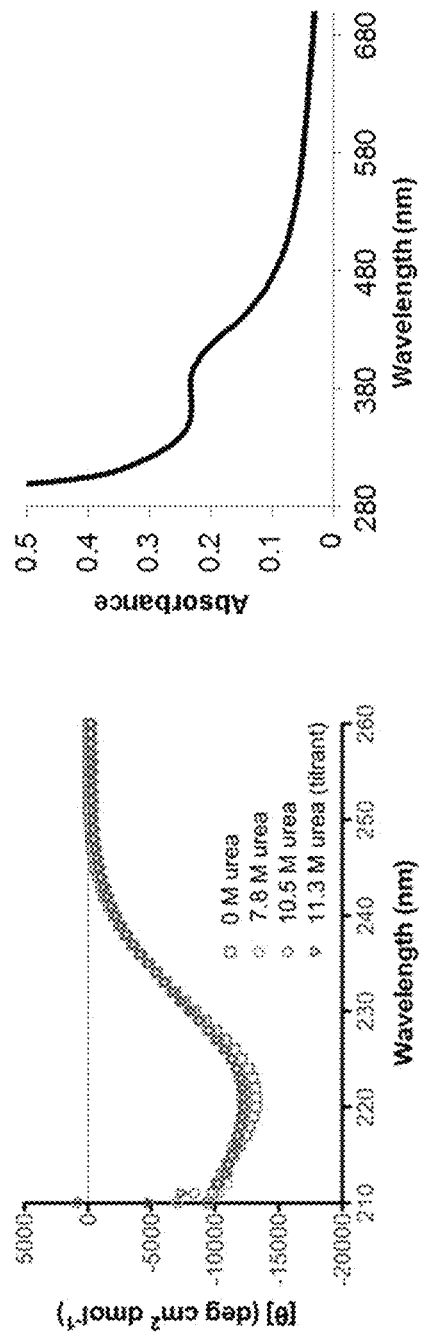
FIG. 6A
FIG. 6B
FIG. 6C
FIG. 6D

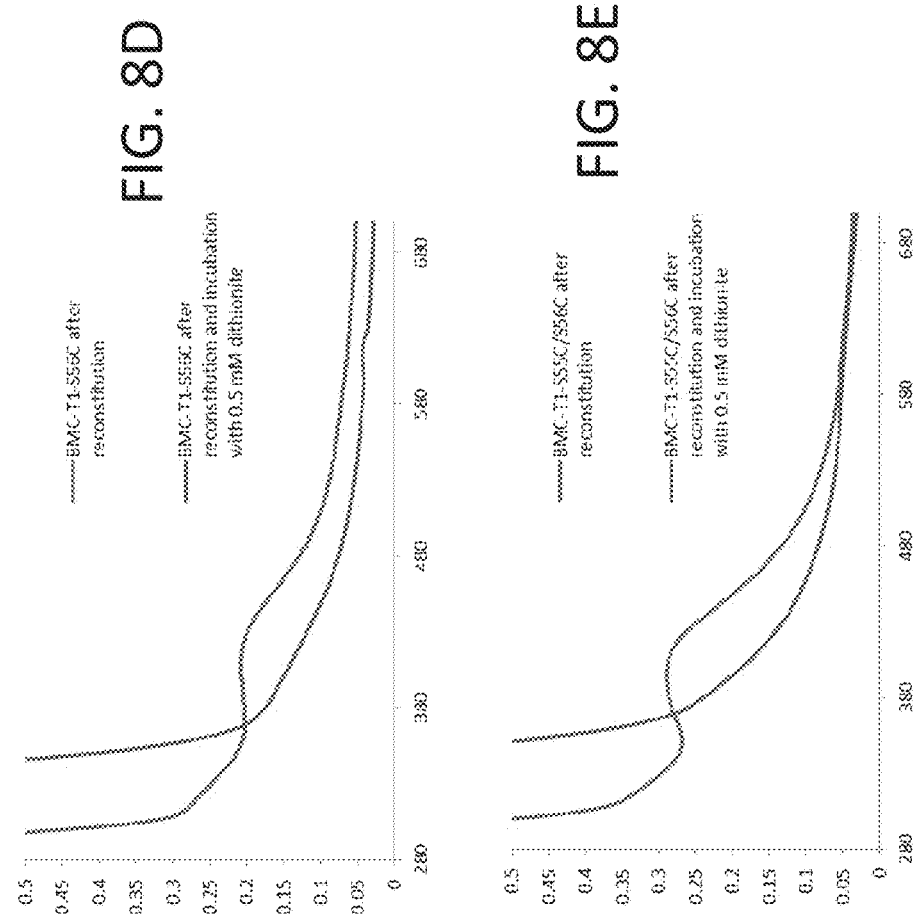
FIG. 8D
FIG. 8E
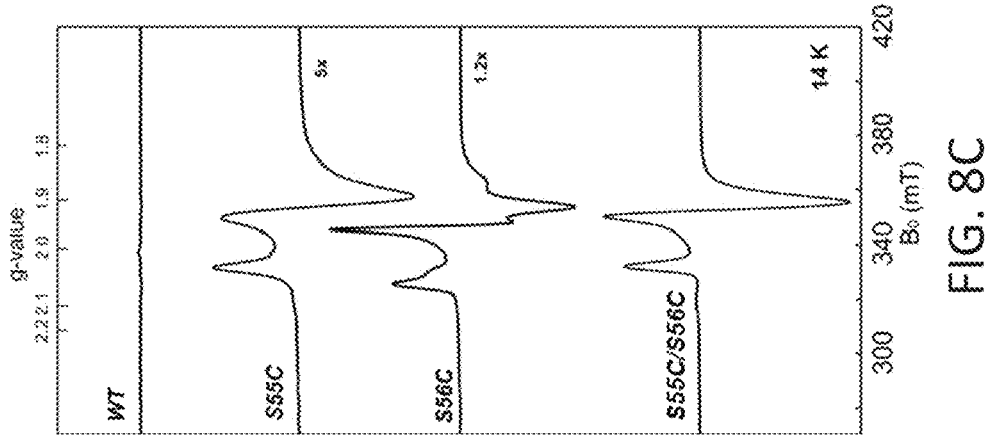
FIG. 8C

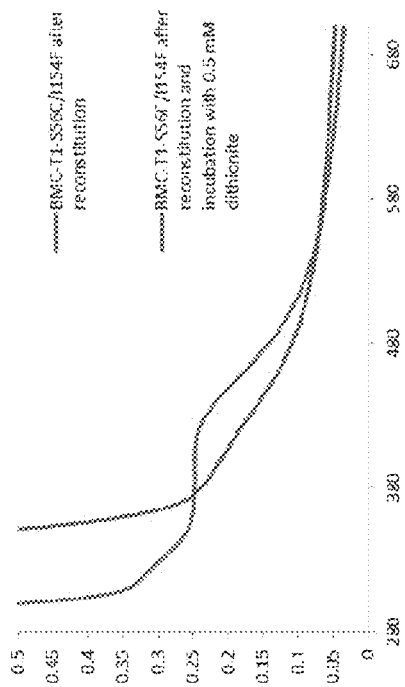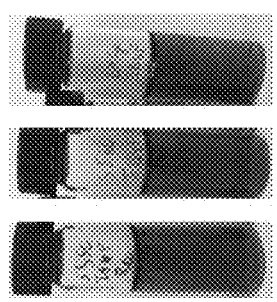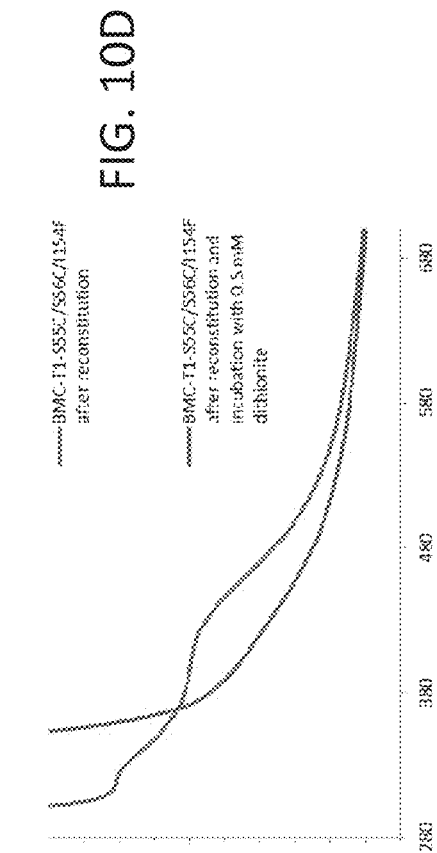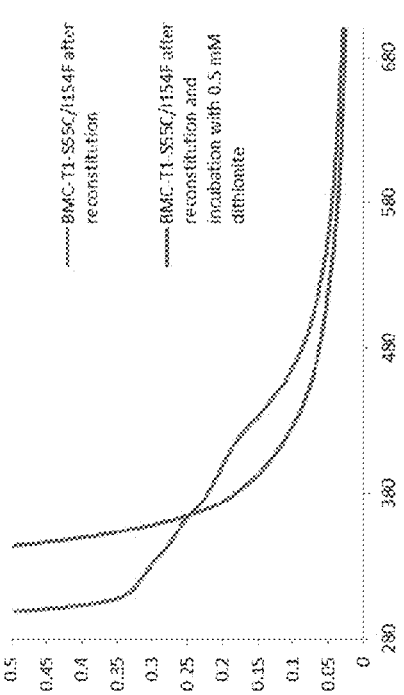

US 10,479,999 B2

ENGINEERED SHELL PROTEINS FOR MICROCOMPARTMENT SHELL ELECTRON TRANSFER AND CATALYSIS

This application claims benefit of priority to the filing date of U.S. Provisional Application Ser. No. 62/438,655, filed Dec. 23, 2016, the contents of which are specifically incorporated herein by reference in their entity.

FEDERAL FUNDING

This invention was made with government support under DE-FG02-91ER20021 awarded by the U.S. Department of Energy. The government has certain rights in the invention.

BACKGROUND OF THE INVENTION

Microbes have been used for many manufacturing purposes, including for energy production and the production of useful materials. With growing greenhouse-gas emissions, scientists are seeking better pathways to produce biofuels and other chemicals such as bioplastics. Although bacteria can be engineered to make all sorts of compounds and materials, the efficiencies of such methods are not optimal and the isolation of those compounds and materials can be laborious.

SUMMARY

Bacterial microcompartments (BMCs) are organelles used by various bacteria to encapsulate metabolic pathways into a proteinaceous shell. As illustrated herein, bacterial microcompartments can provide self-assembling modules, scaffold reactions in three dimensions, optimize reactions and stabilize enzymes in their lumens, and serve as catalytic bioreactors that can be customized to support new metabolic functions.

DESCRIPTION OF THE FIGURES

The patent or application file contains at least one drawing executed in color. Copies of this patent or patent application publication with color drawing(s) will be provided by the Office upon request and payment of the necessary fee.

FIG. 2A illustrates the structure of BMC-T1 in three orientations. The convex face of the trimer is shown on the left, the concave side on the right. Each protomer is represented in a different color. FIG. 2B illustrates $O_\gamma$-$O_\gamma$ trigonal distances between the side chains of the Ser55 residues converging at the three-fold symmetry axis (pore). FIG. 2C illustrates a side view of the pore region, showing the orientation of the side chains of the Ser55 residues (orange sticks identified by black arrows) towards the concave face. FIG. 2D shows refined $2F_o$–$F_c$ electron density maps of residues surrounding the three-fold symmetry axis in the BMC-T1 trimer. Electron density map contoured at 1 σ. Left: concave and right: convex surface of the BMC-T1 trimer. Ser55 residues are shown in orange. The density in the pore could not be assigned and is presumably a buffer or a salt molecule. FIG. 2E shows the colors of purified BMC-T1 (left) and purified BMC-T1-S55C (right). FIG. 2F shows a SDS gel stained using Coomassie Blue showing the purity of BMC-T1-S55C (arrow). FIG. 2G illustrates a typical size exclusion chromatogram obtained for BMC-T1-S55C. Similar chromatograms were obtained for BMC-T1. The arrow corresponds to a molecular weight of 69 kDa (calculated molecular weight of a monomer, 21.9 kDa). The first and last peaks are contaminants and do not contain any BMC-T1-S55C protein. Inset: calibration curve using standards of molecular weight 66 kDa (bovine serum albumin), 44 kDa (ovalbumin) and 17 kDa (myoglobin).

FIGS. 3A-3G illustrate the structure of BMC-T1-S55C. FIG. 3A shows a side view of the structure showing the [4Fe-4S] cluster (yellow and orange sticks). FIG. 3B shows an expanded view of the three-fold symmetry axis (pore region) showing the [4Fe-4S] cluster with the water molecule (red sphere) as the fourth unique iron ligand (black dashed line). Red dashed lines represent hydrogen bonds between the backbone amide of Gly155 and the sulfur atom of Cys55 while yellow dashed lines represent hydrogen bonds between the backbone amide of Ala157 and the cluster sulfides. FIG. 3C illustrates electrostati4 rendering of the BMC-T1-S55C trimer. Electrostatic surfaces are colored between −5 kT/e (red) and +5 kT/e (blue). FIG. 3D shows a $2F_o$–$F_c$ map (blue mesh) of the pore region of BMC-T1-S55C contoured at 1 σ. Iron ions are orange, and sulfides are yellow. FIG. 3E shows a simulated annealing omit (Fo–Fc) map of the [4Fe-4S] cluster at the BMC-T1-S55C trimer pore contoured at 3 rmsd/0.32 $e^-/Å^3$ with a rigid body fitted model of the [4Fe-4S] cluster (iron ions grey, sulfides green). FIG. 3F shows an anomalous difference electron density (red mesh) at the site of the iron atoms in the [4Fe-4S] cluster in BMC-T1-S55C, contoured at 4 σ (iron ions, orange, and sulfides, yellow). FIG. 3G illustrates structural superposition of BMC-T1 (dark grey) and BMC-T1-S55C (gold). The Ser55/Cys55 residues are circled, and the 14Fe-4S] cluster is represented as yellow and orange sticks.

FIG. 4A shows UV-Vis spectra where the solid line is the spectrum of BMC-T1-S55C as-isolated after reconstitution; the dashed line is the spectrum of BMC-T1-S55C after reconstitution and incubation with 0.5 mM dithionite; the dotted line is the spectrum of BMC-T1. The spectra were recorded at pH 7.5 and under anaerobic conditions for BMC-T1-S55C. FIG. 4B shows X-Band CW EPR spectra of BMC-T (top) and chemically reconstituted BMC-T1-S55C (bottom) after reduction with dithionite. The spectrum of BMC-T1 was recorded at 14 K. The spectra of BMC-T1-S55C were recorded at three different temperatures: 14 K (red trace), 27 K (black trace) and 47 K (blue trace) to demonstrate the relaxation behavior of the [4Fe-4S]$^{1+}$ signal. Experimental conditions: microwave frequency of 9.481 GHz, microwave power of 0.64 mW, modulation amplitude of 0.6 mT. FIG. 4C shows UV-Vis spectra of BMC-T1-S55C before and after reconstitution of the [4Fe-4S] cluster. The spectra were normalized at an optical density (280 nm) of 1 for comparison. FIG. 4D illustrates characterization of the [4Fe-4S] cluster in BMC-T1-S55C by continuous wave (CW) X-Band EPR spectra of three different preparations of BMC-T1-S55C, both in non-reconstituted (red trace) and reconstituted (blue trace) forms, after reduction with dithionite. Experimental conditions: microwave frequency of 9.481 GHz, microwave power of 0.64 mW, modulation amplitude of 0.6 mT, and temperature of 10 K. The vertical dashed line highlights the position of the $g_z$ component of the [4Fe-4S]$^{1+}$ cluster. FIG. 4E shows CW X-Band EPR spectra of non-reconstituted and reconstituted BMC-T1-S55 prior to and after addition of dithionite. The top EPR spectra (4E-1) show spectra of non-reconstituted BMC-T1-S55C in the absence (blue trace) and the presence of 10 mM dithionite (grey trace). The asterisk denotes a background signal from the resonator cavity. The bottom EPR spectra (4E-2) show spectra of reconstituted BMC-T1-S55C recorded on samples prior (red trace) and after (black trace) reduction with 10 mM dithionite. Experimental conditions: microwave frequency of 9.480 GHz, microwave power of 0.64 mW, modulation amplitude of 0.6 mT, and temperature of 14 K.

FIG. 5A illustrates the percentage of reduced protein as plotted versus the potential, and fitted using a single electron Nernst equation. The calculated $E_m$ is −370 mV vs. SHE at pH 7.5 and 25° C. FIG. 5B illustrates re-oxidation of the [4Fe-4S] cluster of BMC-T1-S55C after the redox titration. Spectra were recorded before the titration (using dithionite to reduce the cluster, solid blue line), after full reduction (dashed black line), and after re-oxidation using duroquinone (dotted black line). The additional observed signals in the dithionite-reduced spectrum are the contribution of the reduced redox mediator dyes. The solid blue and dotted black traces are essentially superimposable.

FIGS. 6A-6F illustrate chemical denaturation of BMC-T1 and BMC-T1-S55C. FIG. 6A illustrates CD spectra of BMC-T1 (circle symbols) and [4Fe-4S] cluster-bound BMC-T1-S55C (square symbols) before denaturation displaying two negative bands at 222 and 208 nm and a positive band at 195 nm, demonstrating α-helical and β-sheet structure, respectively. FIG. 6B illustrates chemical denaturation plot of BMC-T1 (circle symbols) and BMC-T1-S55C (square symbols). Denaturation was tracked at 222 nm. FIG. 6C illustrates CD spectra of BMC-T1-S55C at different urea concentrations, which all contained the same protein concentration of 8 M. These spectra were collected during the denaturation study. FIG. 6D illustrates a UV-Vis spectrum of BMC-T1-S55C after the titration (10.2 M urea final concentration) showing the presence of the [4Fe-4S] cluster at 385 nm. The spectrum was normalized to an optical density at 280 nm of 1. FIG. 6E-6F illustrate responses of BMC-T1-S55C exposed to atmospheric oxygen. FIG. 6E illustrates generation of a [3Fe-4S]$^{1+}$ cluster upon exposure of BMC-T1-S55C to air for variable times as monitored by EPR spectroscopy. The spectra correspond to a sample of the S55C-modified BMC variant as purified (without dithionite) under O$_2$-free conditions (red trace), after exposure to air at room temperature for 5 min (blue trace), 30 min (black trace) and 60 min (magenta trace). Experimental conditions: microwave power of 0.64 mW, modulation amplitude of 0.63 mT, temperature of 10° K, microwave frequency=9.480 GHz. FIG. 6F shows UV-Vis spectra of the cluster exposed to air for variable times. Bands at 310-330 nm and 465 nm are typical of [2Fe-2S] clusters.

FIG. 7A shows a face view of the pore region. FIG. 7B shows a side view of the pore region. The Ser55 residues (orange sticks) are oriented towards the concave face. The Ser56 residues (yellow sticks) are oriented towards the convex face. The Ile154 residues (red sticks) are located in the concave face, in the vicinity of the Ser55 residues. FIG. 7C shows a rear view (pore region) of a model of BMC-T1-S55C/I154F based on the structure of BMC-T1-S55C. The [4Fe-4S] cluster is represented as yellow and orange sticks, while modeled F154 residues are represented as grey sticks.

FIGS. 8A-8E illustrate structural and functional features of several variants of BMC-T1 binding [4Fe-4S] clusters. FIG. 8A shows the colors of purified BMC-T1 variants, from left to right: BMC-T1-S55C. BMC-T1-S56C, BMC-T1-S55C/S56C. Protein concentration varies between the different samples. FIG. 8B shows an expanded view of the three-fold symmetry axis of the pore region structure of the BMC-T1-S55C/S56. Red dashed lines represent hydrogen bonds between the backbone amide of Gly155 and the sulfur atom of Cys55 while yellow dashed lines represent hydrogen bonds between the backbone amide of Ala157 and the cluster sulfides. Black dashed lines represent the $S_\gamma$-$S_\gamma$ trigonal distances (5.5 to 5.7 Å) between the side chains of the Cys56 residues converging at the three-fold symmetry axis (pore). This represents a binding site for the cluster present in BMC-T1-S56C. FIG. 8C shows X-Band CW EPR spectra of BMC-T1 (top) and chemically reconstituted BMC-T1-S55C. BMC-T1-S56C and BMC-T1-S55C/S56C after reduction with dithionite. The spectra were recorded at 14 K. Experimental conditions: microwave frequency of 9.481 GHz, microwave power of 0.64 mW, modulation amplitude of 0.6 mT. FIG. 8D shows a UV-Vis spectrum of BMC-T1-S56C after reconstitution of the [4Fe-4S] cluster, before (blue line) and after (red line) reduction using dithionite. FIG. 8E shows a UV-Vis spectrum of BMC-T1-S55C/S56C after reconstitution of the [4Fe-4S] cluster, before (blue line) and after (red line) reduction using dithionite. The spectra shown in FIGS. 8D-8E were recorded at pH 7.5 under anaerobic conditions, and normalized at an optical density (280 nm) of 1 for comparison.

FIGS. 10A-10G show features of several BMC-T1 variants binding [4Fe-4S] clusters that include the I154F mutation. FIG. 10A shows the colors of purified BMC-T1 variants, shown from left to right: BMC-T1-S55C/I154F, BMC-T1-S56C/I154F, BMC-T1-S55C/S56C/I154F. Protein concentration varies between the different samples. FIG. 10B shows a UV-Vis spectrum of BMC-T1-S55C/154F after reconstitution of the [4Fe-4S] cluster, before (blue line) and after (red line) reduction using dithionite. FIG. 10C shows a UV-Vis spectrum of BMC-T1-S56C/I154F after reconstitution of the [4Fe-4S] cluster, before (blue line) and after (red line) reduction using dithionite. FIG. 10D shows a UV-Vis spectrum of BMC-T1-S55C/S56C/I154F after reconstitution of the [4Fe-4S] cluster, before (blue line) and after (red line) reduction using dithionite. The spectra shown in FIGS. 10B-10D were recorded at pH 7.5 under anaerobic conditions, and normalized at an optical density (280 nm) of 1 for comparison. FIG. 10E shows X-Band CW EPR spectra of BMC-T1-S55C/I154F after reduction with dithionite, as purified (red trace) and after chemical reconstitution of the [4Fe-4S] cluster (blue trace). FIG. 10F shows X-Band CW EPR spectra of BMC-T1-S56C/I154F after reduction with dithionite, as purified (red trace) and after chemical reconstitution of the [4Fe-4S] cluster (blue trace). FIG. 10G shows X-Band CW EPR spectra of BMC-T I-S55C/S56C after reduction with dithionite, as purified (red trace) and after chemical reconstitution of the [4Fe-4S] cluster (blue trace). Other experimental conditions for the spectra shown in FIG. 10E-10G: modulation amplitude: 0.6 mT, points 2048, scan time 169 s, temperature 10 K, microwave power 1 mW.

FIG. 11A graphically illustrates the reduction potential of the BMC-T1-S55C, BMC-T1-S56C and BMC-T 1-S 55C/S 56C [4Fe-4S] clusters. FIG. 11B graphically illustrates the reduction potential of the BMC-T1-S55C/I154F [4Fe-4S] cluster. The calculated $E_m$ were −370 mV, −455 mV, −310 mV and −460 mV vs. SHE at pH 7.5 and 25° C. for BMC-T-S55C, BMC-T1-S56C, BMC-T1-S55C/S56C and BMC-T1-S55C/I154F respectively.

DETAILED DESCRIPTION

Figure 1:
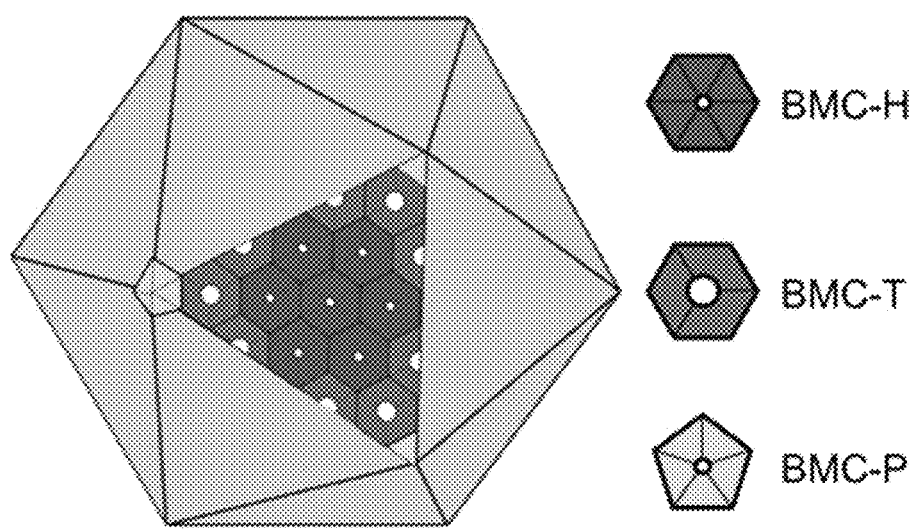
FIG. 1 schematically illustrates the organization of a bacterial microcompartment (BMC) shell and the composition of a BMC shell. For clarity, only one facet of the icosahedron is tiled with shell proteins BMC-H (blue hexagon), BMC-T (red hexagon with larger hole in the middle), and BMC-P (yellow pentagon).

Described herein are bacterial microcompartment shell proteins that have been modified to include cysteine residues for incorporation of metals (e.g. iron-sulfur clusters) into the bacterial microcompartment shells. Such modified bacterial microcompartments can, for example, have a reduction potential of −500 to −200 mV, or −455 to −370 mV versus the Standard Hydrogen Electrode (SHE). For example, as illustrated herein, the reduction potential of the engineered [4Fe-4S] cluster in BMC-T1-S55C (SEQ ID NO:3) is −370 mV versus the Standard Hydrogen Electrode (SHE). Other mutants were designed to fine-tune this reduction potential value: −455 mV and −310 mV versus SHE for BMC-T1-S56C (SEQ ID NO:4) and BMC-T1-S55C/S56C (SEQ ID NO:5) respectively. These clusters have also been shown to be redox active and stable through redox cycling. Furthermore, the substitution of an isoleucine residue in the vicinity of the [4Fe-4S] cluster with a phenylalanine residue creates a hydrophobic environment around the cluster that is useful for the fine-tuning of the reduction potential of the cluster. Hence, the modifications to bacterial microcompartment shell proteins confer electron transfer functionality to bacterial microcompartment shells. Such modifications can be fine-tuned to confer new catalytic activities to microcompartment shell proteins.

Modified bacterial microcompartments described herein therefore introduce electron transfer functionality into bacterial microcompartment shells. This can support encapsulation of oxidoreductive pathways. A bacterial microcompartment shell protein BMC-T1 from *H. ochraceum* was engineered to have point mutation that allow the microcompartments to bind metals such as iron-sulfur clusters. These metal containing microcompartment shell proteins, when incorporated, can transfer electrons (oxidation-reduction cycles) from one side of the bacterial microcompartment to the other. The constructs described herein provide different varieties of the modified BMC-T1 protein through specific point mutations in the interprotein pore, which enables several redox potentials to cater to various needs.

Bacterial microcompartments can also serve as nanobiocatalytic reactors in vivo or in vitro. For example, the modified bacterial microcompartments can also encapsulate a nitrogenase so that the combination of nitrogenase and the redox reactions can improve nitrogen fixation. The modified bacterial microcompartments can also encapsulate one or more enzymes of the methylerythritol 4-phosphate (MEP) pathway (e.g., IspG and IspH) to improve production of the basic building blocks for the biosynthesis of terpenes. Such terpenes include numerous chemicals (more than 55,000 are known) that provide starting materials and intermediates for production of pharmaceuticals, biofuels, fragrances and more. For example, IspG and IspH are [4Fe-4S] cluster enzymes that could use electrons transferred by engineered shell proteins for their catalytic activity. IspG and IspH are generally sensitive to oxygen and not very catalytically efficient, encapsulation in a microcompartment shell protects them from oxygen and can improve their efficiency. In another example, the modified bacterial microcompartments can also include NAD/NADP, which can transform the modified microcompartments and/or host cells that have such modified microcompartments into bio-batteries.

Modification of Bacterial Microcompartments

The modified bacterial microcompartment shell proteins described herein have one or more cysteine residues incorporated into them. For example, one or more amino acids that line the shell protein pore can be replaced with one or more cysteine residues. In some cases, two or more amino acids within the microcompartment pore can be replaced with two or more cysteine residues. In some cases, three or more amino acids within the microcompartment pore can be replaced with three or more cysteine residues. The position of the substituted residues, which coordinate with or are in the vicinity of the redox active metal, can be varied to alter metal selectivity and/or midpoint potential.

Any amino acid within a microcompartment shell protein can be replaced to provide the modified microcompartment proteins. For example, any of the following amino acids within microcompartment shell proteins can be replaced: serine, threonine, valine, leucine, isoleucine, methionine, aspartic acid, asparagine, alanine, arginine, aspartic acid, glutamic acid, glutamine, glycine, histidine, isoleucine, leucine, lysine, methionine, phenylalanine, proline, tryptophan or tyrosine. In some cases, the amino acid is not aspartic acid, isoleucine, leucine, or methionine. In some cases, when an amino acid is replaced by a cysteine, the replace amino acid can be about the same size as a cysteine residue. Cysteine has a molecular weight of 103.15 g/mole and the following structure.

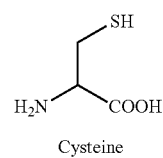

Cysteine

Examples of amino acids that can be replaced by cysteine in the modified bacterial microcompartments include serine, threonine, valine, leucine, isoleucine, methionine, aspartic acid, and asparagine as well as other amino acid substitutions.

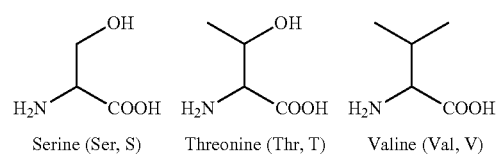

Serine (Ser, S)     Threonine (Thr, T)     Valine (Val, V)

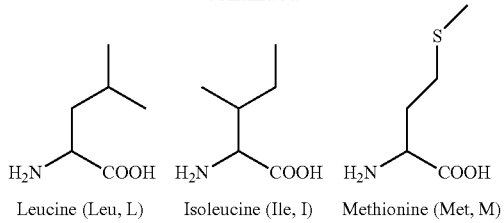

Leucine (Leu, L)  Isoleucine (Ile, I)  Methionine (Met, M)

The site(s) of amino acid replacement within the bacterial microcompartment shells include sites that project amino acid side chains of the replacement amino acids into the interior or to the exterior of the microcompartments. In some cases, the site(s) of amino acid replacement within the bacterial microcompartments include sites that are within the microcompartments or are near one or more pore openings of the microcompartments.

A bacterial microcompartment shell typically has three different types of proteins that serve as its basic building blocks (see FIG. 1). BMC-H subunits (single Pfam00936 domain) assemble into a cyclic hexamer. Tandem (BMC-T) proteins consist of a fusion of two Pfam00936 domains. BMC-T trimers form a pseudohexamer (Klein et al., *J. Mol. Biol.* 392: 319 (2009); Sagermann et al., *Proc. Natl. Acad. Sci. U.S.A.* 106: 8883 (2009). BMC-P proteins (single Pfam03319 domain) assemble into pentamers that cap the vertices of an apparently icosahedral shell (FIG. 1; Tanaka et al. *Science* 319: 1083 (2008); Sutter et al., *Photosynth. Res.* 18: 9 (2013)); and Wheatley et al., *Protein Sci.* 22: 660 (2013)). The shell protein oligomers typically contain pores at the symmetry axis that are proposed to function as selective conduits for the diffusion of metabolites (substrates and products) into and out of the BMC lumen (Kerfeld et al., *Science* 309: 936 (2005); and Kinney et al., *Photosynth. Res.* 109: 21 (2011)).

An example of a *Haliangium ochraceum* BMC-T1 (Hoch_5812) has the following amino acid sequence (SEQ ID NO: 1).

```
  1 MDHAPERFDA TPPAGEPDRP ALGVLELTSI ARGITVADAA

41 LKRAPSLLLM SRPVSSGKHL LMMRGQVAEV EESMIAAREI

81 AGAGSGALLD ELELPYAHEQ LWRFLDAPVV ADAWEEDTES

121 VIIVETATVC AAIDSADAAL KTAPVVLRDM RLAIGIAGKA

161 FFTLTGELAD VEAAAEVVRE RCGARLLELA CIARPVDELR

181 GRLFF
```

A nucleotide segment encoding the SEQ ID NO: 1 BMC-T1 protein with SEQ ID NO: 1 can, for example, have the nucleotide sequence shown below as SEQ ID NO:2.

```
  1 ATGGACCACG CTCCGGAACG CTTTGATGCG ACCCCGCCGG

41 CAGGTGAACC GGACCGCCCG GCACTGGGTG TGCTGGAACT

81 GACCTCAATT GCTCGTGGTA TCACCGTTGC GGATGCGGCC

121 CTGAAACGTG CACCGAGTCT GCTGCTGATG TCCCGCCCGG

161 TCAGCTCTGG CAAGCATCTG CTGATGATGC GTGGCCAGGT

201 GGCAGAAGTT GAAGAATCAA TGATTGCAGC TCGCGAAATC
```

```
241 GCTGGTGCAG GTTCGGGTGC TCTGCTGGAT GAACTGGAAC

281 TGCCGTATGC GCACGAACAA CTGTGGCGCT TTCTGGACGC

321 ACCGGTGGTT GCAGATGCAT GGGAAGAAGA CACCGAAAGC

361 GTCATTATCG TGGAAACCGC GACGGTGTGC GCGGCCATTG

401 ATAGTGCCGA CGCAGCTCTG AAAACGGCAC CGGTCGTGCT

441 GCGTGATATG CGCCTGGCCA TTGGTATCGC TGGCAAGGCG

481 TTTTTCACCC TGACGGGTGA ACTGGCAGAC GTGGAAGCGG

521 CCGCAGAAGT TGTCCGTGAA CGTTGCGGTG CACGTCTGCT

561 GGAACTGGCA TGTATCGCAC GCCCGGTTGA TGAACTGCGT

601 GGCCGCCTGT TTTTCTAA
```

A modification of such a BMC-T1 structure involving substitution of serine at position 55 with a cysteine (S55C) was made in the BMC-T1 gene using the QuikChange Lightning site-directed mutagenesis kit (Agilent Technologies). An amino acid sequence for such a S55C-modified BMC-T1 (BMC-T1-S55C) protein is as follows (SEQ ID NO:3).

```
  1 MDHAPERFDA TPPAGEPDRP ALGVLELTSI ARGITVADAA

41 LKRAPSLLLM SRPVCSGKHL LMMRGQVAEV EESMIAAREI

81 AGAGSGALLD ELELPYAHEQ LWRFLDAPVV ADAWEEDTES

121 VIIVETATVC AAIDSADAAL KTAPVVLRDM RLAIGIAGKA

161 FFTLTGELAD VEAAAEVVRE RCGARLLELA CIARPVDELR

181 GRLFF
```

Figure 3C:
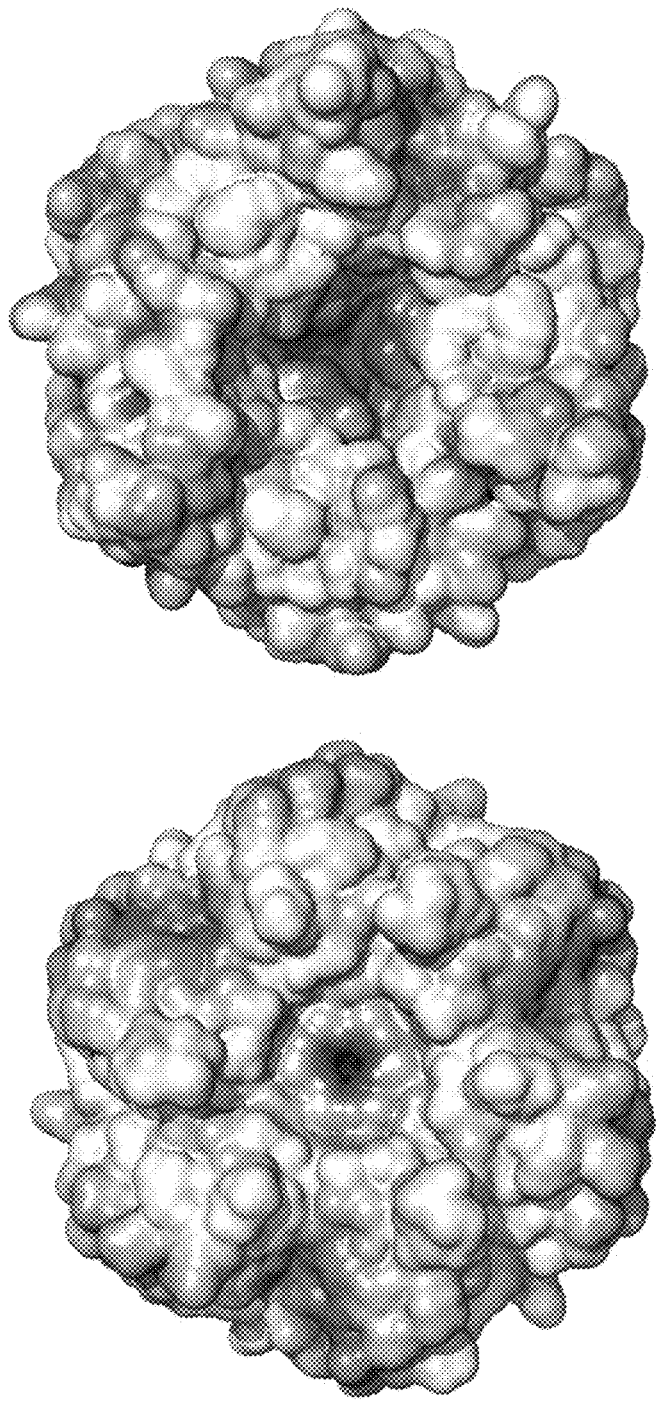
Figure 3C:
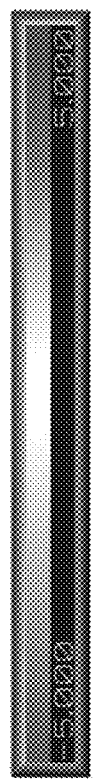
Figure 3D:
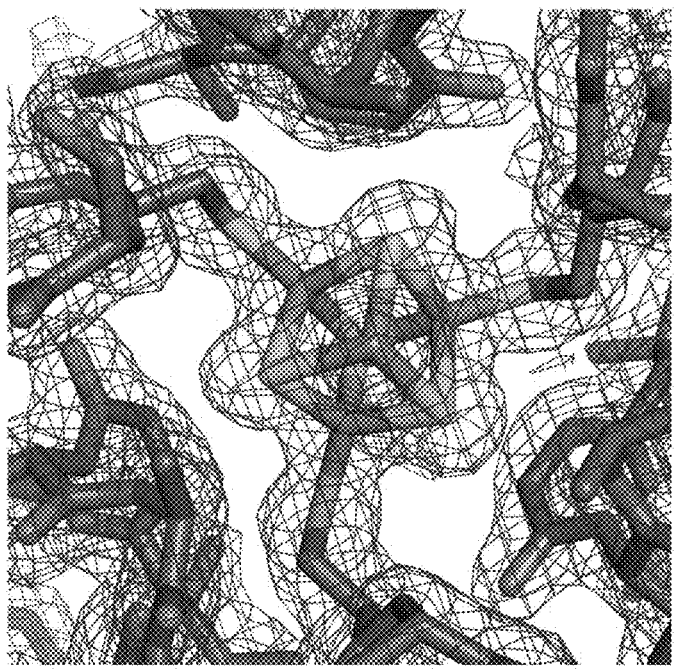

As illustrated herein, the BMC-T1-S55C monomer scaffold is composed of two domains which have complementary roles for interaction with metal atoms. The first domain harbors the [4Fe-4S] cluster-binding site (Cys55), while residues within the second domain (Gly155 and Ala157) provide hydrogen bonding interactions that most likely stabilizes the [4Fe-4S] cluster and facilitates its redox reversibility. In most [Fe—S] cluster proteins, the cluster ligands are on the same polypeptide chain; in contrast, each BMC-T1-S55C protomer contributes one-third of the [4Fe-4S] cluster binding site, which is completed by the trimerization. As observed in other systems, three cysteine ligands are sufficient for [4Fe-4S] incorporation. The fourth ligand can vary: for example, in radical SAM enzymes, when SAM is present it is the fourth ligand (Broderick et al., *Chem. Rev.* 114: 4229 (2014)). Similarly to activated aconitase and other dehydratase enzymes, a water molecule (or hydroxide ion) completes the primary coordination sphere of the cluster in BMC-T1-S55C (FIG. 3B). Therefore, the [4Fe-4S] cluster of BMC-T1-S55C can be considered a hybrid between clusters found in low-potential bacterial ferredoxins (redox and spectroscopic characteristics) and those found in different classes of enzymes (architecture of the cluster).

A modification of such a BMC-T1 structure involving substitution of serine at position 56 with a cysteine (S56C) was made in the BMC-T1 gene using the QuikChange Lightning site-directed mutagenesis kit (Agilent Technologies). An amino acid sequence for such a S56C-modified BMC-T1 (BMC-T1-S56C) protein is as follows (SEQ ID NO:4).

```
  1 MDHAPERFDA TPPAGEPDRP ALGVLELTSI ARGITVADAA

41 LKRAPSLLLM SRPVSCGKHL LMMRGQVAEV EESMIAAREI

81 AGAGSGALLD ELELPYAHEQ LWRFLDAPVV ADAWEEDTES

121 VIIVETATVC AAIDSADAAL KTAPVVLRDM RLAIGIAGKA

161 FFTLTGELAD VEAAAEVVRE RCGARLLELA CIARPVDELR

181 GRLFF
```

A modification of such a BMC-T1 structure involving substitutions of serine residues at positions 55 and 56 with a cysteine (S55C/S56C) were made in the BMC-T1 gene using the QuikChange Lightning site-directed mutagenesis kit (Agilent Technologies). An amino acid sequence for such a S55C/S56C-modified BMC-T1 (BMC-T1-S55C/S56C) protein is as follows (SEQ ID NO:5).

```
  1 MDHAPERFDA TPPAGEPDRP ALGVLELTSI ARGITVADAA

41 LKRAPSLLLM SRPVCCGKHL LMMRGQVAEV EESMIAAREI

81 AGAGSGALLD ELELPYAHEQ LWRFLDAPVV ADAWEEDTES

121 VIIVETATVC AAIDSADAAL KTAPVVLRDM RLAFGIAGKA

161 FFTLTGELAD VEAAAEVVRE RCGARLLELA CIARPVDELR

181 GRLFF
```

A modification of such a BMC-T1 structure involving substitutions of serine at position 55 with a cysteine (S55C) and isoleucine at position 154 with a phenylalanine (I154F) were made in the BMC-T1 gene using the QuikChange Lightning site-directed mutagenesis kit (Agilent Technologies). An amino acid sequence for such a S55C/I154F-modified BMC-T1 (BMC-T1-S55C/I154F) protein is as follows (SEQ ID NO:6).

```
  1 MDHAPERFDA TPPAGEPDRP ALGVLELTSI ARGITVADAA

41 LKRAPSLLLM SRPVCSGKHL LMMRGQVAEV EESMIAAREI

81 AGAGSGALLD ELELPYAHEQ LWRFLDAPVV ADAWEEDTES

121 VIIVETATVC AAIDSADAAL KTAPVVLRDM RLAFGIAGKA

161 FFTLTGELAD VEAAAEVVRE RCGARLLELA CIARPVDELR

181 GRLFF
```

A modification of such a BMC-T1 structure involving substitutions of serine at position 56 with a cysteine (S56C) and isoleucine at position 154 with a phenylalanine (I154F) were made in the BMC-T1 gene using the QuikChange Lightning site-directed mutagenesis kit (Agilent Technologies). An amino acid sequence for such a S56C/I154F-modified BMC-T1 (BMC-T1-S56C/I154F) protein is as follows (SEQ ID NO:7).

```
  1 MDHAPERFDA TPPAGEPDRP ALGVLELTSI ARGITVADAA

41 LKRAPSLLLM SRPVSCGKHL LMMRGQVAEV EESMIAAREI

81 AGAGSGALLD ELELPYAHEQ LWRFLDAPVV ADAWEEDTES

121 VIIVETATVC AAIDSADAAL KTAPVVLRDM RLAFGIAGKA

161 FFTLTGELAD VEAAAEVVRE RCGARLLELA CIARPVDELR

181 GRLFF
```

A modification of such a BMC-T1 structure involving substitutions of serine at positions 55 and 56 with a cysteine (S55C/S56C) and isoleucine at position 154 with a phenylalanine (I154F) were made in the BMC-T1 gene using the QuikChange Lightning site-directed mutagenesis kit (Agilent Technologies). An amino acid sequence for such a S55C/S56C/I154F-modified BMC-T1 (BMC-T1-S55C/S56C/I154F) protein is as follows (SEQ ID NO:8).

```
  1 MDHAPERFDA TPPAGEPDRP ALGVLELTSI ARGITVADAA

41 LKRAPSLLLM SRPVCCGKHL LMMRGQVAEV EESMIAAREI

81 AGAGSGALLD ELELPYAHEQ LWRFLDAPVV ADAWEEDTES

121 VIIVETATVC AAIDSADAAL KTAPVVLRDM RLAFGIAGKA

161 FFTLTGELAD VEAAAEVVRE RCGARLLELA CIARPVDELR

181 GRLFF
```

Figure 7B:
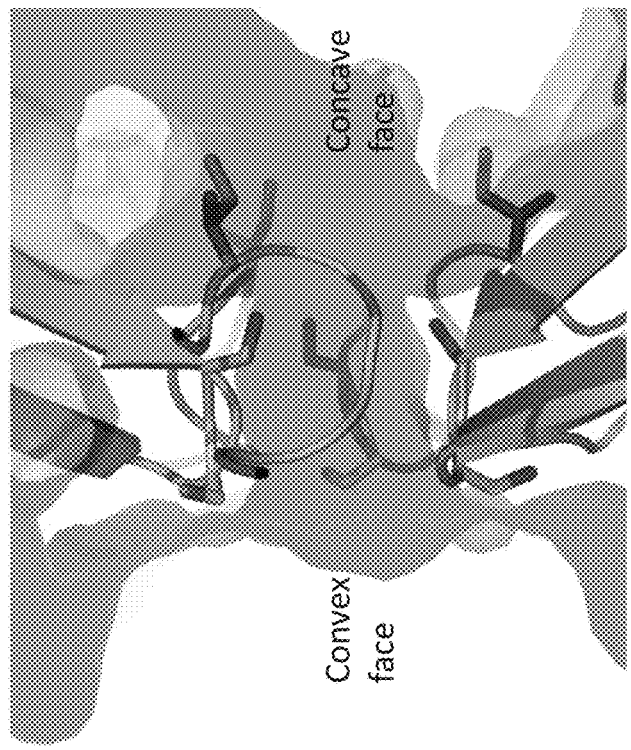
FIGS. 7A-7C show views of the pore region structure at the three-fold symmetry axis of a BMC-T1 trimer.
Figure 7A:
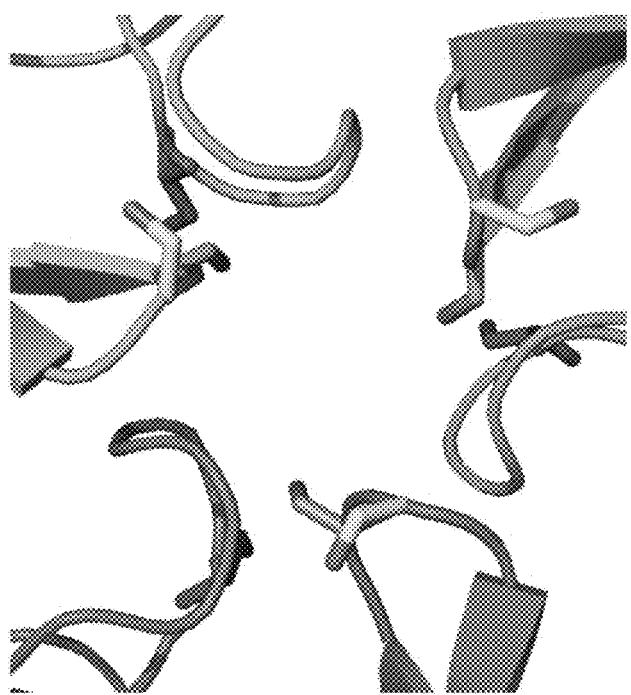
Figure 7C:
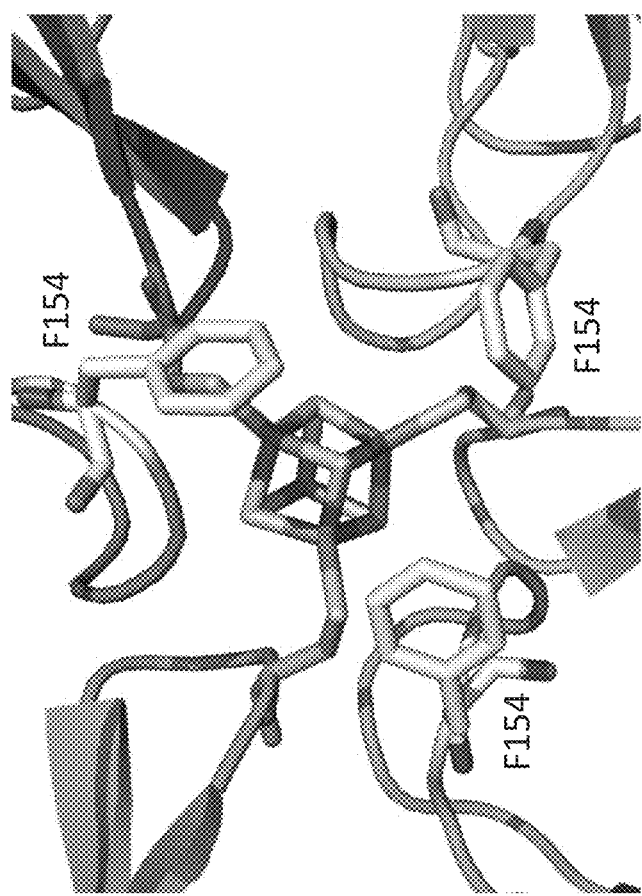

These mutations have been designed to create an alternative [4Fe-4S] cluster binding site or to alter the environment of the cluster, with the objective of fine-tuning its reduction potential. More specifically, the S55C and S56C mutations provide [4F-4S] cluster binding sites located in the concave and the convex face of BMC-T1, respectively (FIG. 7). The presence of a double set of cysteine residues (S55C/S56C) as well as the mutation of an adjacent isoleucine residue to a phenylalanine residue modifies the environment of the cluster and its properties.

To form its shell, a bacterial microcompartment assembles from several BMC-T subunits (e.g., three BMC-T subunits), several BMC-P subunits (e.g., three BMC-P subunits) and at least one BMC-H subunit.

An example, of an amino acid sequence for a *Haliangium ochraceum* BMC-H (Hoch_5815) shell subunit is shown below as SEQ ID NO:9.

```
  1 MADALGMIEV RGFVGMVEAA DAMVKAAKVE LIGYEKTGGG

41 YVTAVVRGDV AAVKAATEAG QRAAERVGEV VAVHVIPRPH

81 VNVDAALPLG RTPGMDKSA
```

A nucleotide sequence for this *Haliangium ochraceum* BMC-H (Hoch_5815) shell protein is shown below as SEQ ID NO: 10.

```
  1 ATGGCGGACG CACTGGGTAT GATTGAAGTT CGTGGTTTTG

41 TTGGTATGGT GGAAGCGGCG GATGCTATGG TGAAAGCGGC

81 TAAAGTTGAA CTGATTGGTT ATGAAAAAAC CGGCGGTGGC

121 TACGTGACGG CAGTGGTTCG TGGTGATGTC GCAGCAGTTA

161 AGGCAGCTAC CGAAGCCGGT CAGCGTGCAG CAGAACGTGT

201 TGGTGAAGTC GTGGCAGTTC ATGTCATCCC GCGTCCGCAC

241 GTGAACGTTG ATGCAGCTCT GCCGCTGGGT CGTACGCCGG

321 GTATGGACAA AAGCGCGTAA
```

An example of an amino acid sequence for a *Haliangium ochraceum* BMC-T3 (Hoch_3341) shell protein is shown below as SEQ ID NO:11.

```
  1 MELRAYTVLD ALQPQLVAFL QTVSTGFMPM EQQASVLVEI
 41 APGIAVNQLT DAALKATRCQ PGLQIVERAY GLIEMHDDDQ
 81 GQVRAAGDAM LAHLGAREAD RLAPRVVSSQ IITGIDGHQS
121 QLINRMRHGD MIQAGQTLYI LEVHPAGYAA LAANEAEKAA
161 PIKLLEVVTF GAFGRLWLGG GEAEIAEAAR AAEGALAGLS
201 GRDNRG
```

A nucleotide segment encoding the *Haliangium ochraceum* BMC-T3 (Hoch_3341) shell protein can, for example, have the following nucleotide sequence (SEQ ID NO:12).

```
  1 ATGGAACTGC GTGCTTATAC GGTCCTGGAT GCCCTGCAGC
 41 CGCAACTGGT CGCCTTTCTG CAAACGGTGT CAACGGGTTT
 81 CATGCCGATG AACAGCAAG CGAGCGTTCT GGTCGAAATT
121 GCACCGGGTA TCGCTGTCAA CCAGCTGACC GACGCAGCAC
161 TGAAAGCAAC GCGTTGCCAG CCGGGTCTGC AAATTGTGGA
201 ACGTGCGTAT GGCCTGATCG AAATGCATGA TGACGATCAG
241 GGTCAAGTTC GTGCAGCTGG TGACGCAATG CTGGCACACC
281 TGGGTGCACG TGAAGCTGAT CGTCTGGCAC CGCGTGTGGT
321 TAGCTCTCAG ATTATCACCG GTATTGACGG CCATCAGAGT
361 CAACTGATCA ACCGTATGCG CCACGGTGAT ATGATTCAGG
401 CAGGCCAAAC GCTGTATATC CTGGAAGTTC ATCCGGCAGG
441 TTACGCAGCA CTGGCAGCTA ATGAAGCCGA AAAAGCGGCC
481 CCGATTAAGC TGCTGGAAGT CGTGACCTTT GGTGCATTCG
521 GTCGTCTGTG GCTGGGTGGT GGTGAAGCAG AAATCGCAGA
561 AGCAGCTCGT GCGGCAGAAG GTGCACTGGC TGGTCTGTCC
601 GGCCGTGATA ATCGCGGCTA A
```

An example of another amino acid sequence for a *Haliangium ochraceum* BMC-T2 (HOCH_5816) shell protein is shown below as SEQ ID NO: 13.

```
  1 MSITLRTYIF LDALQPQLAT FIGKTARGFL PVPGQASLWV
 41 EIAPGIAINR VTDAALKATK VQPAVQVVER AYGLLEVHHF
 81 DQGEVLAAGS TILDKLEVRE EGRLKPQVMT HQIIRAVEAY
121 QTQIINRNSQ GMMILPGESL FILETQPAGY AVLAANEAEK
161 AANVHLVNVT PYGAFGRLYL AGSEAEIDAA AEAAEAAIRS
201 VSGVAQESFR DR
```

A nucleotide segment encoding the *Haliangium ochraceum* BMC-T2 (HOCH_5816) shell protein can, for example, have the following nucleotide sequence (SEQ ID NO: 14).

```
  1 ATGTCAATCA CCCTGCGCAC CTATATCTTT CTGGACGCCC
 41 TGCAACCGCA ACTGGCAACC TTCATCGGCA AAACGGCTCG
 81 TGGCTTCCTG CCGGTCCCGG GTCAGGCAAG CCTGTGGGTG
121 GAAATTGCTC CGGTATTGC GATCAACCGT GTGACCGATG
161 CGGCCCTGAA AGCTACGAAG GTGCAGCCGG CGGTTCAAGT
201 GGTTGAACGC GCGTATGGCC TGCTGGAAGT TCATCACTTC
241 GATCAGGGCG AAGTCCTGGC AGCTGGTAGT ACCATCCTGG
281 ACAAACTGGA AGTTCGTGAA GAAGGTCGCC TGAAGCCGCA
321 GGTGATGACC CATCAAATTA TCCGTGCTGT TGAAGCGTAT
361 CAGACGCAAA TTATCAACCG CAATAGTCAG GGCATGATGA
401 TTCTGCCGGG TGAATCCCTG TTTATCCTGG AAACCCAACC
441 GGCAGGTTAC GCAGTCCTGG CAGCCAATGA AGCCGAAAAA
481 GCAGCTAACG TTCACCTGGT CAATGTGACG CCGTATGGCG
521 CATTCGGTCG TCTGTACCTG GCCGGCTCAG AAGCAGAAAT
561 TGATGCGGCC GCAGAAGCTG CGGAAGCCGC AATCCGCAGC
601 GTTTCTGGTG TCGCGCAGGA ATCGTTTCGT GACCGCTAA
```

An example, of an amino acid sequence for a *Haliangium ochraceum* BMC-P (Hoch_4425) shell protein is shown below as SEQ ID NO:15.

```
  1 MYLGRVIGTV VAERKVAGLE GAKLLLVQPL DDALSPVGGV
 41 QAAVDTVQAG PDDLVYLVGS REAALALTPS FVPVDAAIVG
 81 IVDDVHAPER AS
```

A nucleotide segment encoding the *Haliangium ochraceum* BMC-P (Hoch_4425) shell protein can, for example, have the following nucleotide sequence (SEQ ID NO: 16).

```
  1 ATGTATCTGG GTCGTGTGAT TGGTACCGTG GTGGCTGAAC
 41 GCAAAGTGGC GGGTCTGGAA GGCGCAAAAC TGCTGCTGGT
 81 GCAACCGCTG GATGACGCAC TGAGTCCGGT CGGTGGTGTG
121 CAGGCAGCAG TTGATACCGT CCAAGCAGGT CCGGATGACC
161 TGGTGTATCT GGTTGGTAGC CGTGAAGCAG CTCTGGCGCT
201 GACGCCGTCT TTTGTGCCGG TTGATGCGGC CATTGTCGGC
241 ATCGTTGATG ACGTGCATGC ACCGGAACGC GCTAGCTAA
```

An example of another amino acid sequence for a *Haliangium ochraceum* BMC-P (Hoch_4426) shell protein is shown below as SEQ ID NO:17.

```
  1 MRLCRVLGSV VATVKHPVYN GLPLMIVQPL DDAGRDAGAS
 41 FLAVDNVQSG PGDRVLVLTE GGGVRQILAL GDQVPIRSLI
 81 VGVVDAVDGV AATGVDDAGG AADSAAAAKS VRADELPADA
121 SAAGRGE
```

A nucleotide segment encoding the *Haliangium ochraceum* BMC-P (Hoch_4426) shell protein can, for example, have the following nucleotide sequence (SEQ ID NO: 18).

```
  1 ATGCGTCTGT GTCGTGTTCT GGGCTCCGTC GTCGCCACCG
 41 TCAAGCACCC GGTCTACAAT GGTCTGCCGC TGATGATCGT
```

```
 81 TCAACCGCTG GATGACGCAG GTCGTGATGC AGGCGCTAGT

121 TTTCTGGCTG TTGATAACGT CCAGTCCGGT CCGGGTGACC

161 GTGTCCTGGT GCTGACCGAA GGTGGTGGTG TGCGTCAGAT

201 TCTGGCACTG GGTGATCAAG TCCCGATTCG CAGCCTGATC

241 GTGGGCGTGG TTGATGCAGT GGACGGTGTT GCAGCAACGG

281 GTGTTGATGA CGCAGGTGGT GCAGCTGATA GCGCAGCAGC

321 AGCTAAATCT GTCCGTGCAG ATGAACTGCC GGCAGACGCA

361 AGCGCGGCCG GTCGCGGCGA ATAA
```

An example of another amino acid sequence for a *Haliangium ochraceum* BMC-P (Hoch_5814) shell protein is shown below as SEQ ID NO:19.

```
  1 MVLGKVVGTV VASRKEPRIE GLSLLLVRAC DPDGTPTGGA

41 VVCADAVGAG VGEVVLYASG SSARQTEVTN NRPVDATIMA

81 IVDLVEMGGD VRFRKD
```

A nucleotide segment encoding the *Haliangium ochraceum* BMC-P (Hoch_5814) shell protein can, for example, have the following nucleotide sequence (SEQ ID NO:20).

```
  1 ATGGTCCTGG GTAAAGTCGT GGGTACGGTG GTGGCGAGCC

41 GCAAAGAACC GCGCATTGAA GGTCTGAGCC TGCTGCTGGT

81 CCGTGCCTGC GATCCGGACG GTACCCCGAC GGGTGGTGCA

121 GTGGTTTGTG CAGATGCAGT GGGTGCAGGT GTTGGTGAAG

161 TCGTGCTGTA TGCGAGTGGC AGCTCTGCCC GTCAGACCGA

201 AGTCACGAAC AATCGCCCGG TTGATGCAAC CATTATGGCT

241 ATCGTTGACC TGGTCGAAAT GGGCGGTGAT GTGCGTTTTC

281 GCAAAGACTAA
```

A synthetic operon was constructed with ribosomal binding site sequences from the Community RBS Collection of the Registry of Standard Biological Parts (partsregistry.org) as described by Lassila et al. (J. Mol. Biol. 426: 2217 (2014)):

```
        For BMC-H:
                                     (SEQ ID NO: 21)
        TCTAGAGAAAGAGGAGAAATACTAGATG

For BMC-T:
                                     (SEQ ID NO: 22)
        TCTAGAGATTAAAGAGGAGAAATACTAGATG

For BMC-P:
                                     (SEQ ID NO: 23)
        TCTAGAGTCACACAGGAAACCTACTAGATG
```

The full sequence of this synthetic *H. ochraceum* operon has the following sequence (SEQ ID NO:24) with sequences that separate the different microcompartment subunits identified in bold and with underlining.

AATAATTTTGTTTAGAGAAAGAGGAGAAATACTAG
ATGGCGGACGCACTGGGTATGATTGAAGTTCGTGGTTTTGTTGGTATGGT

GGAAGCGGCGGATGCTATGGTGAAAGCGGCTAAAGTTGAACTGATTGGTT

ATGAAAAAACCGGCGGTGGCTACGTGACGGCAGTGGTTCGTGGTGATGTC

GCAGCAGTTAAGGCAGCTACCGAAGCCGGTCAGCGTGCAGCAGAACGTGT

TGGTGAAGTCGTGGCAGTTCATGTCATCCCGCGTCCGCACGTGAACGTTG

ATGCAGCTCTGCCGCTGGGTCGTACGCCGGGTATGGACAAAAGCGCGTAA

TTTAGAGATTAAAGAGGAGAAATACTAG

ATGGACCACGCTCCGGAACGCTTTGATGCGACCCCGCCGGCAGGTGAACC

GGACCGCCCGGCACTGGGTGTGCTGGAACTGACCTCAATTGCTCGTGGTA

TCACCGTTGCGGATGCGGCCCTGAAACGTGCACCGAGTCTGCTGCTGATG

TCCCGCCCGGTCAGCTCTGGCAAGCATCTGCTGATGATGCGTGGCCAGGT

GGCAGAAGTTGAAGAATCAATGATTGCAGCTCGCGAAATCGCTGGTGCAG

GTTCGGGTGCTCTGCTGGATGAACTGGAACTGCCGTATGCGCACGAACAA

CTGTGGCGCTTTCTGGACGCACCGGTGGTTGCAGATGCATGGGAAGAAGA

CACCGAAAGCGTCATTATCGTGGAAACCGCGACGGTGTGCGCGGCCATTG

ATAGTGCCGACGCAGCTCTGAAAACGGCACCGGTCGTGCTGCGTGATATG

CGCCTGGCCATTGGTATCGCTGGCAAGGCGTTTTTCACCCTGACGGGTGA

ACTGGCAGACGTGGAAGCGGCCGCAGAAGTTGTCCGTGAACGTTGCGGTG

CACGTCTGCTGGAACTGGCATGTATCGCACGCCCGGTTGATGAACTGCGT

GGCCGCCTGTTTTTCTAA

TTTAGAGATTAAAGAGGAGAAATACTAG

ATGGAACTGCGTGCTTATACGGTCCTGGATGCCCTGCAGCCGCAACTGGT

CGCCTTTCTGCAAACGGTGTCAACGGGTTTCATGCCGATGGAACAGCAAG

CGAGCGTTCTGGTCGAAATTGCACCGGGTATCGCTGTCAACCAGCTGACC

GACGCAGCACTGAAAGCAACGCGTTGCCAGCCGGGTCTGCAAATTGTGGA

ACGTGCGTATGGCCTGATCGAAATGCATGATGACGATCAGGGTCAAGTTC

GTGCAGCTGGTGACGCAATGCTGGCACACCTGGGTGCACGTGAAGCTGAT

CGTCTGGCACCGCGTGTGGTTAGCTCTCAGATTATCACCGGTATTGACGG

CCATCAGAGTCAACTGATCAACCGTATGCGCCACGGTGATATGATTCAGG

CAGGCCAAACGCTGTATATCCTGGAAGTTCATCCGGCAGGTTACGCAGCA

CTGGCAGCTAATGAAGCCGAAAAAGCGGCCCCGATTAAGCTGCTGGAAGT

CGTGACCTTTGGTGCATTCGGTCGTCTGTGGCTGGGTGGTGGTGAAGCAG

AAATCGCAGAAGCAGCTCGTGCGGCAGAAGGTGCACTGGCTGGTCTGTCC

GGCCGTGATAATCGCGGCTAA

TTTAGAGATTAAAGAGGAGAAATACTAG

ATGTCAATCACCCTGCGCACCTATATCTTTCTGGACGCCCTGCAACCGCA

ACTGGCAACCTTCATCGGCAAAACGGCTCGTGGCTTCCTGCCGGTCCCGG

GTCAGGCAAGCCTGTGGGTGGAAATTGCTCCGGGTATTGCGATCAACCGT

GTGACCGATGCGGCCCTGAAAGCTACGAAGGTGCAGCCGGCGGTTCAAGT

GGTTGAACGCGCGTATGGCCTGCTGGAAGTTCATCACTTCGATCAGGGCG

AAGTCCTGGCAGCTGGTAGTACCATCCTGGACAAACTGGAAGTTCGTGAA

-continued
GAAGGTCGCCTGAAGCCGCAGGTGATGACCCATCAAATTATCCGTGCTGT

TGAAGCGTATCAGACGCAAATTATCAACCGCAATAGTCAGGGCATGATGA

TTCTGCCGGGTGAATCCCTGTTTATCCTGGAAACCCAACCGGCAGGTTAC

GCAGTCCTGGCAGCCAATGAAGCCGAAAAAGCAGCTAACGTTCACCTGGT

CAATGTGACGCCGTATGGCGCATTCGGTCGTCTGTACCTGGCCGGCTCAG

AAGCAGAAATTGATGCGGCCGCAGAAGCTGCGGAAGCCGCAATCCGCAGC

GTTTCTGGTGTCGCGCAGGAATCGTTTCGTGACCGCTAA

TTTAGAGTCACACAGGAAACCTACTAG

ATGTATCTGGGTCGTGTGATTGGTACCGTGGTGGCTGAACGCAAAGTGGC

GGGICTGGAAGGCGCAAAACTGCTGCTGGTGCAACCGCTGGATGACGCAC

TGAGTCCGGTCGGTGGTGTGCAGGCAGCAGTTGATACCGTCCAAGCAGGT

CCGGATGACCTGGTGTATCTGGTTGGTAGCCGTGAAGCAGCTCTGGCGCT

GACGCCGTCTTTTGTGCCGGTTGATGCGGCCATTGTCGGCATCGTTGATG

ACGTGCATGCACCGGAACGCGCTAGCTAA

The microcompartment shell subunits can have sequence variations. For example, the bacterial microcompartment subunits used to generate the microcompartments can have at least 30%, at least 40%, at least 50%, 60%, at least 70%, or at least 75%, or at least 80%, or at least 85%, or at least 90%, or at least 95%, or at least 97% sequence identity to any of SEQ ID NO: 1-20 or 24, especially in the aligned region of the PFAM00936 domain.

For example, a related BMC sequence is available from *Deltaproteobacteria bacterium* CG2_30_63_29 (SEQ ID NO:36) has at least 42% sequence identity to SEQ ID NO: 1, as illustrated below, where the amino acids at positions corresponding to the 55, 56 and 154 positions of the SEQ ID NO:1 protein are highlighted in the *Deltaproteobacteria bacterium* protein. These amino acids can be modified. For example, the *Deltaproteobacteria bacterium* can have cysteines at the positions corresponding to positions 55 and/or 56; and the *Deltaproteobacteria bacterium* protein can have phenylalanine at the position corresponding to position 154 of the SEQ ID NO: 1 protein.

```
SEQ: 1    21 ALGVLELTSIARGITVADAALKRAPSLLLMSRPVSSGKHLLMMRGQVAEVEESMIAAREI
             ****  **   * **  * **  ** *         *** **  *   * **** * * * *
SEQ: 18   18 ALGVIELGTIIRGYRVLDAMVKRSPITVRAAYPVSTGKFLIFVEGGVAEVDEAMQAGRPA

SEQ: 1    81 AGAGSGALLDELELPYAHEQLW-----RFLDAPVVADAWEEDTESVIIVETATVCAAIDS
              **     **  * ***  * ***      *    *                  *   **  **
SEQ: 18   78 AG---NQLLADLFLPYCHPQLWDGLFQKFKRTPI---------DALGLFECHTVVDAILG

SEQ: 1   136 ADAALKTAPVVLRDMRLAIGIAGKAFFTLTGELADVEAAAEVVRERCG-ARLLELACIAR
              ** ***  *  *  *       ** **  * *  *   *** * ***  *    *    * *
SEQ: 18  126 ADVALKAAEVNLAALHLAAGIGGRAYFVVSGELFDAEAAIEAALDRIDEPRIIEHDVLCA

SEQ: 1   195 PVDEL 199
              *  *
SEQ: 18  186 PHDDM 190
```

-continued
TTTAGAGTCACACAGGAAACCTACTAG

ATGCGTCTGTGTCGTGTTCTGGGCTCCGTCGTCGCCACCGTCAAGCACCC

GGTCTACAATGGTCTGCCGCTGATGATCGTTCAACCGCTGGATGACGCAG

GTCGTGATGCAGGCGCTAGTTTTCTGGCTGTTGATAACGTCCAGTCCGGT

CCGGGTGACCGTGTCCTGGTGCTGACCGAAGGTGGTGGTGTGCGTCAGAT

TCTGGCACTGGGTGATCAAGTCCCGATTCGCAGCCTGATCGTGGGCGTGG

TTGATGCAGTGGACGGTGTTGCAGCAACGGGTGTTGATGACGCAGGTGGT

GCAGCTGATAGCGCAGCAGCAGCTAAATCTGTCCGTGCAGATGAACTGCC

GGCAGACGCAAGCGCGGCCGGTCGCGGCGAATAA

TTTAGAGTCACACAGAAACCTACTAG

ATGGTCCTGGGTAAAGTCGTGGGTACGGTGGTGGCGAGCCGCAAAGAACC

GCGCATTGAAGGTCTGAGCCTGCTGCTGGTCCGTGCCTGCGATCCGGACG

GTACCCCGACGGGTGGTGCAGTGGTTTGTGCAGATGCAGTGGGTGCAGGT

GTTGGTGAAGTCGTGCTGTATGCGAGTGGCAGCTCTGCCCGTCAGACCGA

AGTCACGAACAATCGCCCGGTTGATGCAACCATTATGGCTATCGTTGACC

TGGTCGAAATGGGCGGTGATGTGCGTTTTCGCAAAGACTAA

The *Deltaproteobacteria bacterium* protein is available as accession number OIP31652.1 from the NCBI database, and the sequence of this protein is shown below as SEQ ID NO: 36, with the amino acids that can be modified highlighted.

```
  1 MPNDLRHIGN GDSAPSEALG VIELGTIIRG YRVLDAMVKR
 41 SPITVRAAYP VSTGKFLIFV EGGVAEVDEA MQAGRPAAGN
 81 QLLADLFLPY CHPQLWDGLF QKFKRTPIDA LGLFECHTVV
121 DAILGADVAL KAAEVNLAAL HLAAGIGGRA YFVVSGELFD
161 AEAAIEAALD RIDEPRIIEH DVLCAPHDDM TLELLGLQTV
201 HEKY
```

Another example of a related BMC sequence is available from *Hyalangium minutum* that has at least 49% sequence identity to SEQ ID NO: 1, as illustrated below, where the amino acids at positions corresponding to the 55, 56 and 154 positions of the SEQ ID NO: 1 protein are highlighted in the *Hyalangium minutum* protein. These amino acids can be modified. For example, the *Hyalangium minutum* can have cysteines at the positions corresponding to positions 55 and/or 56; and the *Hyalangium minutum* protein can have phenylalanine at the position corresponding to position 154 of the SEQ ID NO:1 protein.

```
SEQ 1    20 PALGVLELTSIARGITVADAALKRAPSLLLMSRPVSSGKHLLMMRGQVAEVEESMIAARE
            *** *** ***** ****  ****  * *  *  ** **   * **** **        *
SEQ37    10 PALALLELDSIARGYVVADAVVKRAPVTLAMAEAVTPGKYLLLFSGGVAEVQESFQEGLE

SEQ 1    80 IAGAGSGALLDELELPYAHEQLWRFLDAPVVADAWEEDTESVIIVETATVCAAIDSADAA
             +AG    LLD+L LP A + L   L              ESV IVET TV AA+  AD A
SEQ37    70 VAGR---TLLDKLLLPMAADGLVAGLQGRFPGTFG----ESVGIVETHTVAAALLCADTA

SEQ 1   140 LKTAPVVLRDMRLAIGIAGKAFFTLTGELADVEAAAEVVRERCGAR-LLELACIARPVDE
            ** * ***   ** ** **  * * ***  ****  *          **   ** *
SEQ37   123 LKRAEVVLERLQLARGIGGKGVFVLAGELHMVEAALEGAAAAVEPHLLLTTEIIQRPSPE

SEQ 1   199 LRGRLF 204
            ****
SEQ37   183 LRGRVL 188
```

The *Hyalangium minutum* protein is available as accession number KFE69389.1 from the NCBI database, and the sequence of this protein is shown below as SEQ ID NO: 37, with the amino acids that can be modified highlighted.

```
  1 MSDPLPLPGP ALALLELDSI ARGYVVADAV VKRAPVTLAM

41 AEAVTPGKYL LLFSGGVAEV QESFQEGLEV AGRTLLDKLL

61 LPMAADGLVA GLQGRFPGTF GESVGIVETH TVAAALLCAD

121 TALKRAEVVL ERLQLARGIG GKGVFVLAGE LHMVEAALEG

161 AAAAVEPHLL LTTEIIQRPS PELRGRVL
```

Such alignments illustrate that a variety of BMC proteins can be modified to have cysteines at the positions corresponding to positions 55 and/or 56 of the SEQ ID NO: 1 protein; and/or a phenylalanine at the position corresponding to position 154 of the SEQ ID NO: 1 protein. These modified BMC proteins can also incorporate iron (e.g., [4Fe-4S] clusters) in the manner illustrated herein.

Additional Components

Bacterial microcompartments (BMCs) are polyhedral organelles (typically 40-200 nm in diameter) consisting of a proteinaceous shell that can enclose a multi-enzyme core (recently reviewed by Kerfeld & Erbilgin, *Trends Microbiol.* 2015, 23: 22 (2015); and Bobik et al., *Mol. Microbiol* 98: 193 (2015)). While all types of BMCs share an architecturally similar shell, the encapsulated enzymes can vary, contributing to the remarkable functional and phylogenetic diversity of BMCs (Axen et al., *PLoS Comput. Biol.* 10: e1003898 (2014)).

Bacterial microcompartments can serve as nanobiocatalytic sites and reactors in vivo or in vitro. The modified bacterial microcompartments serving as nanobiocatalytic sites can include one or more enzymes within them that can catalyze various reactions. The enzymes can naturally be encapsulated within the microcompartments, or the enzymes can be tethered to one or more of the subunits of the microcompartments. Examples of enzymes that can be encapsulated or tethered within the modified microcompartments can include nitrogenases, enzymes of the methyl-erythritol 4-phosphate (MEP) pathway MEP pathway (e.g., IspG and IspH), and/or enzymes that can catalyze the conversion of NAD/NADP.

In some cases, the modified bacterial microcompartments can include one or more nitrogenases, for example, to improve nitrogen fixation. Nitrogenases can reduce nitrogen ($N_2$) to $NH_3$ via nitrogen fixation and are found in certain bacteria (such as cyanobacteria). Nitrogenase typically consists of two proteins that work in tandem: the iron (Fe) protein and the molybdenum-iron (MoFe) protein. During the catalytic reduction of nitrogen, the electrons are transferred from the Fe-protein to the MoFe-protein.

The iron protein component of nitrogenase accepts the electrons, typically from a flavodoxin or a ferredoxin, and transfers them further to the MoFe-protein. This electron transfer can be enabled in some cases by simultaneous hydrolysis of ATP to ADP.

An example of a sequence for a nitrogenase Fe-protein from *Rhizobium phaseoli* is available from the UniProt database as accession number A0A192TMU2, and provided below as SEQ ID NO:26.

```
            10         20         30         40
    MSDLRQIAFY GKGGIGKSTT SQNTLAALVD LGQKILIVGC 50         60         70         80
    DPKADSTRLI LNAKAQDTVL HLAAQEGSVE DLELEDVLKA 90        100        110        120
    GYKGIKCVES GGPEPGVGCA GRGVITSINF LEENGAYDDV 130        140        150        160
    DYVSYDVLGD VVCGGFAMPI RENKAQEIYI VMSGEMMALY 170        180        190        200
    AANNIAKGIL KYAHSGGVRL GGLICNERQT DRELDLSEAL 210        220        230        240
    AARLNSKLIH FVPRDNIVQH AELRKMTVIQ YAPDSKQAGE 250        260        270        280
    YRALAEKIHA NSGQGTIPTP ITMEELEDML LDFGIMKSDE

290
    QMLAELQAKE SAVVAAQ
```

An example of a sequence for a nitrogenase Fe-protein from *Bacteroidales bacterium* Barb6XT is available from the UniProt database as accession number A0A180F7Y. and provided below as SEQ ID NO:27.

```
            10         20         30         40
    MSKKIKQIAV YGKGGIGKST TTSNISAALV EAGHKVLQFG 50         60         70         80
    CDPKSDSTNT LRDGKYIPTV LDLLREKPKV DAHEAIFQGF 90        100        110        120
    KGVYCVEAGG PAPGVGCAGR GIITAVELLK SQHIFEELDL 130        140        150        160
    DYVIYDVLGD VVCGGFAVPI REGIAEHVFT VSSSDFMSIY 170        180        190        200
    AANNLMKGIK KYSNSGGALF GGIIANSINS SYQRAIIDDF
```

-continued

```
            210         220         230         240
    TQQTGTQVVE  YVPRSITVTQ  AELSGRTTIE  AQPISVQADI 250         260         270         280
    YRSLAKKIHE  HTESRVPTPL  EIDALREWSA  RWADQLLAIE

290
    AGEVRGTQAG  I
```

A comparison of the sequences of the *Rhizobium phaseoli* nitrogenase Fe-protein with SEQ ID NO:26 and the *Bacteroidales bacterium* Barb6XT nitrogenase Fe-protein with SEQ ID NO:27 is shown below.

```
46.1% identity in 267 residues overlap; Score: 603.0; Gap frequency: 2.2%
Rhizobium    4 LRQIAFYGKGGIGKSTTSQNTLAALVDLGQKILIVGCDPKADSTRLILNAKAQDTVLHLA
Bacteroid    5 IKQIAVYGKGGIGKSTTTSNISAALVEAGHKVLQFGCDPKSDSTNTLRDGKYIPTVLDLL
               ***  ********** *  ****   * *  ***** ***        *   ***  *

Rhizobium   64 AQEGSVEDLELEDVLKAGYKGIKCVESGGPEPGVGCAGRGVITSINFLEENGAYD--DVD
Bacteroid   65 REKPKVD---AHEAIFQGFKGVYCVEAGGPAPGVGCAGRGIITAVELLKSQHIFEELDLD
                        *    * **  *** *** ********** **    *        * *

Rhizobium  122 YVSYDVLGDVVCGGFAMPIRENKAQEIYIVMSGEMMALYAANNIAKGILKYAHSGGVRLG
Bacteroid  122 YVIYDVLGDVVCGGFAVPIREGIAEHVFTVSSSDFMSIYAANNLMKGIKKYSNSGGALFG
               ** ************ ****   *   * *   *  * ***** ****  *  ***  *

Rhizobium  182 GLICNERQTDRELDLSEALAARLNSKLIHFVPRDNIVQHAELRKMTVIQYAPDSKQAGEY
Bacteroid  182 GIIANSINSSYQRAIIDDFTQQTGTQVVEYVPRSITVTQAELSGRTTIEAQPISVQADIY
               * * *               *             ***   * *    * *  *  *  *

Rhizobium  242 RALAEKIHANSGQGTIPTPITMEELED
Bacteroid  242 RSLAKKIHEHT-ESRVPTPLEIDALRE
                * ** ***       *** *
```

Such a comparison of amino acid sequences illustrates what are the conserved and non-conserved regions of these proteins, allowing those of skill in the art to identity regions or amino acids that can be changed without adversely affecting the structure and activities of the proteins. Such a comparison can also illuminate which amino acids may serve as linkage sites for tethering the proteins to one or more microcompartment subunits.

An example of a sequence for a nitrogenase molybdenum-iron (MoFe) protein from *Gluconacetobacter diazotrophicus* is available from the UniProt database as accession number A9H5W8, and provided below as SEQ ID NO:28.

```
            10          20          30          40
    MPQNVDKILD  HAPLFREPEY  QEMLAGKAKL  ENMPPADKVV 50          60          70          80
    EIADWTKSWE  YREKNFARES  LSVNPAKACQ  PLGAVFVASG 90         100         110         120
    FERTMSFVHG  SQGCVAYYRS  HLSRHFKEPS  SAVSSSMTED 130         140         150         160
    AAVFGGLNNM  VDGLANTYKL  YDPKMIAVST  TCMAEVIGDD 170         180         190         200
    LHAFIQTAKG  KGSVPEEFDV  PFAHTPAFVG  SHVTGYDNML 210         220         230         240
    KGILEHFWKG  RTPVPNRSYN  IIPGFDGFAV  GNNRELKRIL 250         260         270         280
    GMMGVQYTIL  SDVSDQFDTP  SDGEYRMYDG  GTKIEAARDA 290         300         310         320
    VNADYTISLQ  EYCTPKTLEY  CQSFGQKTAS  FHYPLGIGAT 330         340         350         360
    DDLLQKLSEI  SGKPVPQELE  MERGRLVDAL  ADSQAYLHGK 370         380         390         400
    TYAIYGDPDF  VYGMARFILE  TGGEPKHCLA  TNGSKAWEAQ 410         420         430         440
    MQELFDSSPF  GVGCKAWGGK  DLWHMRSLLA  TEKVDLLIGN 450         460         470         480
    SYGKYLERDT  DTPLIRLMFP  IFDRHHHHRF  PVWGYQGALR 490         500         510
    VLVTLLDKIF  DKLDDDTTQA  GVTDYSFDLT  R
```

An example of a sequence for a nitrogenase molybdenum-iron (MoFe) protein from *Bacteroidales bacterium* Barb6XT is available from the UniProt database as accession number A0A180F7W2 and provided below as SEQ ID NO:29.

```
            10          20          30          40
    MLLRHTTAQE  IERKALTINP  AKTCQPVGAM  YAALGLHGCL 50          60          70          80
    PHSHGSQGCC  SYHRSALTRH  FKEPVMAATS  SFSEGSSVFG 90         100         110         120
    GSANLVTATE  TIFTVYNPDV  VAVHTTCLSE  TIGDDLTQIV 130         140         150         160
    SKAHEDGLVP  EGKKVIYCNT  PSYVGTHVTG  YSNQVAAFVK 170         180         190         200
    FFSTATPKKK  NVVNLVAGWM  EPSDMREIKR  LAQEMEARII 210         220         230         240
    LFPDMSGVLD  APLTGKFEMY  PKGGTTQAQL  IATGDSKFTI 250         260         270         280
    GLGAYTTEDA  CVKLENKCKV  KFEVVEIPIG  LKATDRFITS 290         300         310         320
    LSRHANVPVP  DSITEERGRL  VDLIADNSKY  FYGKRVALFG 330         340         350         360
    DPDTLIPLTE  FLLTLDMKPV  YIVTGTPGKH  FDESMKTLLS
```

```
              370         380         390         400
     EKVPEAKYKS GPNADMFQLH QWIKQEPVDL LIGNTYGKYI 410         420         430         440
     ARDENIPFVR LGFPIVDRAG HNYFPNTGYV GATNLVIKIL 450         460
     EKELDHLDRN CPDEKVEWQL
```

A comparison of the sequences of the *Gluconacetobacter diazotrophicus* nitrogenase molybdenum-iron (MoFe) protein with SEQ ID NO:28 and the *Bacteroidales bacterium* Barb6XT nitrogenase molybdenum-iron (MoFe) protein with SEQ ID NO:29 is shown below.

```
37.4% identity in 439 residues overlap; Score: 765.0; Gap frequency: 1.1%
Gluconace  58 RESLSVNPAKACQPLGAVFVASGFERTMSFVHGSQGCVAYYRSHLSRHFKEPSSAVSSSM
Bacteroid  13 RKALTINPAKTCQPVGAMYAALGLHGCLPHSHGSQGCCSYHRSALTRHFKEPVMAATSSF
                *  * **** *** **     * *        ******  * ** * ******    * **

Gluconace 118 TEDAAVFGGLNNMVDGLANTYKLYDPKMIAVSTTCMAEVIGDDLHAFIQTAKGKGSVPEE
Bacteroid  73 SEGSSVFGGSANLVTAIETIFTVYNPDVVAVHTTCLSETIGDDLTQIVSKAHEDGLVPEG
                 * ****  *  *      *  * *  ** *** * ****      *  * ***

Gluconace 178 FDVPFAHTPAFVGSHVTGYDNMLKGILEHFWKGRTPVPNRSVNIIPGFDGFAVGNNRELK
Bacteroid 133 KKVIYCNTPSYVGTHVTGYSNQVAAFVK-FFSTATPKKKNVVNLVAGW--MEPSDMREIK
                 *   ** ** *****  *      *     * **         **   *         ** *

Gluconace 238 RILGMMGVQYTILSDVSDQFDTPSDGEYRMYDGGTKIEAARDAV-NADYTISLQEYCTPK
Bacteroid 190 RLAQEMEARIILFPDMSGVLDAPLTGKFEMYPKGGTTQAQLIATGDSKFTIGLGAYTTED
                * *        ** *  * *  **       * *       **  * * *

Gluconace 297 TLEYCQSFGQ-KTASFHYPLGIGATDDLLQKLSEISGKPVPQELEMERGRLVDALADSQA
Bacteroid 250 ACVKLENKCKVKFEVVEIPIGLKATDRFITSLSRHANVPVPDSITEERGRLVDLIADNSK
                    *    * ***    **    ***       *******  **

Gluconace 356 YLHGKTYAIYGDPDFVYGMARFILETGGEPKHCLATNGSKAWEAQMQELFDSSPFGVGCK
Bacteroid 310 YFYGKRVALFGDPDTLIPLTEFLLTLDMKPVYIVTGTPGKHFDESMKTLLSEKVPEAKYK
               * **  *   ****      * *    *        *      * *            *

Gluconace 416 AWGGKDLWHMRSLLATEKVDLLIGNSYGKYLERDTDTPLIRLMFPIFDRHHHHRFPVWGY
Bacteroid 370 SGPNADMFQLHQWIKQEPVDLLIGNTYGKYIARDENIPFVRLGFPIVDRAGHNYFPNTGY
                *              * ******* **** **  *   ** ***  **  *    ** **

Gluconace 476 QGALRVLVTLLDKIFDKLD
Bacteroid 430 VGATNLVIKILEKELDHLD
               **        * *  * **
```

Such a comparison of amino acid sequences illustrates what are the conserved and non-conserved regions of these proteins, allowing those of skill in the art to identity regions or amino acids that can be changed without adversely affecting the structure and activities of the proteins. Such a comparison, combined with structural modeling, can also illuminate which amino acids may serve as linkage sites for tethering the proteins to one or more microcompartment subunits.

The modified bacterial microcompartments can also encapsulate one or more enzymes of the methylerythritol 4-phosphate (MEP) pathway MEP pathway (e.g., IspG and IspH) to improve production of the basic building blocks for the biosynthesis of terpenes. Such terpenes include numerous chemicals (more than 55,000 are known) that provide starting materials and intermediates for production of pharmaceuticals, biofuels, fragrances and more. For example, IspG and IspH are enzymes that can use the [4Fe-4S] cluster and the electrons provided for their catalytic activity. IspG and IspH are generally sensitive to oxygen and not very catalytically efficient: encapsulation protects them from oxygen and can improve their efficiency.

An example of a sequence for IspG (4-hydroxy-3-methylbut-2-en-1-yl diphosphate synthase (flavodoxin)) protein from *Streptomyces clavuligerus* is available from the UniProt database as accession number B5GZ64 and provided below as SEQ ID NO:30.

```
              10          20          30          40
     MTAISLGMPS VPTKLADRRV SRKIQVGSVA VGGDAPVSVQ 50          60          70          80
     SMTTTRTSDI GATLQQIAEL TASGCQIVRV ACPTQDDADA 90         100         110         120
     LATIARKSQI PVIADIHFQP KYVFAAIDAG CAAVRVNPGN 130         140         150         160
     IKQFDDKVKE IAKAASASGT PIRIGVNAGS LDARLLKKYG 170         180         190         200
     KATPEALVES ALWEASLFEE HGFQDIKISV KHNDPVVMVN 210         220         230         240
     AYRQLAAQCD YPLHLGVTEA GPAFQGTTKS AVAFGALLSE 250         260         270         280
     GIGDTIRVSL SAPPAEEVKV GIQILESLNL RQRRLEIYSC 290         300         310         320
     PSCGRAQVDV YKLADEVTAG LEGMEVPLRV AVMGCVVNGP 330         340         350         360
     GEAREADLGV ASGNGKGQIF VKGEVIKTVP EAKIVETLIE 370         380
     EAMKIAEEME KAGVMSGEPQ VSIG
```

An example of a sequence for IspG (4-hydroxy-3-methylbut-2-en-1-yl diphosphate synthase (flavodoxin)) protein from *Streptomyces roseus* is available from the UniProt database as accession number A0A0J7AHR0 and provided below as SEQ ID NO:31.

```
                10         20         30         40
       MTAISLGMPA VPTKLADRRV SRKIQYGSVA VGGDSQISVQ 50         60         70         80
       SMTTTRTSDI GATLQQIAEL TASGCDIVRV ACPTQDDADA 90        100        110        120
       LAVIAKKSQI PVIADIHFQP KYVFAAIDAG CAAVRVNPGN 130        140        150        160
       IKQFDDKVKE IARAAKDAGT PIRIGVNAGS LDARLLKKYG 170        180        190        200
       KATPEALVES ALWEASLFEE HGFSDIKISV KHNDPVVMVN 210        220        230        240
       AYRQLAAQCE YPLHLGVTEA GPAFQGTIKS AVAFGALLSE 250        260        270        280
       GIGDTIRVSL SAPPVEEVKV GIQILESLNL KPRRLEIVSC 290        300        310        320
       PSCGRAQVDV YKLAEEVTAG LTGMEVPLRV AVMGCVVNGP 330        340        350        360
       GEAREADLGY ASGNGKGQIF VKGEVIKTVP ESKIVEILIE 370        380
       EAMKIAEQME KDGIASGEPT VAIGV
```

A comparison of the sequences of the *Streptomyces clavuligerus* IspG protein with SEQ ID NO:30 and the *Streptomyces roseus* IspG protein with SEQ ID NO:31 is shown below.

*myces clavuligerus* is available from the UniProt database as accession number B5GTV4 and provided below as SEQ ID NO:32.

```
                10         20         30         40
       MLAAPRGYCA GVDRAVIAVE KALEQYGAPV YVRHEIVHNK 50         60         70         80
       YVVQTLERKG AVFVDKTAEV PEGSIVMFSA HGVAPVVHEE 90        100        110        120
       AARRKLATID ATCPLVTKVH KEAVRFANED YDILLIGHEG 130        140        150        160
       HEEVIGTSGE APDHITLVDG PDDVDKVEVR DESKVVWLSQ 170        180        190        200
       TTLSVDETME TVDRLKEKFP QLISPPSDDI CYATQNRQTA 210        220        230        240
       VKQMGADADL VIVVGSKNSS NSVRLVEVAL GAGARDAHLV 250        260        270        280
       DFAEEIDEAW LEGVATVGLT SGASVPEILV EGVLEWLSQR 290        300        310        320
       GFQDVELVKA AEESITFSLP KELRRDLRAE AAALVERAEA

330
       VAAGSASAHP GSASGA
```

```
93.5% identity in 384 residues overlap; Score: 1809.0; Gap
frequency: 0.0%
clavuli     1 MTAISLGMPSVPTKLADRRVSRKIQVGSVAVGGDAPVSVQSMTTTRTSDIGATLQQIAEL
roseus      1 MTAISLGMPAVPTKLADRRVSRKIQVGSVAVGGDSQISVQSMTTTRTSDIGATLQQIAEL
              *******  ********************* *  *********** ***** clavuli    61 TASGCQIVRVACPTQDDADALATIARKSQIPVIADIHFQPKYVFAAIDAGCAAVRVNPGN
roseus     61 TASGCDIVRVACPTQDDADALAVIAKKSQIPVIADIHFQPKYVFAAIDAGCAAVRVNPGN
              *** ************  ********************************** clavuli   121 IKQFDDKVKEIAKAASASGTPIRIGVNAGSLDARLLKKYGRATPEALVESALWEASLFEE
roseus    121 IKQFDDKVKEIARAAKDAGTPIRIGVNAGSLDARLLKKYGRATPEALVESALWEASLFEE
              **********    ****************************************** clavuli   181 HGFQDIKISVKHNDPVVMVNAYRQLAAQCDYPLHLGVTEAGPAFQGTIKSAVAFGALLSE
roseus    181 HGFSDIKISVKHNDPVVMVNAYRQLAAQCEYPLHLGVTEAGPAFQGTIKSAVAFGALLSE
              * ********************* **************************** clavuli   241 GIGDTIRVSLSAPPAEEVKVGIQILESLNLRQRRLEIVSCPSCGRAQVDVYKLADEVTAG
roseus    241 GIGDTIRVSLSAPPVEEVKVGIQILESLNLKPRRLEIVSCPSCGRAQVDVYKLAEEVTAG
              ************ *********** ****************** *** clavuli   301 LEGMEVPLRVAVMGCVVNGPGEAREADLGVASGNGKGQIFVKGEVIKTVPEAKIVETLIE
roseus    301 LTGMEVPLRVAVMGCVVNGPGEAREADLGVASGNGKGQIFVKGEVIKTVPESKIVETLIE
              * *********************************************** ***** clavuli   361 EAMKIAEEMEKAGVMSGEPQVSIG
roseus    361 EAMKIAEQMEKDGIASGEPTVAIG
              ******* *** * ***** * **
```

Such a comparison of amino acid sequences illustrates what are the conserved and non-conserved regions of these proteins, allowing those of skill in the art to identity regions or amino acids that can be changed without adversely affecting the structure and activities of the proteins. Such a comparison can also illuminate which amino acids may serve as linkage sites for tethering the proteins to one or more microcompartment subunits.

An example of a sequence for IspH (4-hydroxy-3-methylbut-2-enyl diphosphate reductase) protein from *Strepto-*

An example of a sequence for IspH (4-hydroxy-3-methylbut-2-enyl diphosphate reductase) protein from *Streptomyces roseus* is available from the UniProt database as accession number A0A0J7APK8 and provided below as SEQ ID NO:33.

```
                10         20         30         40
       MTAAAPVPAS RRVLLAAPRG YCAGVDRAVI AVEKALEQYG 50         60         70         80
       APVYVRHEIV HNKYVVQTLE RKGAIFVERT EEVPEGSIVM
```

```
                90        100        110        120
          FSAHGVAPVV HEEAARGKLA TIDATCPLVT KVHKEAIRYA 130        140        150        160
          NEDFDILLIG HEGHEEVTGT SGEAPDHITI VDGPHDVEKV 170        180        190        200
          TVRDESKVVW LSQTTLSVDE TMETVDALKT KFPLLVSPPS 210        220        230        240
          DDICYATSNR QAAVKVMGAD SDLVIVVGSK NSSNSIRLVE 250        260        270        280
          VAKDAGARAA HLVDFASEID EAWLEGVSTV GLTSGASVPE 290        300        310        320
          VLVEEVLEWL AARGYADVEI VKTAEESITF SLPKELRRDL

330
          RAEAAELVAE K
```

A comparison of the sequences of the *Streptomyces clavuligerus* IspH protein with SEQ ID NO:32 and the *Streptomyces roseus* IspH protein with SEQ ID NO:33 is shown below.

```
88.6% identity in 315 residues overlap; Score: 1428.0; Gap
frequency: 0.0%
clavul    1 MLAAPRGYCAGVDRAVIAVEKALEQYGAPVYVRHEIVHNKYVVQTLERKGAVFVDKTAEV
roseus   14 LLAAPRGYCAGVDRAVIAVEKALEQYGAPVYVRHEIVHNKYVVQTLERKGAIFVERTEEV
             *******************************************************  * *** clavul   61 PEGSIVMFSAHGVAPVVHEEAARRKLATIDATCPLVTKVHKEAVRFANEDYDILLIGHEG
roseus   74 PEGSIVMFSAHGVAPVVHEEAARGKLATIDATCPLVTKVHKEAIRYANEDFDILLIGHEG
             *********************  ****************  ******* clavul  121 HEEVIGTSGEAPDHITLVDGPDDVDKVEVRDESKVVWLSQTTLSVDETMETVDRLKEKFP
roseus  134 HEEVIGTSGEAPDHITIVDGPHDVEKVTVRDESKVVWLSQTTLSVDETMETVDALKTKFP
             **************    ********************  *** clavul  181 QLISPPSDDICYATQNRQTAVKQMGADADLVIVVGSKNSSNSVRLVEVALGAGARDAHLV
roseus  194 LLVSPPSDDICYATSNRQAAVKVMGADSDLVIVVGSKNSSNSIRLVEVAKDAGARAAHLV
             * ******** * *  ************ **    *  **** clavul  241 DFAEEIDEAWLEGVATVGLTSGASVPEILVEGVLEWLSQRGFQDVELVKAAEESITFSLP
roseus  254 DFASEIDEAWLEGVSTVGLTSGASVPEVLVEEVLEWLAARGYADVEIVKTAEESITESLP
             * ****** ******** * ***      ******* * clavul  301 KELRRDLRAEAAALV
roseus  314 KELRRDLRAEAAELV
             *********** ** **
```

Such a comparison of amino acid sequences illustrates what are the conserved and non-conserved regions of these proteins, allowing those of skill in the art to identity regions or amino acids that can be changed without adversely affecting the structure and activities of the proteins. Such a comparison can also illuminate which amino acids may serve as linkage sites for tethering the proteins to one or more microcompartment subunits.

In another example, the modified bacterial microcompartments can also include enzymes that catalyze NAD/NADP conversions, which can transform the modified microcompartments and/or host cells that have such modified microcompartments into bio-batteries.

For example, host cells can have modified bacterial microcompartments can include NAD kinase, which catalyzes the following reaction:

ATP+NAD⁺=ADP+NADP⁺.

An example of a sequence for a *Haliangium ochraceum* NAD kinase is available from the UniProt database as accession number D0LKF9 and provided below as SEQ ID NO:34.

```
                10         20         30         40
          MQRVGFILKP GQSSNERLLT ELATWVLELG HLPVIAAEDR 50         60         70         80
          PVIQNVVIVP REHIGQEIDM AVVLGGDGTM LGASNLVADQ 90        100        110        120
          GVPVLGINLG RLGFLTPFDL EDAEDAIADA LAGKLRTSER 130        140        150        160
          MRLAVTYTSD GEAPVTRTGL NDAVIHQGAM ARLIEVEAQL 170        180        190        200
          DGDMVSLYRA DGLIIATPTG STAYNLAAGG PIIEPGQRAM 210        220        230        240
          VLTPVCPHSL TNRSLVVPGS SSITIHLDRS ARGVVLTVDG 250        260        270        280
          QWAHSFSPDD EIEIAAAARP LVVFKSDKRY FDILREKLHW 290        300        310
          GARLDRSHEQ IDEAVGRRSG RISTRQDAVS DPDDDD
```

In another example, host cells can have modified bacterial microcompartments can include glycerol-3-phosphate dehydrogenase [NAD(P)+], which catalyzes the following reaction:

sn-glycerol 3-phosphate+NAD(P)⁺→glycerone phosphate+NAD(P)H.

An example of a sequence for a *Haliangium ochraceum* glycerol-3-phosphate dehydrogenase [NAD(P)+] is available from the UniProt database as accession number D0LJH5 and provided below as SEQ ID NO:35.

```
                10         20         30         40
          MAQLSVIGAG SYGTSLALVF AKAGHSVSMW CHEAELAERM 50         60         70         80
          QRTRENDIYL PGFALPPGIS VSSELAEVVD GADIVLGVTP 90        100        110        120
          THAVRKVLGE AAGHLSGSAI VVNCSKGLEE GTLGRVDEIY
```

```
           130        140        150        160
    RDILPPHVYE RAVYLSGPTF AKELAAGLPA ALVVASRDAD 170        180        190        200
    SAASVQHALS TDRLRLYTAP DVVGVLIGGA LKNVVAIAAG 210        220        230        240
    MSDGMGLGLN ARAAIITRGL AELTRLGTHV GADPLTFAGL 250        260        270        280
    SGMGDLVLTC SGDLSRNRQV GLALGAGKKR AEIVAEMRMV 290        300        310        320
    AEGVNTTRVA RALAERLGVE APITEVMHRV LFEDLPASAA

330
    LADLTGRALR SERA
```

Nucleotide segments encoding the subunits of the modified microcompartments and, optionally, the additional enzymes or components for providing nanobiocatalytic functions can be included in one or more expression cassettes or expression vectors. Such expression cassettes or expression vectors can be transformed into a host cell and/or integrated into a host cell's genome. When the subunits of the modified microcompartments and, optionally, the additional enzymes or components for providing nanobiocatalytic functions are inserted into the host cell's genome, the resulting host cells differ from a wild-type cell due to the inserted nucleotide segments.

An expression cassette can be employed that include nucleotide segments encoding the subunits of the modified microcompartments and, optionally, the additional enzymes or components for providing nanobiocatalytic functions, and one or more regulatory expression sequences. The one or more regulatory expression sequences may include a promoter. The one or more regulatory expression sequences may also include a 3' untranslated region such as a termination sequence.

The promoters employed in expression cassettes or expression vectors can be linked to the relevant nucleotide segment(s) directly or alternatively be located in an appropriate position, for example in a vector such that when the relevant polypeptide is inserted the relevant promoter can act on the same. In one embodiment the promoter is located before the encoding portion of the polynucleotide on which it acts, for example a relevant promoter before each encoding portion of polynucleotide. "Before" as used herein is intended to imply that the promoter is located at the 5 prime end in relation to the encoding nucleotide segment.

Promoters regulate gene expression. Promoter regions are typically found in the flanking DNA upstream from the coding sequence in both prokaryotic and eukaryotic cells. A promoter sequence provides for regulation of transcription of the downstream gene sequence and typically includes from about 50 to about 2,000 nucleotide base pairs. Promoter sequences can also contain regulatory sequences such as enhancer sequences that can influence the level of gene expression. Some isolated promoter sequences can provide for gene expression of heterologous DNAs, that is a DNA different from the native or homologous DNA.

The nucleotide segment(s) can be operably linked to a promoter, which provides for expression of mRNA encoding the subunits of the modified microcompartments and, optionally, the additional enzymes or components for providing nanobiocatalytic functions. Nucleotide segment(s) are operably linked to the promoter when it is located downstream from the promoter, so that the promoter is configured to express a protein encoded by the nucleotide segment(s). The promoter employed is typically a promoter functional in bacteria.

In some cases the nucleotide segment(s) encoding the subunits of the modified microcompartments and, optionally, the additional enzymes or components for providing nanobiocatalytic functions are operably linked to a heterologous promoter. A heterologous promoter is a promoter that is not operably linked to the subunits of the modified microcompartments or the additional enzymes or components for providing nanobiocatalytic functions in nature.

Promoter sequences can be strong or weak, or inducible. A strong promoter provides for a high level of gene expression, whereas a weak promoter provides for a very low level of gene expression. An inducible promoter is a promoter that provides for the turning on and off of gene expression in response to an exogenously added agent, or to an environmental or developmental stimulus. For example, expression can be stimulated from an inducible promoter by factors such as alcohol, acetaldehyde, antibiotics (e.g., tetracycline), steroids, metals and other compounds. An environmentally inducible promoter can induce expression of a gene in response to environmental stimuli such as drought, cold, heat, longer exposure to light, or shorter exposure to light. A bacterial promoter such as the $P_{tac}$ promoter can be induced to vary levels of gene expression depending on the level of isothiopropylgalactoside added to the transformed cells. Steroid inducible promoters have also been employed. Dexamethasone-inducible promoters are activated by introduction of dexamethasone to a cell, tissue, cell culture, or tissue culture. The alc promoter system from the filamentous fungi *Aspergillus nidulans* can be induced by alcohol (e.g., ethanol) or acetaldehyde (see. e.g., Schaarschmidt et al., Plant & Cell Physiol 45(11): 1566-77 (2004). The nopaline synthase (nos) promoter is inducible by hydrogen peroxide and/or methyl jasmonate (see, e.g., Sai & An, *Plant Physiol.* 109(4): 1191-97 (1995)). Further examples of suitable promoters include lac, tac, trp, phoA, lpp, Arab, tet and T7.

Nucleotide segment(s) encoding the subunits of the modified microcompartments and, optionally, the additional enzymes or components for providing nanobiocatalytic functions can be combined with a selected promoter by available methods to yield an expression cassette, for example, as described in Sambrook et al. (MOLECULAR CLONING: A LABORATORY MAnnual. Second Edition (Cold Spring Harbor, NY: Cold Spring Harbor Press (1989): MOLECULAR CLONING: A LABORATORY MAnnual. Third Edition (Cold Spring Harbor, NY: Cold Spring Harbor Press (2000)). Briefly, a plasmid containing a promoter such as a T7 promoter can be constructed or obtained (e.g., pET-11 vector). Such plasmids can be constructed to have multiple cloning sites having specificity for different restriction enzymes downstream from the promoter. The nucleotide segment(s) can be subcloned downstream from the promoter using restriction enzymes and positioned to ensure that the nucleotide segment(s) is inserted in proper orientation with respect to the promoter so that the DNA can be expressed. Once the nucleotide segment(s) is operably linked to a promoter, the expression cassette so formed can be subcloned into a plasmid or other vector (e.g., an expression vector).

The expression cassette can also optionally include 3' nontranslated regulatory DNA sequences that act as a signal to terminate transcription and allow for the polyadenylation of the resultant mRNA. Many 3' nontranslated regulatory sequences are already present in plasmids available from commercial sources such as Clontech, Palo Alto, Calif. The 3' nontranslated regulatory sequences can be operably linked to the 3' terminus of the nucleotide segment(s) by standard methods.

In order to improve identification of host cells that include nucleotide segment(s) encoding the subunits of the modified microcompartments (and, optionally, the additional enzymes or components for providing nanobiocatalytic functions), a selectable or screenable marker gene can be employed. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can 'select' for the marker by chemical means, i.e., through the use of a selective agent (e.g., an antibiotic, a visible signal, or the like), or whether marker is simply a trait that one can identify through observation or testing, i.e., by 'screening.'. Many examples of suitable marker genes are known to the art and can be employed in the practice of the invention.

Included within the terms selectable or screenable marker genes are also genes which encode a "secretable marker" whose secretion can be detected as a means of identifying or selecting for transformed cells. Examples include markers which encode a secretable antigen that can be identified by antibody interaction, or secretable enzymes that can be detected by their catalytic activity. Secretable proteins fall into a number of classes, including small, diffusible proteins detectable, e.g., by ELISA.

An expression cassette can also include plasmid DNA. Plasmid vectors include additional DNA sequences that provide for easy selection, amplification, and transformation of the expression cassette in prokaryotic and eukaryotic cells, e.g., pUC-derived vectors such as pUC8, pUC9, pUC18, pUC19, pUC23, pUC119, and pUC120, pSK-derived vectors, pGEM-derived vectors, pSP-derived vectors, or pBS-derived vectors. The additional DNA sequences include origins of replication to provide for autonomous replication of the vector, additional selectable marker genes (e.g., antibiotic), unique multiple cloning sites providing for multiple sites to insert DNA sequences or genes encoded in the expression cassette and sequences that enhance transformation of prokaryotic and eukaryotic cells.

Expression cassettes and/or vectors that include nucleotide segment(s) encoding the subunits of the modified microcompartments (and, optionally, the additional enzymes or components for providing nanobiocatalytic functions) can be introduced into host cells by a variety of methods. For example, such expression cassettes and/or vectors can be introduced into a recipient cell to create a transformed cell by available procedures. It is likely that not all recipient cells receiving DNA segments or sequences will result in a transformed cell wherein the DNA is stably integrated into the host cell genome and/or expressed.

The host cell can be any type of prokaryotic or eukaryotic cell. In some cases, the host cell is a prokaryotic cell, for example, a bacterial cell. Examples of host cells that can be employed include *Haliangium ochraceum* or *Escherichia coli*.

Properties of Bacterial Shell Proteins and/or Microcompartments

As described herein, a BMC shell protein that was naturally devoid of any cofactor was used as a template for structure-based rational design of a [4Fe-4S] cluster-binding site. As illustrated by a combination of structural and spectroscopic techniques, the assembly of the cluster in the engineered protein is efficient and specific; at least 72-74% of the proteins bind a [4Fe-4S] cluster, and no other forms of the cluster were detected. The cluster and the ligating cysteine residues are hydrogen-bonded to the main chain of the protein. These interactions likely contribute to the stability of the [4Fe-4S] cluster, and facilitate its redox reversibility. For example, in some cases even when the encapsulated [4Fe-4S] cluster is exposed to solvent, it is relatively resistant to stresses such as high temperature or high concentrations of urea. Significantly, the encapsulated cluster exhibits redox and spectroscopic characteristics of [4Fe-4S] clusters found in low-potential bacterial ferredoxins. The structural data reveals a binding mode reminiscent of those found in diverse classes of enzymes with only three irons coordinated by cysteine residues.

BMC-T1-S55C provides a means for achieving electron transfer across the shell of BMCs and allows new functionalities to be usefully incorporated into BMCs, including tailor-made encapsulated oxidoreductive pathways.

Figure 4B:
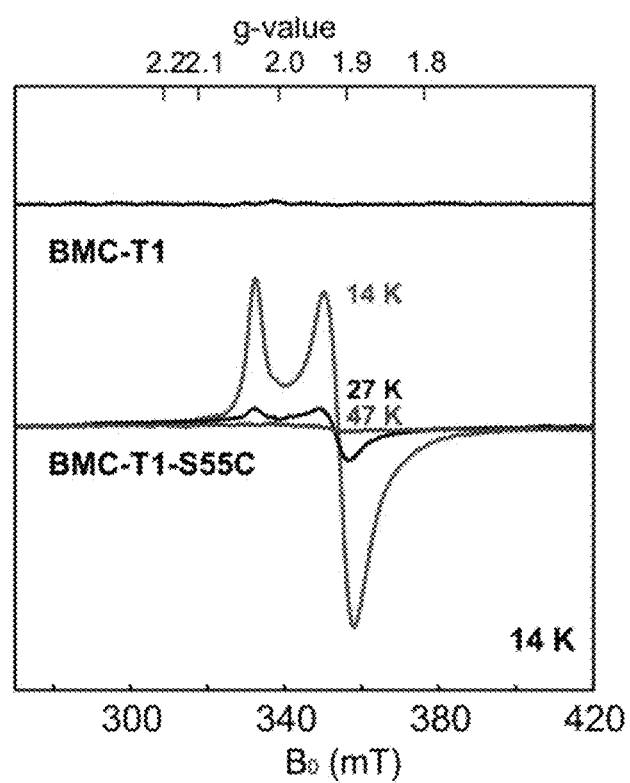
Figure 5A:
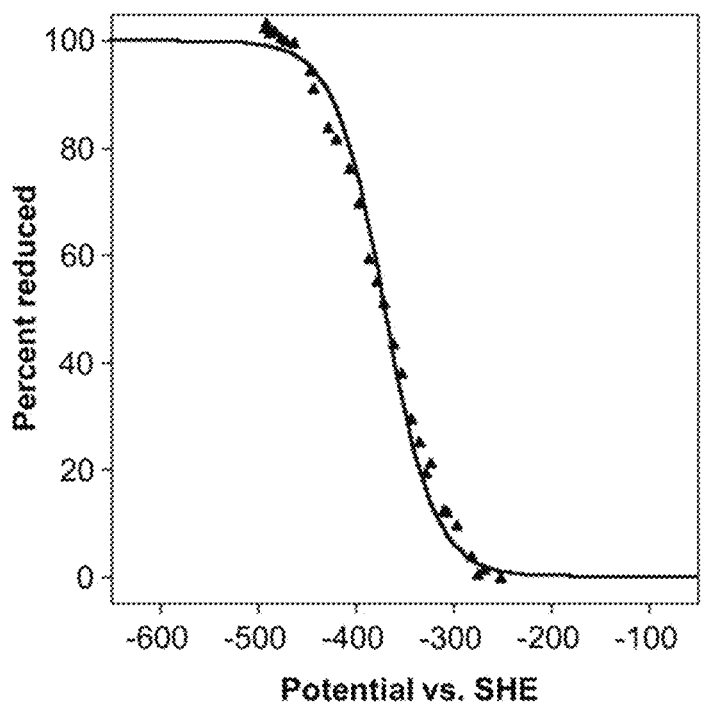
FIGS. 5A-5B illustrate reduction potential of the BMC-T1-S55C [4Fe-4S] cluster by spectroelectrochemistry and redox reversibility.

The data reported herein is the first structural evidence for the successful design of a binding site for a [4Fe-4S] cluster into a protein scaffold, specifically a constituent shell protein of a bacterial organelle. Using a structure-guided approach, the pore of BMC-T1 was re-engineered to selectively incorporate a [4Fe-4S] cluster. Mononuclear Fe, and [2Fe-2S] or [3Fe-4S] clusters were not observed as demonstrated by spectroscopic and structural characterization. The [4Fe-4S] cluster exhibits EPR and redox properties reminiscent of those in low-potential bacterial ferredoxins (FIGS. 4B and 5A).

The BMC-T1-S55C monomer scaffold is composed of two domains which have complementary roles: the first domain harbors the [4Fe-4S] cluster-binding site (Cys55), while residues within the second domain (Gly155 and Ala157) provide hydrogen bonding interactions that most likely stabilizes the [4Fe-4S] cluster and facilitates its redox reversibility. In most [Fe—S] cluster proteins, the cluster ligands are on the same polypeptide chain; in contrast, each BMC-T1-S55C protomer contributes one-third of the [4Fe-4S] cluster binding site, which is completed by the trimerization. Three cysteinate ligands are sufficient for [4Fe-4S] incorporation. The fourth ligand can vary; for example, in radical SAM enzymes, when SAM is present it is the fourth ligand. Similarly to activated aconitase and other dehydratase enzymes, a water molecule (or hydroxide ion) completes the primary coordination sphere of the cluster in BMC-T1-S55C (FIG. 3B). Therefore, the [4Fe-4S] cluster of BMC-T1-S55C can be considered a hybrid between clusters found in low-potential bacterial ferredoxins (redox and spectroscopic characteristics) and those found in different classes of enzymes (architecture of the cluster).

The reduction potential value of −370 mV at pH 7.5 (FIG. 5A) is at the more positive end of the range of −374 to −500 mV reported for bacterial ferredoxins (Rouault, T. *Iron-Sulfur Clusters in Chemistry and Biology*; De Gruyter: Berlin, 2014) but is well within the range of −700 to +100 mV reported for $[4Fe-4S]^{2+/+}$ clusters for other [Fe—S] cluster proteins (Johnson, M. K.; Smith, A. D. In *Encyclopedia of Inorganic and Bioinorganic Chemistry*; John Wiley & Sons, Ltd: Online, 2011). In comparison to other designed [4Fe-4S] proteins, the reduction potential of BMC-T1-S55C is comparable to the value of −350 mV (at pH 8) reported for the minimal ferredoxin maquette (Gibney et al *Proc. Natl. Acad. Sci. U.S.A.* 93: 15041 (1996)) but is significantly more positive than the value reported for the DSD-Fdm (Domain-Swapped Dimer-Ferredoxin maquette) of −479 mV (at pH 7.5) (Roy et al. *Am. Chem. Soc.* 136: 17343 (2014)), as well as the minimal photosystem I $F_A$- and $F_B$-maquettes of −440 mV and −470 mV (at pH 8.3), respectively (Antonkine et al. *Biochim. Biophys. Acta* 1787: 995 (2009). The similarity of the reduction potential between BMC-T1-S55C and the minimalist ferredoxin maquette may reflect the degree of solvent exposure of the clusters in both systems, whereas the more negative potential of DSM-Fdm may be due, at least in part, to the burial of the cluster in the hydrophobic core of its three-helix bundle scaffold.

Notably, the reduction potential of BMC-T1-S55C is much lower than the value determined for the [4Fe-4S] cluster of PduT from *C. freundii*, +99 mV (at pH 7) (Parsons et al. *J. Biol. Chem.* 283: 14366 (2008)). This demonstrates that BMC shell proteins can incorporate [4Fe-4S] clusters with a wide range of reduction potentials, indicating that modifying the environment of the cluster will allow the fine-tuning of the reduction potential of the BMC-T1-S55C [4Fe-4S] cluster to the requirements of the BMC-encapsulated enzymes.

Figure 5B:
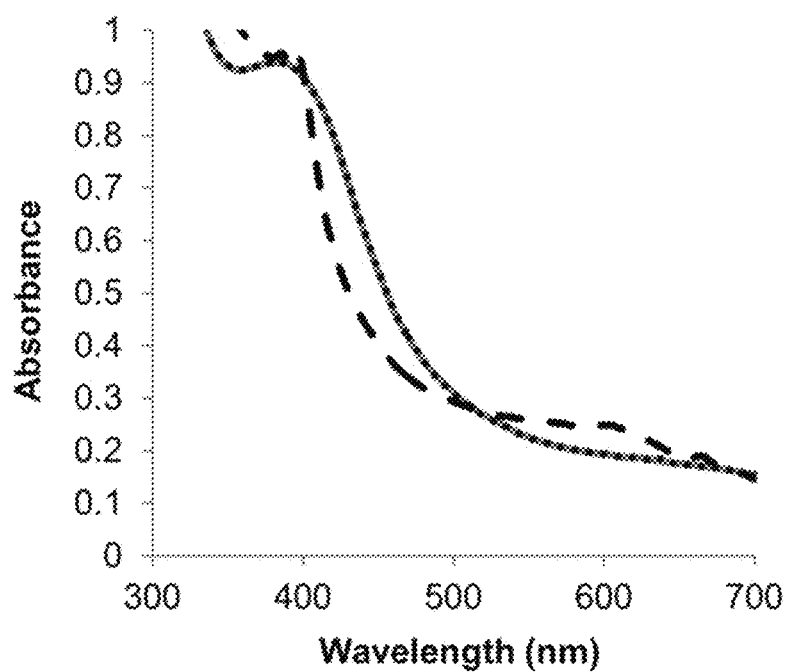

The capacity of the BMC-T1-S55C cluster to function as an electron relay is illustrated by its ability to cycle between oxidized and reduced states without being degraded or oxidatively damaged (FIG. 5B). This is in contrast to other designed [4Fe-4S] cluster proteins in which the reduced state is unstable and irreversible (Grzyb et al. *Biochim. Biophys. Acta* 1797, 406 (2010)).

Hydrogen bonding plays a role in folding and stability of proteins, and influences the properties of metal centers. The installation of a hydrogen bond network is an important consideration in metalloprotein design. The presence of second shell hydrogen bond interactions between backbone amides (Gly155) and the thiolate ligands of Cys55 (FIG. 3B) likely confers stability to the BMC-T1-S55C [4Fe-4S] cluster upon redox cycles. The presence of the hydrogen bond network in the BMC-T1 scaffold which stabilizes the metal center is an important component of the design. The robustness of the cluster is also illustrated by its resistance to different stressors. For example, BMC-T1-S55C retains a significant amount of intact bound [4Fe-4S] cluster after incubation at 55° C. is used as a first purification step. Characterization of the stability of the trimer with and without the cluster, shows that the holoprotein is more stable in urea than the apoprotein (FIG. 6A-6D).

Figure 6E:
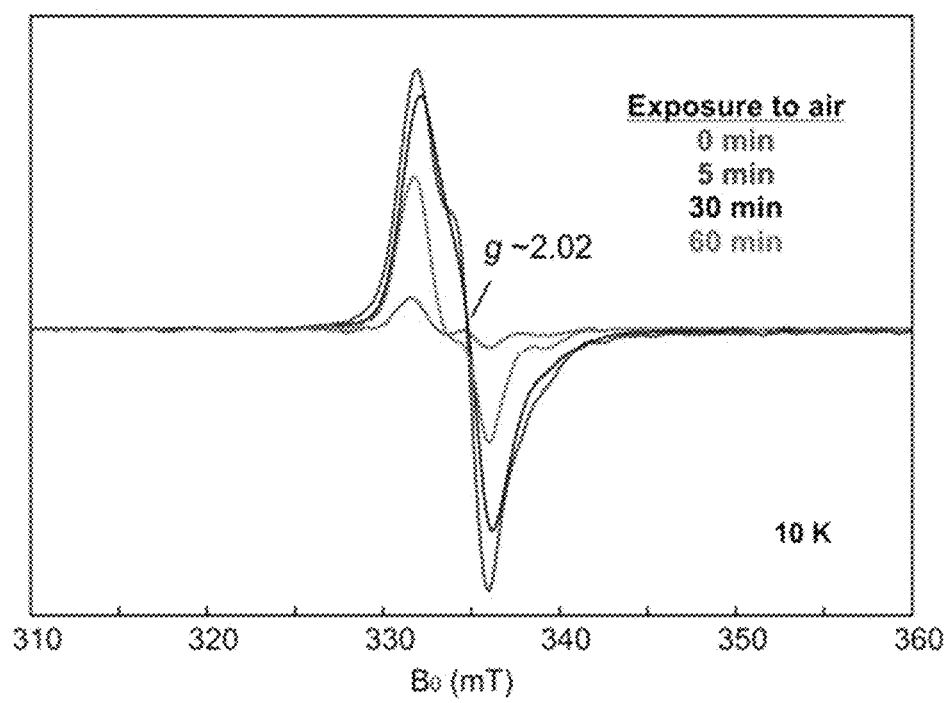
Figure 6F:
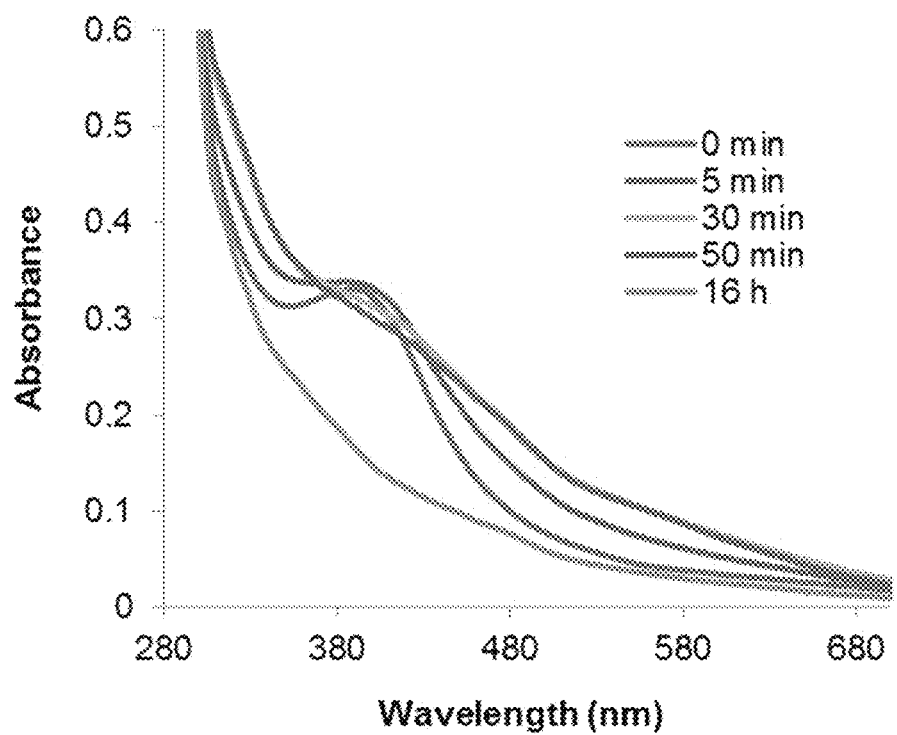

The BMC-T1-S55C cluster seems somewhat tolerant to oxygen. Indeed, initial purifications of BMC-T1-S55C were performed under aerobic conditions from aerobically grown cultures. The purified protein retained a brown color for a few weeks at 4° C. without bleaching of the chromophore or any precipitation. Another indication of oxygen tolerance is the presence of the intact cluster in the BMC-T1-S55C structure, even though preparing the crystals for data collection required brief exposure to aerobic conditions. However, a combination of UV-Vis and EPR spectroscopies suggests that the degradation of the cluster to a [3Fe-4S] form may start shortly after oxygen exposure and can continue over time. The [3Fe-4S] is in turn converted to a more stable [2Fe-2S] form (FIG. 6E-6F). In the crystals, during the brief subjection to aerobic conditions prior to data collection, surface proteins likely may come into contact with oxygen. However, clusters deeper in the crystal are relatively shielded by other proteins as well as the solvent environment, and so their metal centers are less prone to degradation.

To date, there is only a single report of the successful incorporation of a [4Fe-4S] cluster into a natural protein normally devoid of any cofactors, but the electrochemistry of that cluster demonstrates that it is a high potential iron-sulfur protein accessing the [4Fe-4S]$^{3+/2+}$ couple (Coldren et al. *Proc. Natl. Acad. Sci. U.S.A.* 94: 6635 (1997). Moreover, there has been no structural evidence for the success of any of the [4Fe-4S] protein designs described above. The ability to transfer electrons into and out of BMC shells opens a new frontier in their applications in synthetic biology.

Figure 8B:
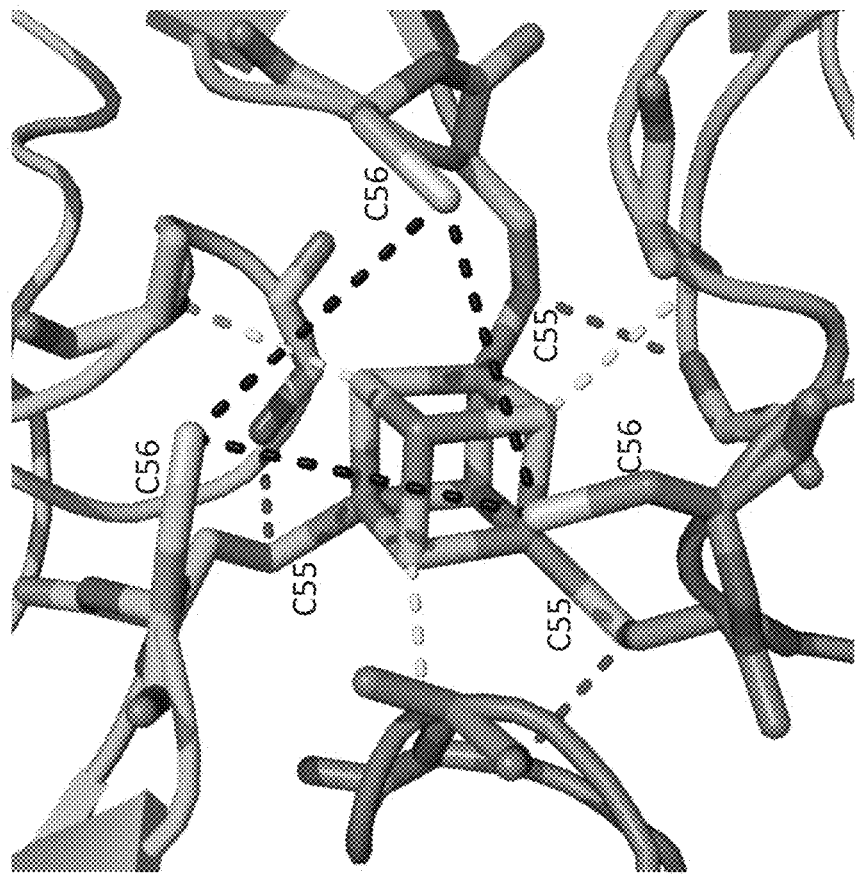
Figure 8A:
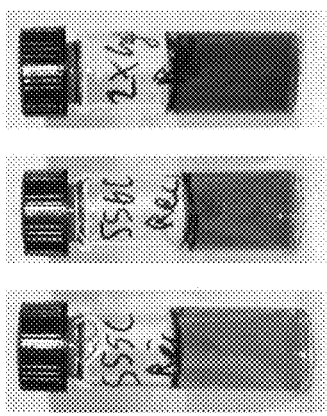
Figure 9:
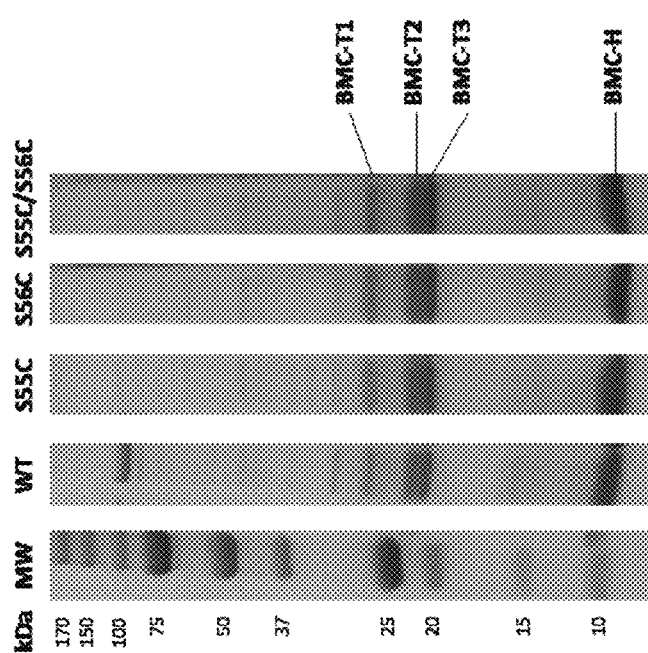
FIG. 9 shows a SDS-PAGE of purified Wild-Type (WT) shells, and purified shells containing engineered BMC-T1 proteins (BMC-T1-S55C, BMC-T1-S56C and BMC-T1-S55C/S56C). Molecular weight (MW) size markers are indicated in kDa on the left.
Figure 11B:
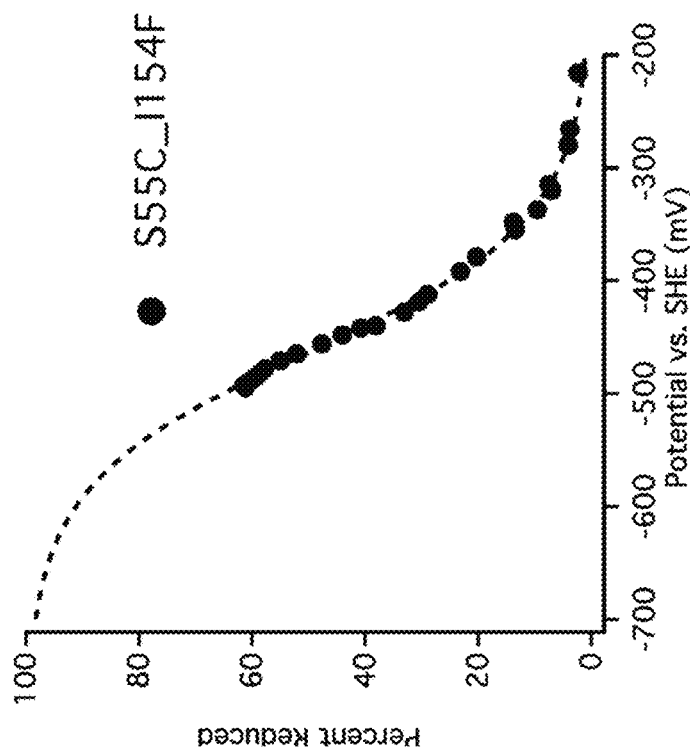
FIG. 11A-11B graphically illustrate the reduction potential of BMC-T1 [4Fe-4S] variants where the percentage of reduced protein is shown versus the solution potential, as detected by spectroelectrochemistry and fit using the Nernst equation.
Figure 11A:
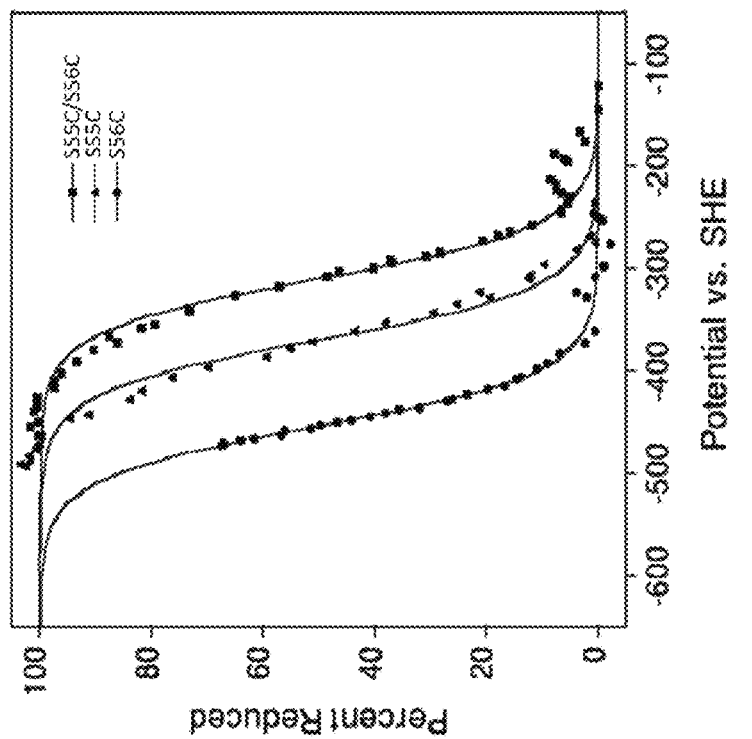

In addition to BMC-T1-S55C. additional mutants have been generated to fine-tune the reduction potential of the engineered [4Fe-4S] cluster. BMC-T1-S56C possesses a binding site that is distinct from the one in BMC-T1-S55C. with a different orientation and environment: the reduction potential is decreased to −455 mV vs. SHE (FIG. 11A). In BMC-T1-S55C/S56C. the C55 binding site is occupied by a [4Fe-4S] cluster, as shown by its crystal structure. UV-Vis and EPR spectroscopies (FIG. 8). The presence of additional cysteine residues (C56) increases the reduction potential to −310 mV vs. SHE (FIG. 11A). Like BMC-T1-S55C, these clusters have also been shown to be redox active and stable through redox cycles, providing a cofactor capable of sustaining efficient electron transfer. Moreover, these different mutant building blocks retain the ability to be incorporated into synthetic shells, as shown by SDS-PAGE analysis of purified shells (FIG. 9). This demonstrates that engineering BMC-T1 does not disrupt the formation of the shells, opening the way to use these different variants to transfer electrons across the shell of bacterial microcompartments or for potential incorporation in 2-dimensional scaffolds.

Figure 10G:
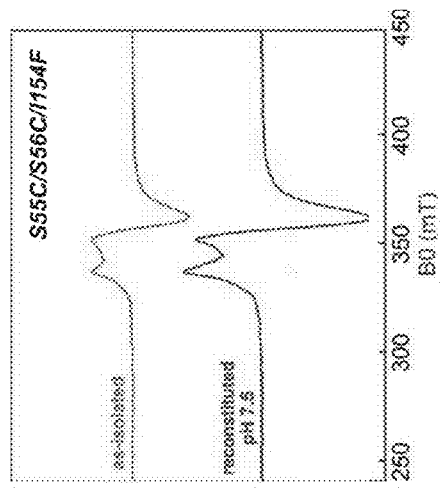
Figure 10F:
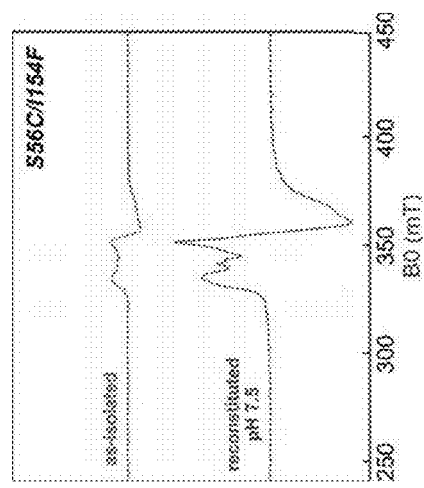
Figure 10E:
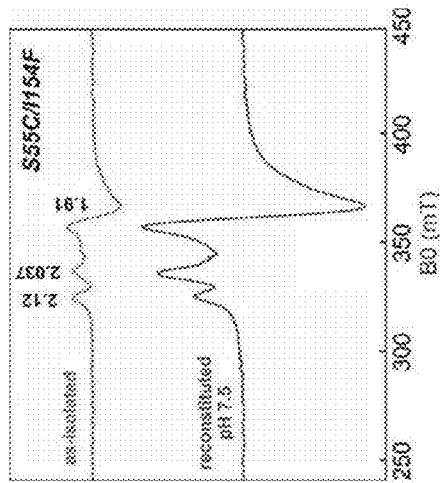

The addition in these three variants of an I154F mutation modifies the UV-Vis and EPR signatures of the clusters (FIG. 10), demonstrating a modification of their environment and of their reduction potential. For example, a reduction potential of about −460 mV vs. SHE (FIG. 11B) was estimated during the preliminary characterization of the [4Fe-4S] cluster present in BMC-T1-S55C/I154F. This library of engineered shell proteins provides optimal subunit pairings for the encapsulated pathway and the electron transfer module.

The following non-limiting Examples illustrate how aspects of the invention have been developed and can be made and used.

EXAMPLE 1

Materials and Methods

This Example describes some of the materials and methods used in developing the invention.

Plasmids, Bacterial Strains and Growth Conditions

A nucleic acid segment encoding BMC-T1 was subcloned in a pET 11 plasmid DNA vector from a previously described DNA construct (Lassila et al. 2014 JMB) coding for the seven shell proteins of the synthetic shells.

The BMC-T1 has the following amino acid sequence (SEQ ID NO: 1).

```
  1 MDHAPERFDA TPPAGEPDRP ALGVLELTSI ARGITVADAA

41 LKRAPSLLLM SRPVSSGKHL LMMRGQVAEV EESMIAAREI

81 AGAGSGALLD ELELPYAHEQ LWRFLDAPVV ADAWEEDTES

121 VIIVETATVC AAIDSADAAL KTAPVVLRDM RLAIGIAGKA

141 FFTLTGELAD VEAAAEVVRE RCGARLLELA CIARPVDELR

181 GRLFF
```

A modification of the BMC-T1 structure involving substitution of serine at position 55 with a cysteine (S55C) was made in the BMC-T1 gene using the QuikChange Lightning site-directed mutagenesis kit (Agilent Technologies) using the instructions provided by the manufacturer. An amino acid sequence for the S55C-modified BMC-T1 protein is as follows (SEQ ID NO:3).

```
  1 MDHAPERFDA TPPAGEPDRP ALGVLELTSI ARGITVADAA

41 LKRAPSLLLM SRPVCSGKHL LMMRGQVAEV EESMIAAREI

81 AGAGSGALLD ELELPYAHEQ LWRFLDAPVV ADAWEEDTES

121 VIIVETATVC AAIDSADAAL KTAPVVLRDM RLAIGIAGKA

141 FFTLTGELAD VEAAAEVVRE RCGARLLELA CIARPVDELR

181 GRLFF
```

The plasmids containing the sequence coding for BMC-T1 (pCA14) and BMC-T1-S55C (pCA15) were transformed in *E. coli* BL21 (DE3) for heterologous expression.

For the aerobic production of BMC-TL, the corresponding recombinant *E. coli* strain was grown in LB broth Miller with 100 µg/liter ampicillin at 37° C. with agitation (160 rpm) to an optical density at 600 nm of 0.6, then induced with 0.45 µM isopropyl thio-β-D-thiogalactoside (IPTG) and grown for another 15 hours at 22° C. The cells were then harvested and stored at −80° C.

The anaerobic production of BMC-T1-S55C was performed by a modified protocol from Kuchenreuther et al. (PLoS One 5(11): e15491 (2010)). Cultures were grown in a MOPS/NaOH buffered (100 mM, pH 7.5) LB-medium. First, bottles containing MOPS buffer were sparged with nitrogen gas to remove oxygen. The bottles were capped (using rubber caps) and transferred into an anaerobic chamber (Coy, Grass Lake, Mich.). The buffer was then supplemented with LB broth MILLER granulates (EMD Millipore). The bottles were sealed with rubber stoppers and autoclaved. The sterile media bottles were then anaerobically supplemented with 25 mM glucose, 25 mM sodium fumarate, 1 mM L-cysteine, 1 mM ferric ammonium citrate, 100 µg/liter ampicillin. The bottles were then inoculated (2% v/v) with an aerobically grown pre-culture. The anaerobic cultures were grown at 37° C. with agitation (120 rpm). When the cultures reached an optical density at 600 nm of 1, the culture was induced with 1 mM IPTG and grown for another 20 h at the same temperature. The cells were harvested and stored at −80° C. under anaerobic conditions.

Protein Purification and [Fe—S] Cluster Reconstitution.

BMC-T1 was purified as follows: cells (typically from 1 L *E. coli* culture) were resuspended in 50 mM Tris/HCl pH 7.5.75 mM NaCl (buffer A) (cell wet weight to buffer volume ratio 1:2) in the presence of DNAse and lysed by two consecutive passages through a French Press at a pressure of 137 MPa. This crude lysate was then heated to 55° C. for 30 min to precipitate other proteins (BMC-T is relatively stable at this temperature). This step was followed by centrifugation at 8,000 g for 20 min to pellet the precipitated proteins and cell debris. The supernatant was filtered through a 0.22 µm filter and loaded on a Tosoh Toyopearl SuperQ column equilibrated in buffer A. The protein was eluted using a gradient from 75 mM to 500 mM NaCl in 10 column volumes. Fractions showing the presence of the protein on SDS-PAGE were pooled and concentrated using an Amicon centrifugal concentrator (30 kDa cut-off). The protein was then applied to a gel filtration column (HiLoad 16/600 Superdex 75 µg. GE Healthcare) equilibrated with a 50 mM Tris/HCl pH 7.5, 150 mM NaCl buffer. The purified proteins were then stored at 4° C. Purified BMC-T1 was buffer-exchanged to 10 mM Tris/HCl pH 7.5 using a PD-10 column (GE Healthcare), and concentrated to 5.5 mg/ml for crystallization.

BMC-T1-S55C was purified as described above in an anaerobic chamber (Coy, Grass Lake, Mich.), typically from a 6 L anaerobic *E. coli* culture and using a MOPS/NaOH buffer system instead of Tris/HCl. Buffers used for the purification were degassed and allowed to equilibrate with the anaerobic chamber atmosphere (95% $N_2$, 5% $H_2$) for at least one day prior to use. After anion exchange chromatography, the sample was subjected to [Fe—S] cluster reconstitution under anaerobic conditions: the diluted protein was incubated with 10 mM DTT for 1 hour at 4° C., then $FeCl_3$ was added to a final concentration of 400 µM and followed by a 3-4 h incubation at 4° C. Finally, the same concentration of $Na_2S$ was added, and the sample was incubated at 4° C. overnight, before being concentrated, filtered and purified using gel filtration. For crystallization experiments, reconstituted BMC-T1-S55C was buffer exchanged to 10 mM MOPS/NaOH pH 7.5, 10 mM NaCl, 10 mM DTT and concentrated to 8.5 mg/ml.

Protein concentrations were determined using the bicinchoninic acid (BCA) kit (Sigma-Aldrich). Iron content was determined by the ferrozine method (Stookey. L. L. *Anal. Chem.* 1970, 42, 779).

Crystallization and Structure Determination

BMC-T1 crystals were obtained by mixing 2 µl of protein with an equal volume of a reservoir condition containing 30 mM citric acid, 70 mM BIS-Tris propane (final pH 7.6) and 18% PEG 3.350. Crystals were cryoprotected using PEG 400 at a final concentration of 25%. BMC-T1-S55C crystals were grown in sitting drops using 250 mM sodium acetate, 100 mM Tris/HCl pH 8.5, 26% PEG 4,000 as reservoir condition (protein/reservoir ratio of 1:1). Cryoprotection was achieved using 38% 1,2-propanediol and 21% 2-methyl-2,4-pentanediol (MPD; final concentrations). Stabilized crystals were flash frozen in liquid nitrogen until data collection. For BMC-T1-S55C, all steps (except looping and freezing steps) were conducted in a Coy anaerobic chamber (Coy, Grass Lake, Mich.). X-ray diffraction data were collected at beamline 12-2 of the Stanford Synchrotron Radiation Lightsource (BMC-T1) and at the Advanced Light Source at Lawrence Berkeley National Laboratory beamline 5.0.3 (BMC-T1-S55C, 100 K, 1.0000 Å wavelength). Diffraction data were integrated with XDS (Kabsch, *Acta Crystallogr. D Biol. Crystallogr.* 66: 125 (2010)) and scaled with SCALA (CCP4, Winn et al. *Acta Crystallogr. D Biol. Crystallogr.* 67: 235 (2011)). The BMC-T1 structure was solved by molecular replacement (MR) in Phaser (McCoy, J Appl Crystallogr 40: 658 (2007)) using a carboxysome BMC-T protein, CsoS1D from *Prochlorococcus nmarinus* (PDB ID: 3FCH) as the search model. Autobuilding was performed using phenix.autobuild (Adams et al. *Acta Crystallogr. D Biol. Crystallogr* 66: 213 (2010)) followed by cycles of manual rebuilding in COOT[28] (Emsley & Cowtan, *Acta Crystallogr. D Biol. Crystallogr* 60: 2126 (2004)) and refinement with phenix.refine (Adams 2010), which also performed the automatic water picking. The structure of BMC-T1-S55C was solved using molecular replacement with the structure of BMC-T1. Statistics for diffraction data collection, structure determination and refinement are summarized in Table 1.

TABLE 1

| Data collection and refinement statistics | | |
|---|---|---|
| | BMC-T1 | BMC-T1-S55C |
| Data collection | | |
| Space group | P 2$_1$ | P 1 |
| Cell dimensions | | |
| a, b, c (Å) | 69.63  66.38  122.25 | 42.9  55.6  117.9 |
| α, β, γ (°) | 90.0  92.4  90.0 | 83.5  81.2  87.0 |
| Resolution (Å) | 31.51-2.44 (2.58-2.44)* | 38.62-1.80 (1.87-1.80)* |
| R$_{merge}$ | 0.107 (0.417) | 0.054 (0.610) |
| I/σI | 8.3 (3.1) | 11.3 (1.4) |
| Completeness (%) | 96.5 (93.3) | 96.6 (91.3) |
| Redundancy | 3.3 (3.3) | 2.1 (2.0) |
| Refinement | | |
| Resolution (Å) | 31.5-2.44 | 38.6-1.80 |
| No. reflections | 74,297 | 176,094 |
| R$_{work}$/R$_{free}$ | 23.3/27.7 | 18.1/22.3 |
| No. atoms | 9,018 | 9,244 |
| Protein | 8,687 | 8,821 |
| Ligand/ion | — | 16 |
| Water | 331 | 407 |
| B-factors | 39.0 | 33.4 |
| Protein | 39.4 | 33.1 |
| Ligand/ion | — | 28.2 |
| Water | 40.1 | 39.8 |
| R.m.s deviations | | |
| Bond lengths (Å) | 0.003 | 0.019 |
| Bond angles (°) | 0.597 | 1.96 |

1 crystal per dataset,
*Values in parentheses are for highest-resolution shell.

The final model had 93.8% and 95.9% of the residues in the favored, 6.1% and 3.9% in the allowed and 0.1% and 0.2% in the disallowed region of the Ramachandran plot for BMC-T1 and BMC-T1-S55C, respectively. Figures of structural models were prepared using PyMOL (www.pymol.org). Atomic coordinates and structure factors (PDB ID: 5DIH for BMC-T1 and 5DII for BMC-T1-S55C) have been deposited in the Protein Data Bank (see website at pdb.org).

Optical Spectroscopy.

UV-vis spectra were recorded in anaerobic conditions using an Agilent Technologies Cary60 UV-Vis spectrophotometer. For reduction tests, proteins (in 50 mM MOPS/NaOH pH 7.5, 75 mM NaCl) were mixed in anaerobic conditions with 0.5 mM sodium dithionite and incubated for 5-10 min before recording the spectra.

Electron Paramagnetic Resonance (EPR).

Continuous wave EPR experiments at variable temperatures (5-70 K) were carried out at a Bruker ESP300 spectrometer equipped with a continuous flow cryostat (Oxford Instruments) and a Bruker ER/4102 ST rectangular resonator which operates in the TE$_{102}$ (9.48 GHz) perpendicular mode. The microwave frequency was measured with a 5350B Hewlett Packard frequency counter. For all experiments, custom-made quartz tubes of the same inner and outer diameter were used (QSI). Quantitation of the signals was carried out by measuring a 256 µM Cu$^{2+}$-EDTA standard under non-saturating conditions by double numerical integration of the first-derivative experimental and simulated EPR spectra. All quantifications were carried out for the spectra recorded at T=10 K. The first-derivative EPR spectra were simulated using the MATLAB (Mathworks) based Easyspin simulation software (Stoll & Schweiger. A. J. Magn. Reson. 178: 42 (2006). The samples were transferred to the EPR tubes under anaerobic conditions and were quickly frozen in liquid nitrogen in a Coy anaerobic chamber prior to measuring.

Redox Potentiometry.

Chemical redox titrations were performed as described by Dutton (Methods Enzymol. 54: 411 (0.1978)) and all values are reported relative to the SHE. Titrations were performed in aqueous solutions containing 60 µM iron-sulfur cluster protein in 50 mM MOPS/NaOH pH 7.5, 75 mM NaCl with the following mediators: anthraquinone-2,6-disulphonate (0.6 µM), anthraquinone-2-sulphonate (0.6 µM), benzyl viologen (0.2 µM) and methyl viologen (0.2 µM). Reduction was accomplished with sodium dithionite and re-oxidation with duroquinone. The normalized absorbance change at 422 nm (selected to eliminate the contribution of the viologen dyes) due to [4Fe-4S] cluster reduction was fitted to an N=1 Nernst equation.

EXAMPLE 2

Structural Characterization of BMC-T1

Synthetic HO shells were derived from a BMC of unknown function encoded in the genome of the myxobacterium *Haliangium ochraceum* (see, e.g., Lassila et al., *J. Mol. Biol.* 426: 2217 (2014): Axen et al., *PLoS Comput. Biol.* 10: e1003898 (2014)). The synthetic HO shells were composed of seven gene products: four BMC-T1-T3 and one BMC-H protein (FIG. 1; Lassila et al., *J. Mol. Biol.* 426: 2217 (2014)).

BMC-T1 (locus tag: Hoch_5812) was selected for characterization and as a scaffold for the incorporation of a metal center because it forms trimers that incorporate into single layered facets of the synthetic shell.

*Haliangium ochraceum* shell proteins tend to be only distantly related to their counterparts in experimentally characterized BMCs (e.g. the propanediol utilization and ethanolamine utilization BMCs and the carboxysome). For example, a BLAST search of the non-redundant sequence database indicates the closest homolog of BMC-T1 is a BMC-T protein encoded in the genome of *Hyalangium minutum* (which also belongs to the Myxococcales) with 49% identity. The next closest homologs share only 37% identity or less with BMC-T1. In a query of the Protein Data Bank (PDB), three hits, each 36% identical at the level of primary structure, were returned: PduT, a BMC-T protein of the propanediol utilization BMC of *Salmonella enterica* (PDB ID 3N79) and *Citrobacter freundii* (PDB ID 3PAC), as well as a homolog from a glycyl radical enzyme-associated BMC[3] identified in *Desulfitobacterium hafniense* (PDB ID 3NWG). Given this relatively remote sequence homology to structurally characterized BMC shell proteins, the structure of BMC-T1 Wild Type (WT) was determined to guide the design of a [4Fe-4S] cluster-binding site.

Figure 2A:
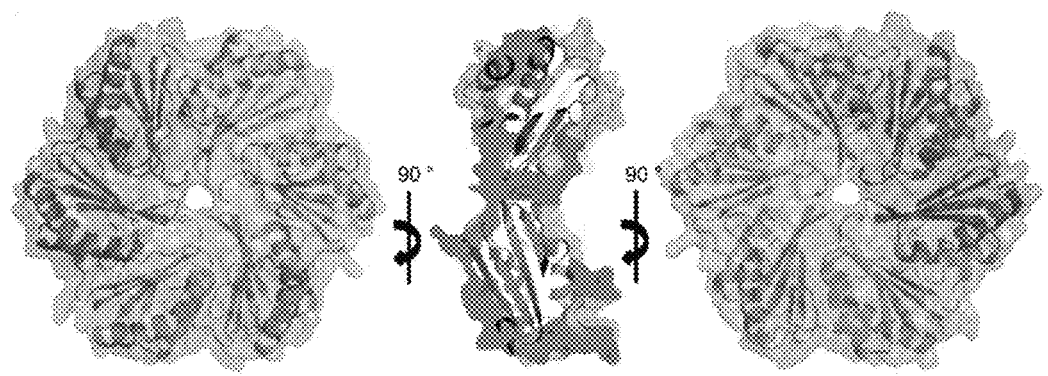
FIGS. 2A-2G illustrate structural features of a BMC-T1 component of a BMC shell and biochemical characterization of BMC-T1-S55C.

The BMC-T1 wild type protein was over-expressed in *Escherichia coli*, and the purified protein was crystallized in the monoclinic space group P2$_1$. The crystals diffracted to a resolution of 2.4 Å (Table 1), and the structure was solved by molecular replacement using CsoS1D from *Prochlorococcus marinus* (PDB ID: 3FCH) as the search model. There were six subunits (two trimers) per asymmetric unit; the trimer structure is shown FIG. 2A. Due to disordered termini and loops, varying numbers of amino acids (between 3 and 23 residues per chain) had to be omitted from the N-termini and some loop regions of the three monomers. Data collection and refinement statistics are provided in Table 1.

EXAMPLE 3

Structure-based Rational Design of a [4Fe-4S] Cluster Binding Site into BMC-T1

Figures 2B, 2C:
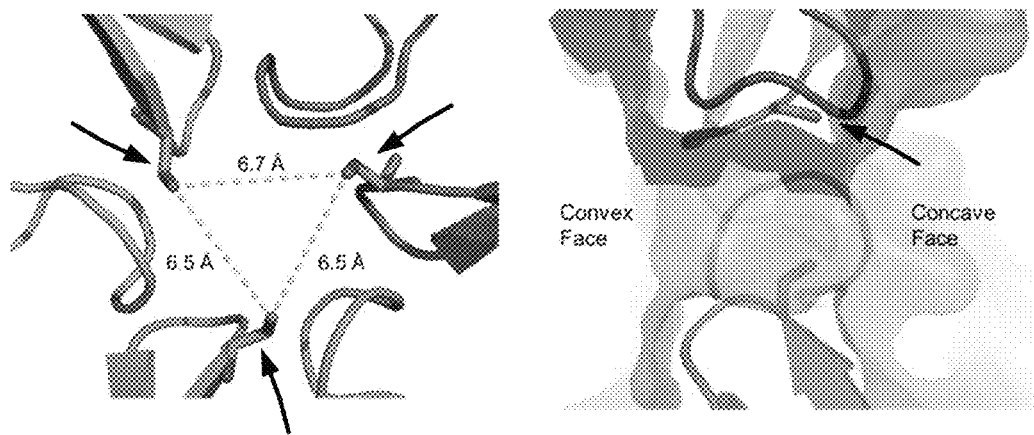
Figure 2D:
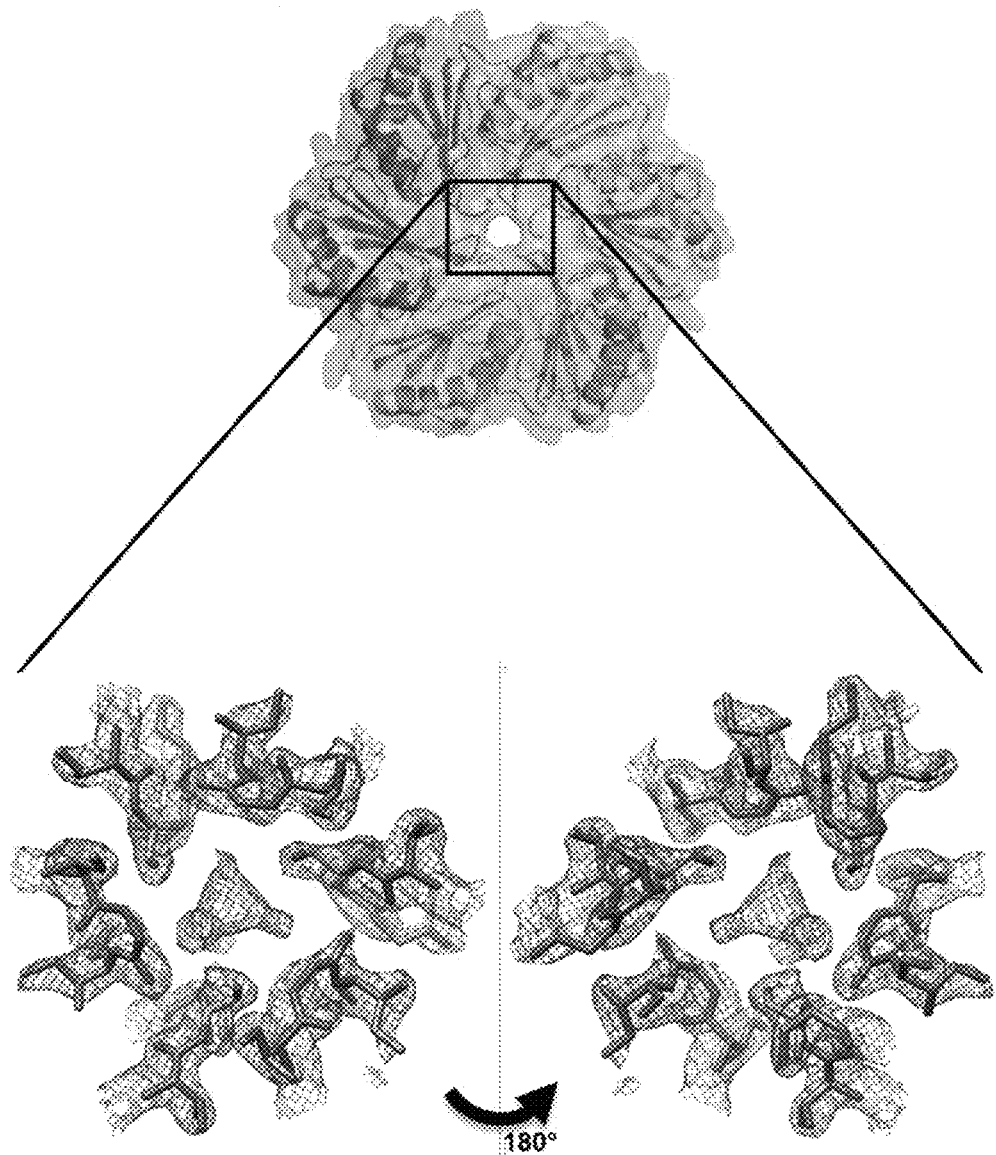

The structure of BMC-T1 was used to design a [4Fe-4S] cluster-binding site at the cyclic axis of symmetry of the trimer. The hydroxyl side chains of Ser55 from each protomer are arranged in a trigonal plane with $O_\gamma$-$O_\gamma$ distances between 6.46 and 6.74 Å (FIGS. 2B and 2D). This arrangement is reminiscent of the $S_\gamma$-$S_\gamma$ bite distances of cysteine residues coordinating [4Fe-4S] clusters in natural ferredoxins (Petros et al., *Inorg. Chem.* 45: 9941 (2006)). The inventors hypothesized that the pore formed at the symmetry of the BMC-T1 trimer could serve as a [4Fe-4S] cluster-binding site. The side chains of the three Ser55 residues (one from each protomer) point towards the concave side of the trimer (FIG. 2A, 2C) and are in a gauche(+) conformation with $\chi_1$ angles of 111-112° (FIG. 2B-2C). Furthermore, the rigid β-turn motif that contains Ser55 disfavors structural rearrangement to accommodate a rubredoxin-type mononuclear iron that requires a smaller bite distance of 3.8 Å (Petros 2006). In view of the geometry and bite distance, and the three-fold symmetry axis (pore), the inventors decided to substitute Ser55 with a cysteine to accommodate binding of a [4Fe-4S] cluster (referred to as BMC-T1-S55C).

EXAMPLE 4

The Structure of BMC-T1-S55C Confirms Incorporation of a [4Fe-4S] Cluster

Figure 2F:
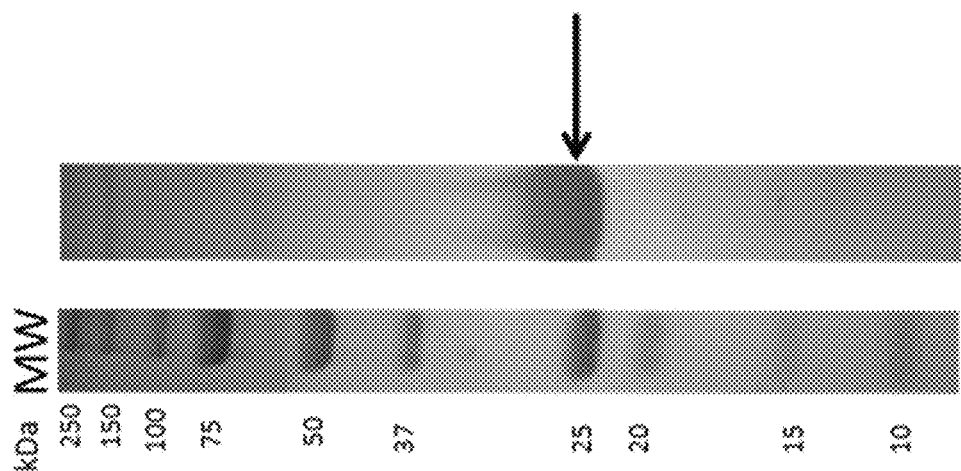
Figure 2E:
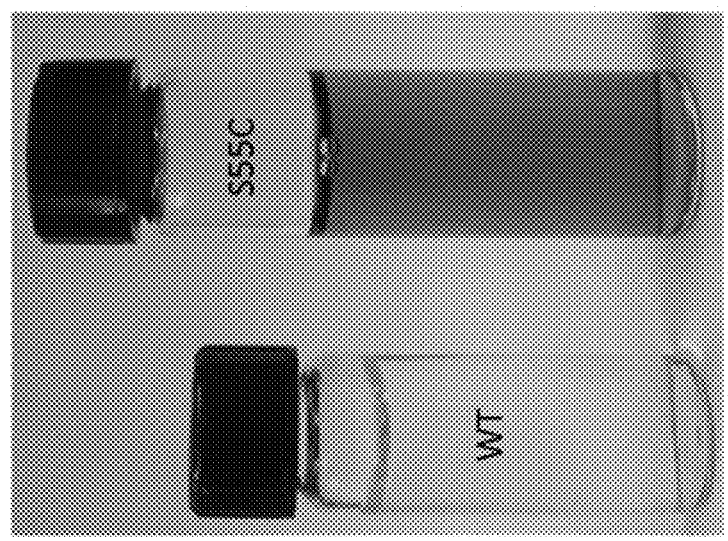
Figure 2G:
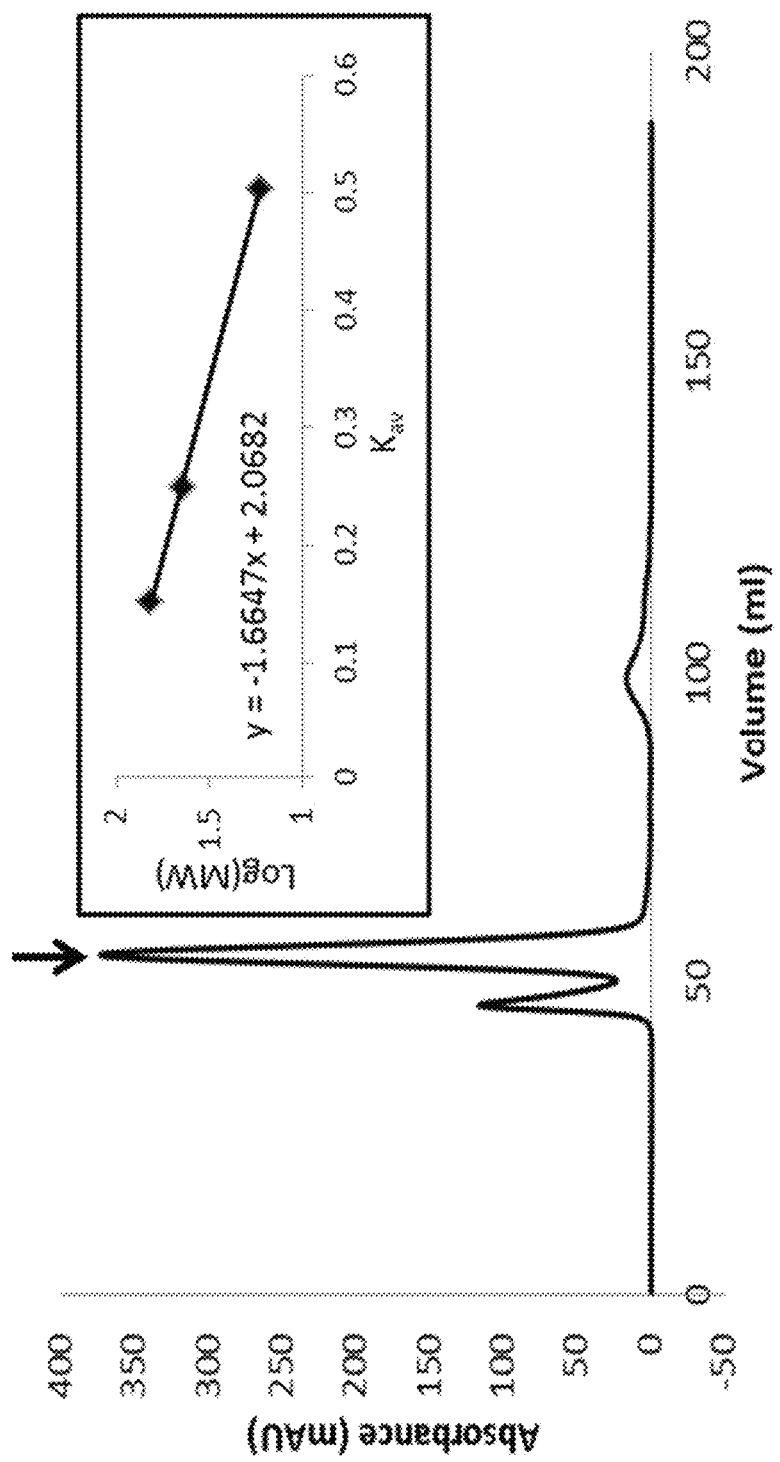

Because [4Fe-4S] clusters are typically oxygen-sensitive, purification of BMC-T1-S55C was conducted in anaerobic conditions using the same purification protocol as described for the wild type protein. In stark contrast to the colorless wild protein, purified BMC-T1-S55C exhibited a brown color, indicating the presence of an [Fe—S] cluster (FIG. 2E). Size exclusion chromatography confirmed that BMC-T1-S55C is a trimer (FIG. 2F-2G).

Figure 3E:
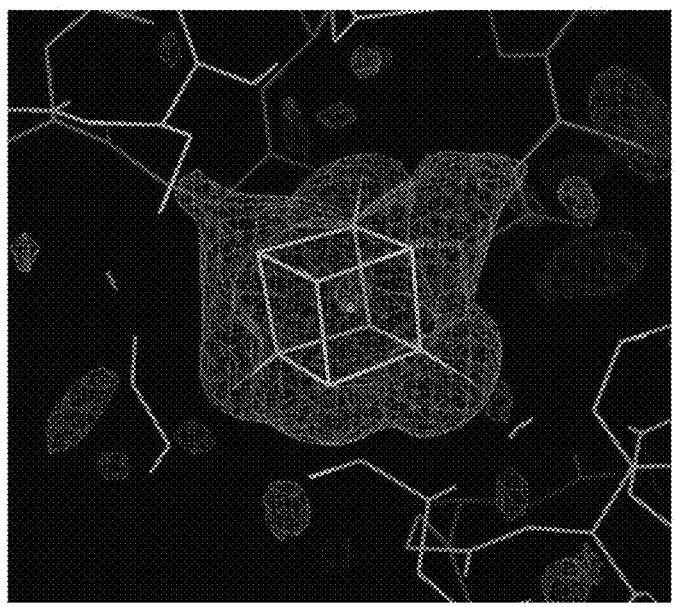
Figure 3F:
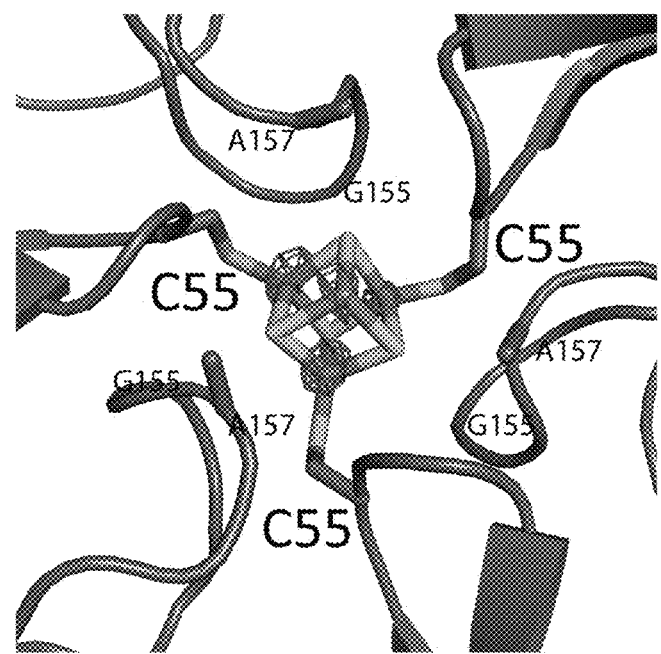

BMC-T1-S55C was crystallized anaerobically, and the structure was solved at 1.8 Å resolution by molecular replacement using the wild type structure as the search model (Table 1). There are two trimers in the asymmetric unit of the P1 space group. The electron density was of high quality, with only a few (<6) residues at the N-termini and in some flexible loops (Ala14, Gly15, and Glu116-Thr118) that could not be modeled due to disorder. Both trimers contain electron density that could be readily modeled as a [4Fe-4S] cluster in the middle of the central, positively charged pore (FIG. 3A-3D). The electron density is well-defined, and the positions of the iron atoms were confirmed by their anomalous signal (FIG. 3E-3F). The occupancy for the [4Fe-4S] cluster was refined to 72-74%.

Figure 3G:
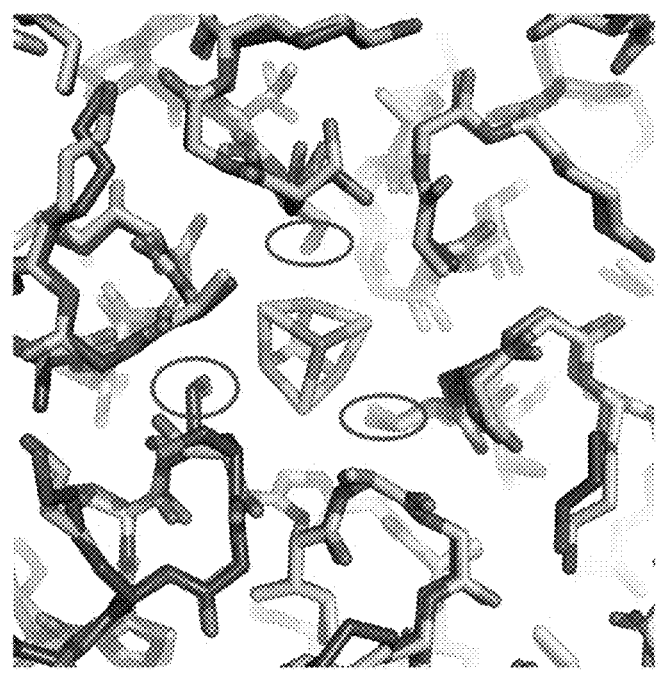

Using the ferrozine assay to measure metal content, about 60% of the protein was estimated to contain a [4Fe-4S] cluster, consistent with the results of the structure determination. Three of the iron atoms of each cluster are coordinated by the three introduced cysteines (S55C), and a water or hydroxide molecule ligates the fourth unique iron (FIG. 3B). The $S_\gamma$Cys55-Fe and Fe—$OH_2$/OH bonds have distances of 2.3 Å and 2.1 Å, respectively. The Fe—S bonds within the cluster have an average length of 2.2 Å. The Fe—Fe distance is 2.8 Å. These values are comparable to those observed in a variety of [4Fe-4S] cluster proteins and synthetic [4Fe-4S] cluster analogs (Fe—S distances of ~2.3 Å and Fe—Fe distances of ~2.5-2.8 Å) (Stout, in *Encyclopedia of Inorganic and Bioinorganic Chemistry*; John Wiley & Sons. Ltd: Online (2011): Giastas et al., *J. Biol. Inorg. Chem.* 11: 445 (2006); Mitra et al., *J. Am. Chem. Soc.* 135: 2530 (2013); Herskovitz et al., *Proc. Natl. Acad. Sci. U.S.A.* 69: 2437 (1972)). Moreover, three of the cluster sulfides make hydrogen bonds with the amide backbone of residues Ala157 (of each protomer) with H to S distances of 2.7-2.8 Å (N to S distances of 3.4-3.5 Å) (FIG. 3B); these are comparable to main chain-cluster bonds observed in other [4Fe-4S] cluster-containing proteins (Giastas 2006; Fukuyama, In *Encyclopedia of Inorganic and Bioinorganic Chemistry*; John Wiley & Sons, Ltd: Online (2011)). The sulfur atoms of Cys55 are hydrogen-bonded to the backbone amide of Gly155 with S to H distances of 2.1-2.2 Å (S to N distances of 3.1-3.2 Å) (FIG. 3B). These hydrogen bonds are also present in the BMC-T1 (wild type) structure (amide backbone of Gly155 and $O_\gamma$ of the Ser55 side chain), demonstrating that the Ser55 to Cys55 mutation did not perturb the overall structure of BMC-T1. This is further corroborated by a structural superposition of BMC-T1 and BMC-T1-S55C (FIG. 3G); the RMSD (root-mean-square deviation) for 160 α-carbon atom pairs is 0.5 Å. Furthermore, the conformation of the three cysteine residues is conserved with respect to their serine equivalent ($\chi_1$ angle of ~110°). Overall, the structure validates the original design criteria, and most importantly, it represents the first structure of a designed [4Fe-4S] protein.

EXAMPLE 4

Characterization of the [4Fe-4S] Cluster in BMC-T1-S55C by Optical Spectroscopy

Figure 4A:
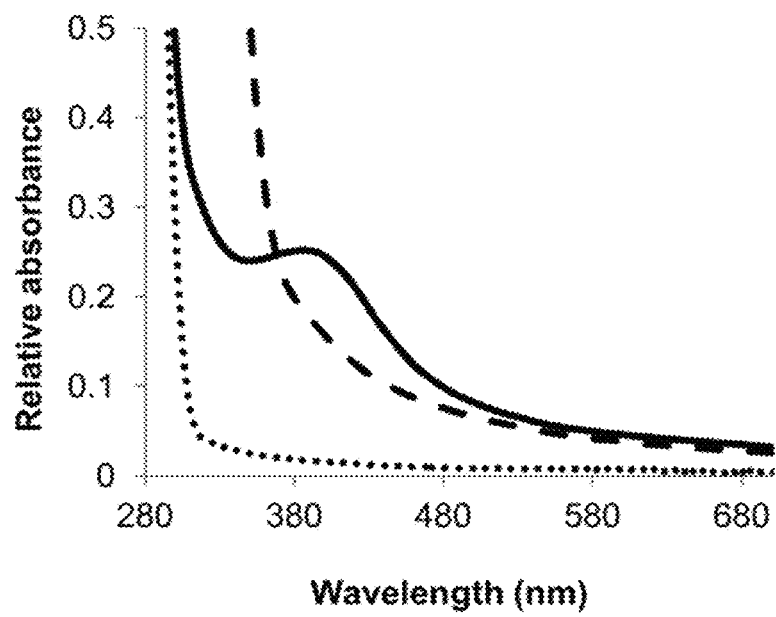
FIGS. 4A-4E show UV-Visible and EPR spectra of BMC-T1 and BMC-T1-S55C.

The UV-Visible (UV-Vis) spectrum of BMC-T1 does not show any absorbance features other than the 280 nm band of the aromatic residues (FIG. 4A). In contrast, after [Fe—S] cluster reconstitution of BMC-T1-S55C, the optical spectrum recorded under anaerobic conditions exhibited a broad absorption band at approximately 385 nm (FIG. 4A), which is characteristic of S-to-Fe(III) charge transfer transitions observed in [Fe—S]cluster-containing proteins (Sweeney & Rabinowitz. *Annu. Rev. Biochem.* 49: 139 (1980); Lippard & Berg. In *Principles of Bioinorganic Chemistry*; University Science Books: Mill Valley, Calif. (1994)).

Figure 4C:
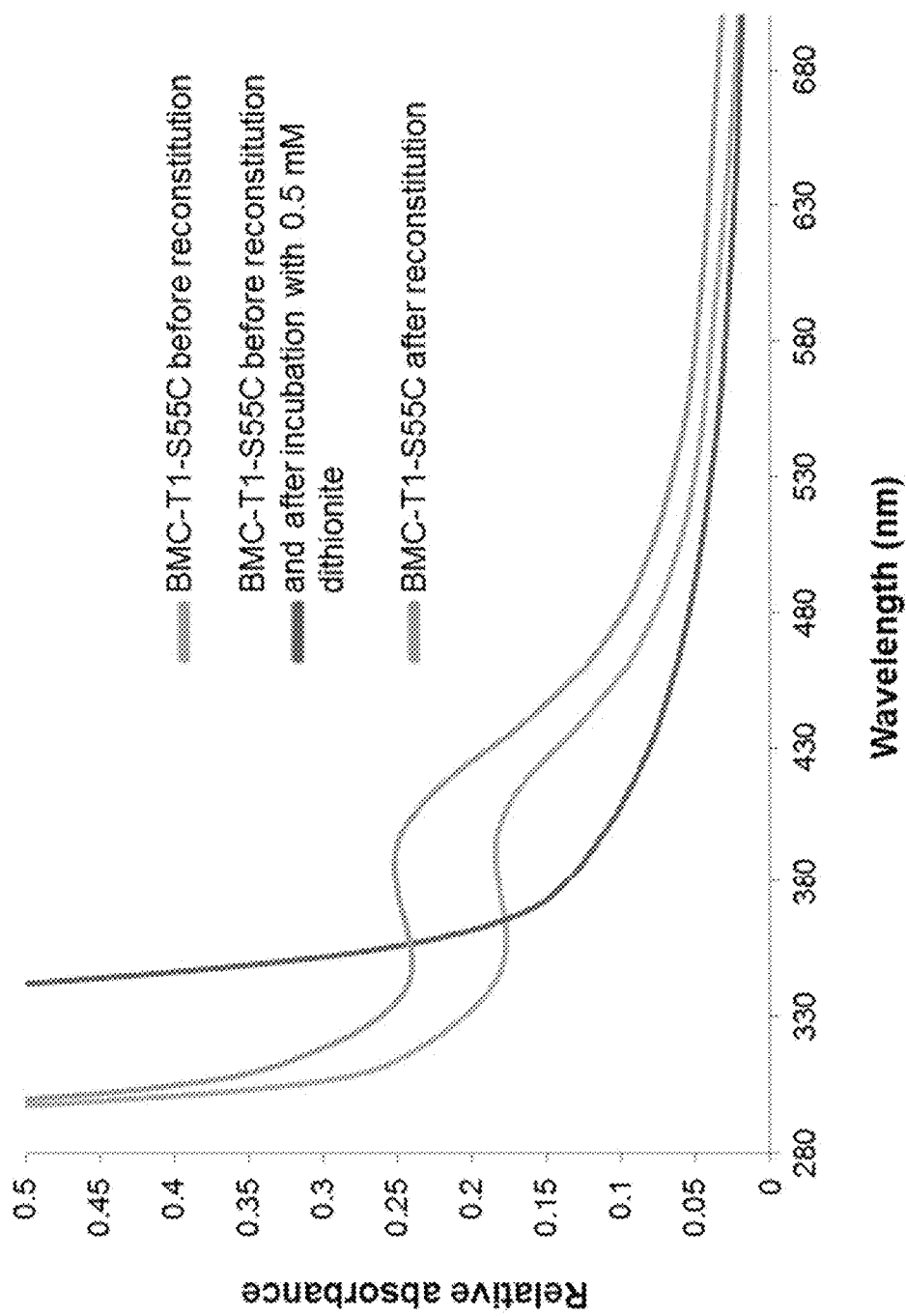

In addition, there is no evidence for bands that are typically observed for [2Fe-2S] clusters (features at 310-330 nm, 420 nm, and 465 nm), indicating that the trimer contains exclusively a [4Fe-4S] cluster, as observed in the crystal structure. Treatment with dithionite (−660 mV vs. SHE at pH 7; Mayhew. *Eur J. Biochem* 85: 535 (1978)) resulted in complete disappearance of the optical features (FIG. 4A), consistent with reduction of the cluster. Based on the [4Fe-4S] cluster occupancy in the crystal structure, the extinction coefficient at 385 nm is between 18,000-19,000 $M^{-1} \cdot cm^{-1}$, which is within the range reported for other [4Fe-4S] clusters (16,000-23,000 $M^{-1} \cdot cm^{-1}$; Sweeney & Rabinowitz 1980). Furthermore, similar results were obtained with the non-reconstituted BMC-T1-S55C, although the [4Fe-4S] cluster band was less intense (FIG. 4C). This indicates a lower efficiency in cluster incorporation; we estimated that about 50% of the protein spontaneously binds a cluster in vivo. Enhancement in cluster incorporation by chemical reconstitution is well known, especially in the case of $O_2$-sensitive [Fe—S] cofactors or when overexpressing the [Fe—S] containing proteins in the absence of the auxiliary Iron-Sulfur Cluster maturation machinery (Lanz et al., *Methods Enzymol.* 516: 125 (2012)).

EXAMPLE 5

Characterization of the [4Fe-4S] Cluster in BMC-T1-S55C by EPR Spectroscopy

Figure 4D:
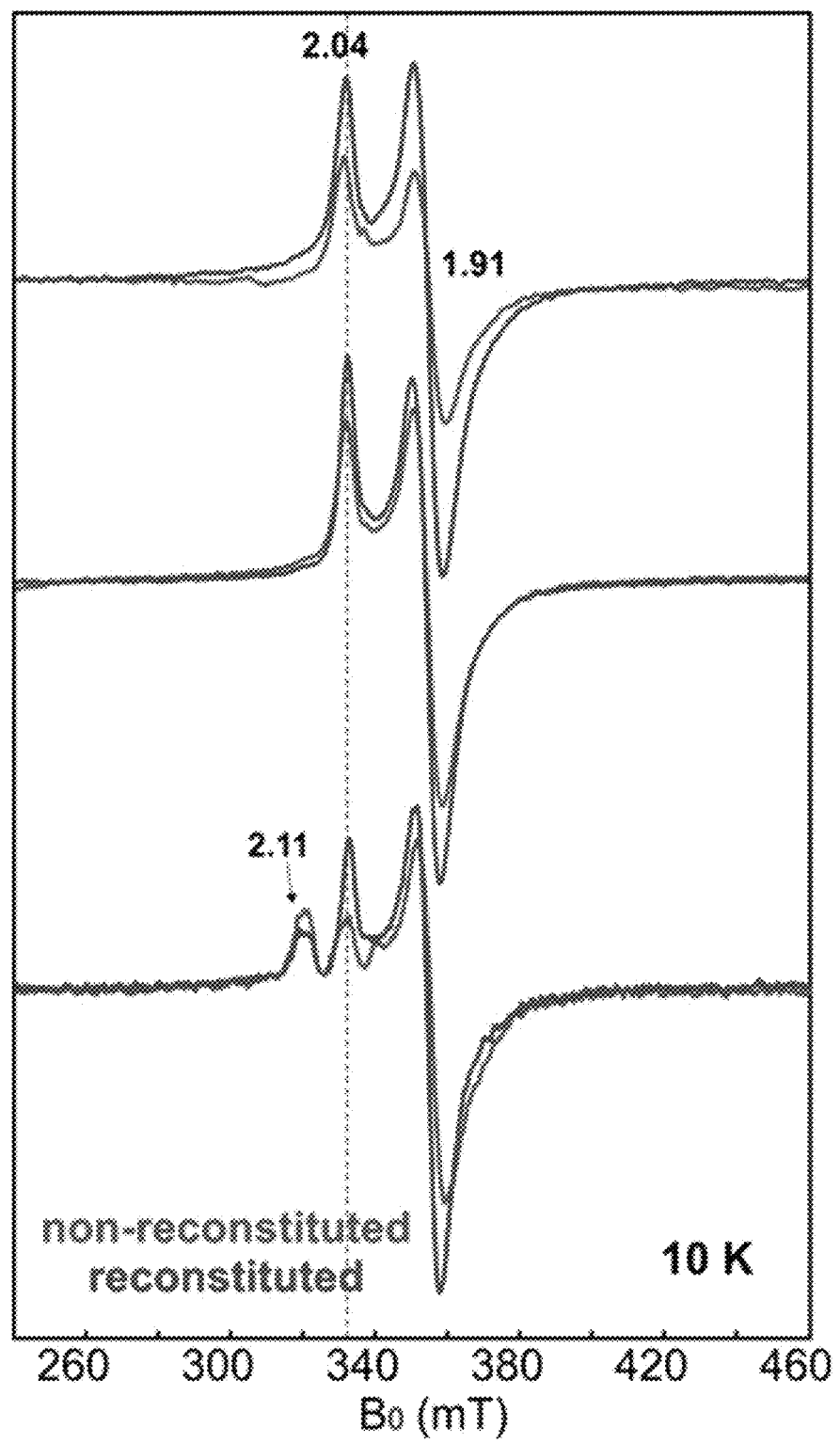
Figure 4E:
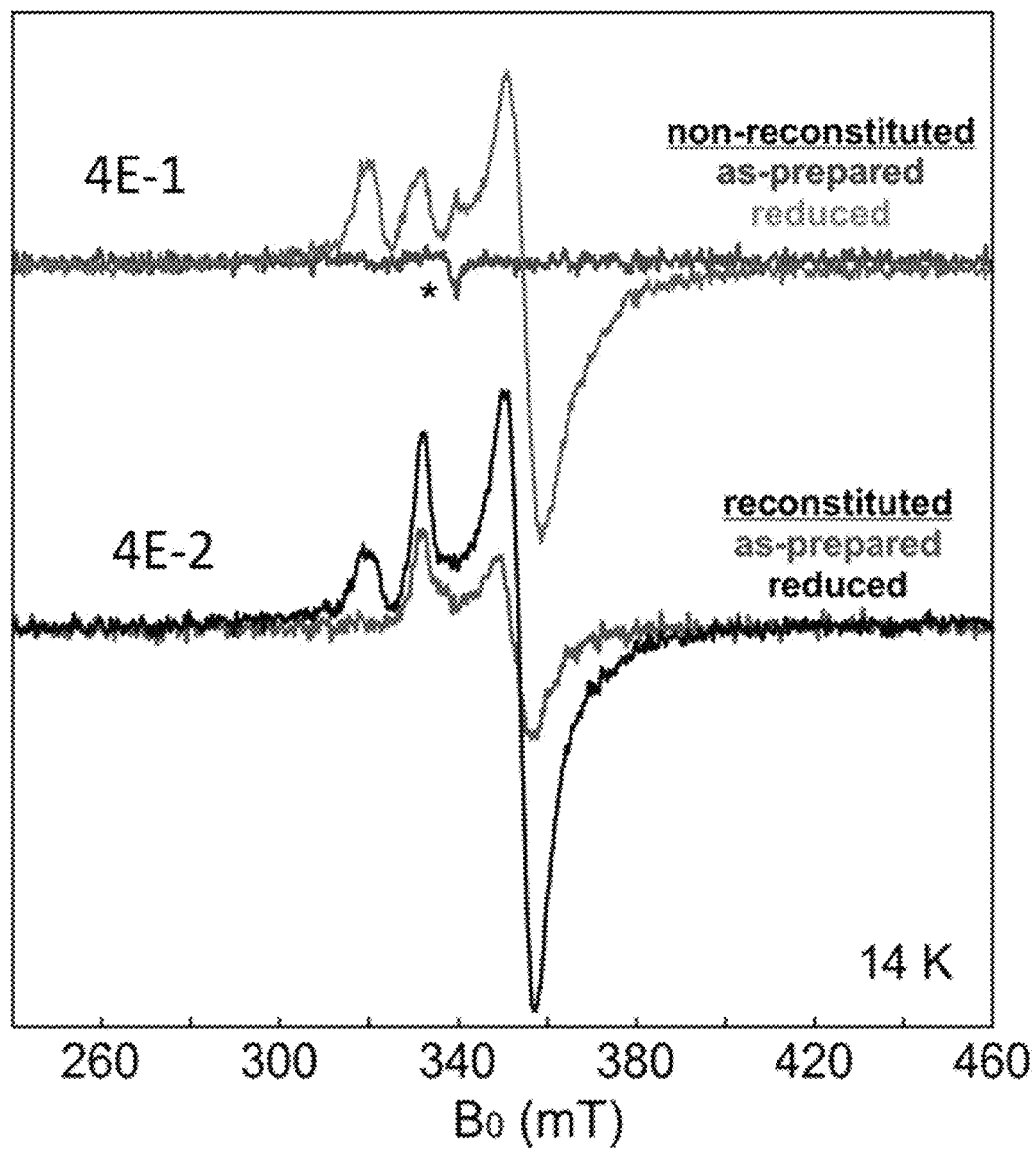

The continuous wave (CW) X-Band EPR spectrum of BMC-T1 (with and without dithionite) exhibited no paramagnetic signals attributable to [Fe—S] clusters (FIG. 4B), which is in agreement with its UV-Vis spectrum. In contrast, after reduction with dithionite, both the purified, non-reconstituted and the chemically reconstituted BMC-T1-S55C proteins exhibited qualitatively comparable EPR spectra that are reminiscent of [4Fe-4S] clusters (FIG. 4B, 4D-4E). The degree of [4Fe-4S] cluster incorporation in BMC-T1-S55C was consistently higher in the chemically reconstituted protein than in the non-reconstituted form, which again corroborates the results of the UV-Vis analysis. The EPR spectrum of the reconstituted, chemically reduced BMC-T1-S55C was characterized by an axial signal with $g_{av}$ of 1.98 and principal g-values 2.04 and 1.91, respectively. The intensity of this signal was strongly temperature-dependent and was barely detectable at temperatures above 45 K (FIG. 4B). The effective g-values and the relaxation properties were typical of those reported for [4Fe-4S]$^+$ clusters with an S value of ½ ground state.[41] In the case of the non-reconstituted BMC-T1-S55C sample reduced with dithionite, the EPR signal, albeit very similar, exhibited a slight downshift in the low-field g-component, small changes in the rest g-values, and broader linewidths (FIG. 4E). These observations indicate a higher degree of heterogeneity with respect to the reconstituted sample, which can be attributed to the formation of clusters in slightly different local protein environments. The EPR signals of the assembled [4Fe-4S] cluster in BMC-T1-S55C varied only marginally between different protein preparations; changes in small g-values shifts and overall signal line shape broadness, indicating that the incorporated cluster is rather sensitive to local changes in its protein environment (FIG. 4D). In some cases, an additional low-field signal at g ~2.11 was detected, indicating the presence of a second cluster form. After reconstitution, the intensity of this component was markedly reduced, consistent with a conclusion that the [4Fe-4S] cluster incorporated in the chemically reconstituted samples exhibits less heterogeneity (FIG. 4D). The g ~2.11 signal may be associated with a different orientation of the [4Fe-4S] cluster, in which the water/hydroxide-ligated iron would be oriented towards the concave face of the trimer instead of being located in the pore, or to a different coordination state where the water molecule may be replaced by an inorganic or protein ligand.

To determine if any [3Fe-4S] clusters were present in BMC-T1-S55C, the EPR spectra were measured prior to reduction with dithionite (in both its non-reconstituted and reconstituted forms). No signals attributable to [3Fe-4S]$^{1+}$ clusters were detected (gay about 2.01) (FIG. 4E), thus confirming that only [4Fe-4S] clusters were assembled. In addition, in the reconstituted sample without dithionite, a small amount (about 20% of the total cluster content) of [4Fe-4S]$^{1+}$ clusters could be observed, indicating that under these conditions an appreciable fraction of the clusters was partially reduced. Overall, the assembled [4Fe-4S] cluster in BMC-T1-S55C exhibited EPR signals and relaxation properties highly reminiscent of those observed in classical [4Fe-4S]$^{1+}$ low-potential ferredoxins.

EXAMPLE 6

Spectroelectrochemistry of BMC-T1-S55C

The midpoint reduction potential, $E_m$, of BMC-T1-S55C was determined using UV-Vis detected spectroelectrochemistry (FIG. 5A). The reduction potential of the [4Fe-4S] cluster in BMC-T1-S55C was determined to be −370 mV vs. SHE (±10 mV), which is in agreement with the efficient reduction of the cluster by dithionite. This value also explains the observation of partially reduced clusters after incubation with DTT (−332 mV at pH 7) (Cleland, Biochemistry 3: 480 (1964)) during the chemical reconstitution of the cluster (FIG. 4E). Furthermore, reduction of the cluster by dithionite was fully reversible upon addition of duroquinone as an oxidant. Successive reduction/oxidation cycles were repeated without any degradation of the [4Fe-4S]$^{2+}$ cluster UV-Vis signature at ~385 nm (FIG. 5B).

EXAMPLE 7

Stability of the [4Fe-4S] Cluster in BMC-T1-S55C Upon Chemical Denaturation and Oxygen Exposure To test whether the presence of a cluster can stabilize host proteins in the system described herein, a chemical denaturation was performed on BMC-T1 and BMC-T1-S55C using urea with monitoring by circular dichroism (CD) spectroscopy.

The results illustrated in FIG. 6A-6D show that BMC-T1 is fully denatured at 6 M urea. In contrast, BMC-T1-S55C is extremely resistant to chemical denaturation. Very little unfolding was detected even at concentrations of urea as high as 10.2 M (FIG. 6A-6D). Moreover, the UV-Vis spectrum of BMC-T1-S55C in 10.2 M urea exhibits the typical signal at 385 nm (FIG. 6A-6D). These data indicate that BMC-T1-S55C and its [4Fe-4S] cluster are an extremely stable assembly.

The response of the [4Fe-4S] cluster in BMC-T1-S55C toward oxygen was also determined. A sample of the anaerobic protein was exposed to air, and UV-Vis and EPR spectra (without dithionite) were recorded at different time points (FIG. 6E-6F). EPR spectra showed that upon exposure to air, a transient [3Fe-4S]$^{1+}$ cluster is generated, but to only sub-stoichiometric amounts such as 5 µM. In combination with the observations from UV-Vis spectroscopy, in which a decrease of the [4Fe-4S] charge transfer band is relatively fast and accompanied by features that are somewhat reminiscent of [2Fe-2S] clusters, these results demonstrate that the [4Fe-4S] cluster is indeed susceptible to oxidation by dioxygen. This $O_2$-dependent degradation appears to proceed via a [3Fe-4S]$^{1+}$ intermediate (by release of one of the Fe) and later formation of an $O_2$-unstable [2Fe-2S] cluster to its complete degradation after prolonged exposure (several hours to a day).

None-the-less, the BMC-T1-S55C iron cluster seems somewhat tolerant to oxygen. For example, initial purifications of BMC-T1-S55C were performed under aerobic conditions from aerobically grown cultures. The purified protein retained a brown color for a few weeks at 4° C. without bleaching of the chromophore or any precipitation. Another indication of oxygen tolerance is the presence of the intact cluster in the BMC-T1-S55C structure, even though preparing the crystals for data collection required brief exposure to aerobic conditions.

REFERENCES (1) Kerfeld, C. A.; Erbilgin, O. Trends Microbiol. 2015, 23, 22.
(2) Bobik, T. A.; Lehman, B. P.; Yeates, T. O. Mol. Microbiol. 2015, 98, 193.
(3) Axen, S. D.; Erbilgin, O.; Kerfeld, C. A. PLoS Comput. Biol. 2014, 10, e1003898.

(4) Klein, M. G.; Zwart, P.; Bagby. S. C.; Cai, F.; Chisholm, S. W.; Heinhorst. S.; Cannon, G. C.; Kerfeld, C. A. *J. Mol. Biol.* 2009, 392, 319.

(5) Sagermann. M.; Ohtaki, A.; Nikolakakis, K. *Proc. Natl. Acad. Sci. U.S.A.* 2009, 106, 8883.

(6) Tanaka, S.; Kerfeld, C. A.; Sawaya, M. R.; Cai. F.; Heinhorst, S.; Cannon. G. C.; Yeatcs. T. O. *Science* 2008, 319, 1083.

(7) Sutter. M.; Wilson, S. C.; Deutsch, S.; Kerfeld. C. A. *Photosynth. Res.* 2013, 118, 9.

(8) Wheatley, N. M.; Gidaniyan, S. D.; Liu, Y.; Cascio, D.; Yeates, T. O. *Protein Sci.* 2013, 22, 660.

(9) Kerfeld. C. A.; Sawaya. M. R.; Tanaka, S.; Nguyen, C. V.; Phillips, M.; Beeby, M.; Yeates. T. O. *Science* 2005, 309, 936.

(10) Kinney, J. N.; Axen, S. D.; Kerfeld, C. A. *Photosynth. Res.* 2011, 109, 21.

(11) Frank, S.; Lawrence, A. D.; Prentice. M. B.; Warren, M. J. *J. Biotechnol.* 2013, 163, 273.

(12) Parsons, J. B.; Dinesh. S. D.; Deery, E.; Leech, H. K.; Brindley, A. A.; Heldt, D.; Frank, S.; Smales, C. M.; Lunsdorf. H.; Rambach, A.; Gass, M. H.; Bleloch, A.; McClean, K. J.; Munro, A. W.; Rigby. S. E.; Warren, M. J.; Prentice, M. B. *J. Biol. Chem.* 2008, 283, 14366.

(13) Fan, C.; Cheng. S.; Liu. Y.; Escobar, C. M.; Crowley. C. S.; Jefferson, R. E.; Yeates, T. O. Bobik. T. A. *Proc. Natl. Acad. Sci. U.S.A.* 2010, 107, 7509.

(14) Lassila. J. K.; Bernstein, S. L.; Kinney. J. N.; Axen, S. D.; Kerfeld, C. A. *J. Mol. Biol.* 2014, 426, 2217.

(15) Lawrence, A. D.; Frank, S.; Newnham, S.; Lee, M. J.; Brown, I. R.; Xue, W. F.; Rowe, M. L.; Mulvihill, D. P.; Prentice, M. B.; Howard, M. J.; Warren. M. J. *ACS Synth. Biol.* 2014, 3, 454.

(16) Parsons, J. B.; Lawrence, A. D.; McLean, K. J.; Munro, A. W.; Rigby, S. E.; Warren, M. J. *PloS One* 2010, 5, e14009.

(17) Pang, A.; Warren, M. J.; Pickersgill, R. W. *Acta Crystallogr. D Biol. Crystallogr.* 2011, 67, 91.

(18) Thompson, M. C.; Wheatley, N. M.; Jorda. J.; Sawaya, M. R.; Gidaniyan, S. D.; Ahmed, H.; Yang, Z.; McCarty, K. N.; Whitelegge, J. P.; Yeates, T. O. *J. Mol. Biol.* 2014, 426, 3287.

(19) Beinert. H.; Holm, R. H.; Munck. E. *Science* 1997, 277, 653.

(20) Fontecave, M. *Nat. Chem. Biol.* 2006, 2, 171.

(21) Capozzi, F.; Ciurli, S.; Luchinat, C. In *Metal Sites in Proteins and Models Redox Centres*; Hill, H. A. O., Sadler, P. J., Thomson, A. J., Eds.; Springer Berlin Heidelberg: 1998; Vol. 90, p 127.

(22) Kuchenreuther. J. M.; Grady-Smith, C. S.; Bingham. A. S.; George. S. J.; Cramer. S. P.; Swartz, J. R. *PloS One* 2010, 5, e15491.

(23) Stookey, L. L. *Anal. Chem.* 1970, 42, 779.

(24) Kabsch, W. *Acta Crystallogr. D Biol. Crystallogr.* 2010, 66, 125.

(25) Winn, M. D.; Ballard, C. C.; Cowtan, K. D.; Dodson, E. J.; Emsley, P.; Evans, P. R.; Keegan, R. M.; Krissinel. E. B.; Leslie, A. G.; McCoy, A.; McNicholas, S. J. Murshudov. G. N.; Pannu, N. S.; Potterton, E. A.; Powell, H. R.; Read. R. J.; Vagin. A.; Wilson, K. S. *A Acta Crystallogr. D Biol. Crystallogr.* 2011, 67, 235.

(26) McCoy, A. J.; Grosse-Kunstleve, R. W.; Adams. P. D.; Winn. M. D.; Storoni, L. C.; Read, R. J. *J. Appl. Crystallogr.* 2007, 40, 658.

(27) Adams. P. D.; Afonine, P. V.; Bunkoczi, G.; Chen, V. B.; Davis, I. W.; Echols, N.; Headd, J. J.; Hung, L. W.; Kapral, G. J.; Grosse-Kunstleve, R. W.; McCoy. A. J.; Moriarty, N. W.; Oeffner, R.; Read, R. J.; Richardson, D. C.; Richardson, J. S.; Terwilliger, T. C.; Zwart, P. H. *Acta Crystallogr. D Biol. Crystallogr* 0.2010, 66, 213.

(28) Emsley, P.; Cowtan. K. *Acta Crystallogr. D Biol. Crystallogr.* 2004, 60, 2126.

(29) Stoll, S.; Schweiger, A. *J. Magn. Reson.* 2006, 178, 42.

(30) Dutton, P. L. *Methods Enzymol.* 1978, 54, 411.

(31) Petros, A. K.; Reddi. A. R.; Kennedy, M. L.; Hyslop, A. G.; Gibney, B. R. *Inorg. Chem.* 2006, 45, 9941.

(32) Stout. C. D. In *Encyclopedia of Inorganic and Bioinorganic Chemistry*; John Wiley & Sons. Ltd: Online, 2011.

(33) Giastas, P.; Pinotsis. N.; Efthymiou. G.; Wilmanns, M.; Kyritsis, P.; Moulis, J. M.; Mavridis, I. M. *J. Biol. Inorg. Chem.* 2006, 11, 445.

(34) Mitra, D.; George, S. J.; Guo, Y.; Kamali. S.; Keable, S.; Peters, J. W.; Pelmenschikov, V.; Case, D. A.; Cramer. S. P. *J. Am. Chem. Soc.* 2013, 135, 2530.

(35) Herskovitz, T.; Averill, B. A.; Holm, R. H.; Ibers, J. A.; Phillips. W. D.; Weiher, J. F. *Proc. Natl. Acad. Sci. U.S.A.* 1972, 69, 2437.

(36) Fukuyama, K. In *Encyclopedia of Inorganic and Bioinorganic Chemistry*; John Wiley & Sons, Ltd: Online, 2011.

(37) Sweeney, W. V.; Rabinowitz, J. C. *Annu. Rev. Biochem.* 1980, 49, 139.

(38) Lippard. S. J.; Berg. J. M. In *Principles of Bioinorganic Chemistry*; University Science Books: Mill Valley, Calif., 1994.

(39) Mayhew, S. G. *Eur J. Biochem* 1978, 85, 535.

(40) Lanz, N. D.; Grove, T. L.; Gogonea, C. B.; Lee, K. H.; Krebs, C.; Booker. S. *J. Methods Enzymol.* 2012, 516, 125.

(41) Guigliarelli. B.; Bertrand, P. *Adv. Inorg. Chem.* 1999. Volume 47, 421.

(42) Cleland. W. W. *Biochemistry* 1964, 3, 480.

(43) Roy, A.; Sommer. D. J.; Schmitz, R. A.; Brown, C. L.; Gust, D.; Astashkin, A.; Ghirlanda. G. *J. Am. Chem. Soc.* 2014, 136, 17343.

(44) Rouault, T. *Iron-Sulfur Clusters in Chemistry and Biology*; De Gruyter: Berlin, 2014.

(45) Broderick. J. B.; Duffus. B. R.; Duschene. K. S.; Shepard, E. M. *Chem. Rev.* 2014, 114, 4229.

(46) Robbins, A. H.; Stout. C. D. *Proc. Natl. Acad. Sci. U.S.A.* 1989, 86, 3639.

(47) Imlay, J. A. *Mol. Microbiol.* 2006, 59, 1073.

(48) Moura. J. J.; Macedo. A. L.; Palma. P. N. *Methods Enzymol.* 1994, 243, 165.

(49) Johnson. M. K.; Smith, A. D. In *Encyclopedia of Inorganic and Bioinorganic Chemistry*; John Wiley & Sons, Ltd: Online, 2011.

(50) Gibney, B. R.; Mulholland. S. E.; Rabanal. F.; Dutton. P. L. *Proc. Natl. Acad. Sci. U.S.A.* 1996, 93, 15041.

(51) Antonkine. M. L.; Koay. M. S.; Epel, B.; Breitenstein. C.; Gopta, O.; Gartner, W.; Bill, E.; Lubitz, W. *Biochim. Biophys. Acta* 2009, 1787, 995.

(52) Saridakis, E.; Giastas, P.; Efthymiou, G.; Thoma. V.; Moulis. J. M.; Kyritsis, P.; Mavridis, I. M. *J. Biol. Inorg. Chem.* 2009, 14, 783.

(53) Grzyb, J.; Xu, F.; Weiner. L.; Reijerse, E. J.; Lubitz, W.; Nanda, V.; Noy, D. *Biochim. Biophys. Acta* 2010, 1797, 406.

(54) Yu. F.; Cangelosi. V. M.; Zastrow. M. L.; Tegoni. M.; Plegaria. J. S.; Tebo, A. G.; Mocny, C. S.; Ruckthong, L.; Qayyum. H.; Pecoraro. V. L. *Chem. Rev.* 2014, 114, 3495.

(55) Nanda, V.; Rosenblatt, M. M.; Osyczka, A.; Kono, H.; Getahun. Z.; Dutton. P. L.; Saven, J. G.; Degrado, W. F. *J. Am. Chem. Soc.* 2005, 127, 5804.

(56) Hoppe, A.; Pandelia, M. E.; Gartner. W.; Lubitz, W. *B Biochim. Biophys. Acta* 2011, 1807, 1414.

(57) Coldren, C. D.; Hellinga, H. W.; Caradonna, J. P. *Proc. Natl. Acad. Sci. U.S.A.* 1997, 94, 6635.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The following statements of the invention are intended to describe and summarize various embodiments of the invention according to the foregoing description in the specification.

Statements:
1. A modified polypeptide comprising at least 95% sequence identity to SEQ ID NO: 1, 36, or 37 and with at least one amino acid substitution.
2. The modified polypeptide of statement 1, wherein the at least one amino acid substitution replaces an amino acid in the modified polypeptide with a cysteine.
3. The modified polypeptide of statement 1 or 2, wherein the at least one amino acid substitution replaces a serine, threonine, valine, leucine, isoleucine, methionine, aspartic acid, asparagine, alanine, arginine, aspartic acid, glutamic acid, glutamine, glycine, histidine, isoleucine, leucine, lysine, methionine, phenylalanine, proline, or tyrosine amino acid.
4. The modified polypeptide of statement 1, 2, or 3, wherein the at least one amino acid substitution replaces a serine, threonine, or proline with a cysteine; and/or wherein the at least one amino acid substitution replaces an isoleucine, arginine, or alanine with a phenylalanine.
5. The modified polypeptide of statement 1-3 or 4, wherein the at least one amino acid substitution replaces an amino acid (e.g. a serine, threonine, or proline) with a cysteine at an amino acid position corresponding to position 55 or 56 of the SEQ ID NO: 1 sequence; and/or wherein the at least one amino acid substitution replaces an amino acid (e.g. an isoleucine, arginine, or alanine) with a phenylalanine at an amino acid position corresponding to position 154 of the SEQ ID NO: 1 sequence.
6. The modified polypeptide of statement 1-4 or 5, wherein the modified polypeptide comprises at least 96%, or at least 97%, or at least 98%, or at least 99% sequence identity to SEQ ID NO: 1, 36, or 37.
7. The modified polypeptide of statement 1-5 or 6, wherein the modified polypeptide has at least 97% sequence identity to SEQ ID NO:3-8, 36 or 37.
8. The modified polypeptide of statement 1-6 or 7, which is a modified tandem BMC-T subunit.
9. The modified polypeptide of statement 1-7 or 8, which assembles into a microcompartment.
10. The modified polypeptide of statement 1-8 or 9, wherein the at least one amino acid substitution replaces an amino acid that has a side chain that extends into an interior of a microcompartment in which the modified polypeptide resides.
11. The modified polypeptide of statement 1-9 or 10, wherein the at least one amino acid substitution replaces an amino acid that has a side chain that extends into a pore of a microcompartment in which the modified polypeptide resides.
12. The modified polypeptide of statement 1-10 or 11, wherein the modified polypeptide assembles into a trimer.
13. The modified polypeptide of statement 1-11 or 12, wherein the modified polypeptide assembles into a microcompartment that is about 30-300 nm, or about 40-200 nm in diameter.
14. The modified polypeptide of statement 1-12 or 13, wherein the modified polypeptide assembles into a microcompartment within a host cell.
15. The modified polypeptide of statement 1-13 or 14, wherein the modified polypeptide assembles into a microcompartment within a prokaryotic host cell.
16. The modified polypeptide of statement 1-14 or 15, wherein the modified polypeptide assembles into a microcompartment within a bacterial host cell.
17. The modified polypeptide of statement 1-15 or 16, wherein the modified polypeptide assembles into a microcompartment within a *Haliangium ochraceum* or *Escherichia coli* host cell.
18. An expression cassette or expression vector comprising a promoter operably linked to a nucleotide segment that encodes the modified polypeptide of statement 1-16 or 17.
19. The expression cassette or expression vector of statement 18, wherein the nucleotide segment encoding the modified polypeptide has a sequence with at least 95% sequence identity to SEQ ID NO:2 and with at least one nucleotide substitution, or at least two nucleotide substitutions, or at least three nucleotide substitutions.
20. The expression cassette or expression vector of statement 18 or 19, wherein the promoter is a constitutively active promoter.
21. The expression cassette or expression vector of statement 18, 19, or 20, wherein the promoter is an inducible promoter.
22. The expression cassette or expression vector of statement 18-20, or 21, wherein the promoter is a prokaryotic promoter.
23. A microcompartment comprising the modified polypeptide of statement 1-16 or 17.
24. The microcompartment of statement 23, further comprising one or more iron atoms.
25. The microcompartment of statement 23 or 24, comprising one or more [4Fe-4S] clusters.
26. The microcompartment of statement 23, 24 or 25, comprising a series of BMC-T trimers.
27. The microcompartment of statement 23-25 or 26, comprising a series of BMC-T1 trimers, each BMC-T having a sequence comprising at least 95% sequence identity, each with SEQ ID NO:1, SEQ ID NO:3, SEQ ID NO:4, SEQ ID NO:5, SEQ ID NO:6. SEQ ID NO:7, or SEQ ID NO:8.
28. The microcompartment of statement 23-26 or 27, comprising one or more BMC-T2 trimer having a sequence comprising at least 95% sequence identity with SEQ ID NO:11.
29. The microcompartment of statement 23-27 or 28, comprising one or more BMC-T3 trimer having a sequence comprising at least 95% sequence identity with SEQ ID NO:13.

30. The microcompartment of statement 23-28, or 29, further comprising a series of BMC-H hexamers.
31. The microcompartment of statement 23-29 or 30, comprising a series of BMC-H hexamers, each BMC-H with a sequence comprising at least 95% sequence identity with SEQ ID NO:9.
32. The microcompartment of statement 23-30 or 31, further comprising a series of BMC-P pentamers.
33. The microcompartment of statement 23-31 or 32, further comprising further comprising a series of BMC-P pentamers, each BMC-P having a sequence comprising at least 95% sequence identity with SEQ ID NO: 15, SEQ ID NO:17, or SEQ ID NO:19.
34. The microcompartment of statement 23-32 or 33 comprising: a modified BMC-T subunit with sequence SEQ ID NO:3-7 or 8, a BMC-T subunit with sequence SEQ ID NO:11, a BMC-T subunit with sequence SEQ ID NO:13, a BMC-H subunit with sequence SEQ ID NO:9, a BMC-P subunit with sequence SEQ ID NO: 15, a BMC-P subunit with sequence SEQ ID NO: 17, and a BMC-P subunit with sequence SEQ ID NO: 19.
35. The microcompartment of statement 23-33, or 34, which exhibit a reduction potential of −500 to −200 mV or −455 to −370 mV versus the Standard Hydrogen Electrode (SHE).
36. The microcompartment of statement 23-34 or 35, which is stable through redox cycling.
37. The microcompartment of statement 23-35 or 36, further comprising an encapsulated enzyme.
38. The microcompartment of statement 23-36 or 37, further comprising an encapsulated nitrogenase.
39. The microcompartment of statement 23-37 or 38, further comprising an enzyme of a methylerythritol 4-phosphate (MEP) pathway.
40. The microcompartment of statement 23-37 or 39, further comprising an IspG and/or IspH enzyme,
41. The microcompartment of statement 23-39 or 40, further comprising an enzyme that can catalyze the conversion of NAD/NADP.
42. A method comprising transforming a host cell with an expression cassette or expression vector comprising a promoter operably linked to a nucleotide segment that encodes the modified polypeptide of statement 1-16 or 17, and culturing the host cell in a culture medium.
43. The method of statement 42, comprising growing the host cell to generate a population of host cells.
44. The method of statement 42 or 43, comprising growing the host cell to generate a population of host cells and culturing the population of host cells in a bioreactor.
45. A method comprising culturing a host cell comprising the microcompartment of statement 23-40 or 41.
46. The method of statement 45, comprising growing the host cell to generate a population of host cells.
47. The method of statement 45 or 46, comprising growing the host cell to generate a population of host cells and culturing the population of host cells in a bioreactor.
48. A method comprising incubating the modified polypeptide of statement 1-16 or 17 with an iron III ($Fe^{+3}$) salt.
49. The method of statement 48 further comprising incubating the modified polypeptide with sulfur (e.g $Na_2S$) to generate a modified polypeptide with Fe—S clusters.
50. The method of statement 49, further comprising separating the modified polypeptide with Fe—S clusters from impurities such as salts, excess iron III ($Fe^{+3}$), excess sulfur, or a combination thereof.
51. A method comprising (a) culturing in a culture medium a population of host cells comprising an expression cassette or expression vector comprising a promoter operably linked to a nucleotide segment that encodes the modified polypeptide of statement 1-16 or 17, wherein the host cell also comprises an endogenous gene or a heterologous expression cassette that encodes an enzyme or a product; and (b) isolating microcompartments from the population.
52. The method of statement 51, wherein the enzyme catalyzes an oxidation reaction.
53. The method of statement 51 or 52, wherein the enzyme is an aldehyde dehydrogenase, alcohol dehydrogenase, or phospotransacylase.
54. The method of statement 51, 53, or 53, wherein the enzyme catalyzes one or more reduction/oxidation (redox) reaction.
55. The method of statement 51, 53, or 53, wherein the enzyme catalyzes one or more electron transfer reaction.
56. The method of statement 51-54 or 55, further comprising isolating the product from the microcompartments.
57. The method of statement 51-55 or 56, wherein the product is a small molecule.
58. The method of statement 51-56 or 57, wherein the product is a biofuel.
59. The method of statement 51-57 or 58, wherein the product is an alcohol, amine, alkanolamine, or a combination thereof.
60. The method of statement 51-58 or 59, wherein the product is a propanediol, ethanolamine, amino-2-propanol, or a combination thereof.

The specific compositions and methods described herein are representative, exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by embodiments and optional features, modification and variation of the concepts herein disclosed may be resorted to by those skilled in the art, and that such modifications and variations are considered to be within the scope of this invention as defined by the appended claims and statements of the invention.

The invention illustratively described herein may be practiced in the absence of any element or elements, or limitation or limitations, which is not specifically disclosed herein as essential. The methods and processes illustratively described herein may be practiced in differing orders of steps, and the methods and processes are not necessarily restricted to the orders of steps indicated herein or in the claims.

As used herein and in the appended claims, the singular forms "a." "an," and "the" include plural reference unless the context clearly dictates otherwise. Thus, for example, a reference to "a plant" or "a seed" or "a cell" includes a plurality of such plants, seeds or cells, and so forth. In this document, the term "or" is used to refer to a nonexclusive or, such that "A or B" includes "A but not B," "B but not A," and "A and B," unless otherwise indicated.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

The Abstract is provided to comply with 37 C.F.R. § 1.72(b) to allow the reader to quickly ascertain the nature and gist of the technical disclosure. The Abstract is submitted with the understanding that it will not be used to interpret or limit the scope or meaning of the claims.

What is claimed:

1. A bacterial microcompartment comprising a S55C-modified BMC-T1 polypeptide with a cysteine at position 55 and with at least 97% sequence identity to SEQ ID NO:3.

2. A host cell comprising the bacterial microcompartment of claim 1.

3. The bacterial microcompartment of claim 1, further comprising at least one BMC-H subunit.

4. The bacterial microcompartment of claim 1, further comprising at least one BMC-P subunit.

5. The bacterial microcompartment of claim 1, further comprising one or more BMC-T2 proteins.

6. The bacterial microcompartment of claim 1, further comprising one or more BMC-T3 proteins.

7. The bacterial microcompartment of claim 1, further comprising one or more iron atoms.

8. The bacterial microcompartment of claim 1, further one or more [4Fe-4S] clusters.

9. The bacterial microcompartment of claim 1, further comprising an enzyme.

10. The bacterial microcompartment of claim 9, wherein the enzyme catalyzes an oxidation reaction.

11. The bacterial microcompartment of claim 1, further comprising an enzyme that can catalyze the conversion of NAD/NADP.

* * * * *

SEQUENCE LISTING

```
<160> NUMBER OF SEQ ID NOS: 37

<210> SEQ ID NO 1
<211> LENGTH: 205
<212> TYPE: PRT
<213> ORGANISM: Haliangium ochraceum

<400> SEQUENCE: 1

Met Asp His Ala Pro Glu Arg Phe Asp Ala Thr Pro Pro Ala Gly Glu
1               5                   10                  15

Pro Asp Arg Pro Ala Leu Gly Val Leu Glu Leu Thr Ser Ile Ala Arg
            20                  25                  30

Gly Ile Thr Val Ala Asp Ala Ala Leu Lys Arg Ala Pro Ser Leu Leu
        35                  40                  45

Leu Met Ser Arg Pro Val Ser Ser Gly Lys His Leu Leu Met Met Arg
    50                  55                  60

Gly Gln Val Ala Glu Val Glu Glu Ser Met Ile Ala Ala Arg Glu Ile
65                  70                  75                  80

Ala Gly Ala Gly Ser Gly Ala Leu Leu Asp Glu Leu Glu Leu Pro Tyr
                85                  90                  95

Ala His Glu Gln Leu Trp Arg Phe Leu Asp Ala Pro Val Val Ala Asp
            100                 105                 110

Ala Trp Glu Glu Asp Thr Glu Ser Val Ile Ile Val Glu Thr Ala Thr
        115                 120                 125

Val Cys Ala Ala Ile Asp Ser Ala Asp Ala Ala Leu Lys Thr Ala Pro
    130                 135                 140

Val Val Leu Arg Asp Met Arg Leu Ala Ile Gly Ile Ala Gly Lys Ala
145                 150                 155                 160

Phe Phe Thr Leu Thr Gly Glu Leu Ala Asp Val Glu Ala Ala Ala Glu
                165                 170                 175

Val Val Arg Glu Arg Cys Gly Ala Arg Leu Leu Glu Leu Ala Cys Ile
            180                 185                 190

Ala Arg Pro Val Asp Glu Leu Arg Gly Arg Leu Phe Phe
        195                 200                 205

<210> SEQ ID NO 2
<211> LENGTH: 618
<212> TYPE: DNA
<213> ORGANISM: Haliangium ochraceum

<400> SEQUENCE: 2
atggaccacg ctccggaacg ctttgatgcg accccgccgg caggtgaacc ggaccgcccg      60
```

```
gcactgggtg tgctggaact gacctcaatt gctcgtggta tcaccgttgc ggatgcggcc    120
ctgaaacgtg caccgagtct gctgctgatg tcccgcccgg tcagctctgg caagcatctg    180
ctgatgatgc gtggccaggt ggcagaagtt gaagaatcaa tgattgcagc tcgcgaaatc    240
gctggtgcag gttcgggtgc tctgctggat gaactggaac tgccgtatgc cacgaacaa     300 ctgtggcgct ttctggacgc accggtggtt gcagatgcat gggaagaaga caccgaaagc    360
gtcattatcg tggaaaccgc gacggtgtgc gcggccattg atagtgccga cgcagctctg    420
aaaacggcac cggtcgtgct gcgtgatatg cgcctggcca ttggtatcgc tggcaaggcg    480
tttttcaccc tgacgggtga actggcagac gtggaagcgg ccgcagaagt tgtccgtgaa    540
cgttgcggtg cacgtctgct ggaactggca tgtatcgcac gcccggttga tgaactgcgt    600
ggccgcctgt ttttctaa                                                  618
```

<210> SEQ ID NO 3
<211> LENGTH: 205
<212> TYPE: PRT
<213> ORGANISM: Artificial Sequence
<220> FEATURE:
<223> OTHER INFORMATION: A synthetic amino acid sequence

<400> SEQUENCE: 3

```
Met Asp His Ala Pro Glu Arg Phe Asp Ala Thr Pro Pro Ala Gly Glu
1               5                   10                  15

Pro Asp Arg Pro Ala Leu Gly Val Leu Glu Leu Thr Ser Ile Ala Arg
            20                  25                  30

Gly Ile Thr Val Ala Asp Ala Ala Leu Lys Arg Ala Pro Ser Leu Leu
        35                  40                  45

Leu Met Ser Arg Pro Val Cys Ser Gly Lys His Leu Leu Met Met Arg
    50                  55                  60

Gly Gln Val Ala Glu Val Glu Glu Ser Met Ile Ala Ala Arg Glu Ile
65                  70                  75                  80

Ala Gly Ala Gly Ser Gly Ala Leu Leu Asp Glu Leu Glu Leu Pro Tyr
                85                  90                  95

Ala His Glu Gln Leu Trp Arg Phe Leu Asp Ala Pro Val Val Ala Asp
            100                 105                 110

Ala Trp Glu Glu Asp Thr Glu Ser Val Ile Ile Val Glu Thr Ala Thr
        115                 120                 125

Val Cys Ala Ala Ile Asp Ser Ala Asp Ala Ala Leu Lys Thr Ala Pro
130                 135                 140

Val Val Leu Arg Asp Met Arg Leu Ala Ile Gly Ile Ala Gly Lys Ala
145                 150                 155                 160

Phe Phe Thr Leu Thr Gly Glu Leu Ala Asp Val Glu Ala Ala Ala Glu
                165                 170                 175

Val Val Arg Glu Arg Cys Gly Ala Arg Leu Leu Glu Leu Ala Cys Ile
            180                 185                 190

Ala Arg Pro Val Asp Glu Leu Arg Gly Arg Leu Phe Phe
        195                 200                 205
```

<210> SEQ ID NO 4
<211> LENGTH: 205
<212> TYPE: PRT
<213> ORGANISM: Artificial Sequence
<220> FEATURE:
<223> OTHER INFORMATION: A synthetic amino acid sequence

<400> SEQUENCE: 4

Met Asp His Ala Pro Glu Arg Phe Asp Ala Thr Pro Pro Ala Gly Glu
1               5                   10                  15

Pro Asp Arg Pro Ala Leu Gly Val Leu Glu Leu Thr Ser Ile Ala Arg
            20                  25                  30

Gly Ile Thr Val Ala Asp Ala Ala Leu Lys Arg Ala Pro Ser Leu Leu
        35                  40                  45

Leu Met Ser Arg Pro Val Ser Cys Gly Lys His Leu Leu Met Met Arg
50                  55                  60

Gly Gln Val Ala Glu Val Glu Ser Met Ile Ala Ala Arg Glu Ile
65                  70                  75                  80

Ala Gly Ala Gly Ser Gly Ala Leu Leu Asp Glu Leu Glu Leu Pro Tyr
                85                  90                  95

Ala His Glu Gln Leu Trp Arg Phe Leu Asp Ala Pro Val Val Ala Asp
            100                 105                 110

Ala Trp Glu Glu Asp Thr Glu Ser Val Ile Ile Val Glu Thr Ala Thr
            115                 120                 125

Val Cys Ala Ala Ile Asp Ser Ala Asp Ala Ala Leu Lys Thr Ala Pro
        130                 135                 140

Val Val Leu Arg Asp Met Arg Leu Ala Ile Gly Ile Ala Gly Lys Ala
145                 150                 155                 160

Phe Phe Thr Leu Thr Gly Glu Leu Ala Asp Val Glu Ala Ala Ala Glu
                165                 170                 175

Val Val Arg Glu Arg Cys Gly Ala Arg Leu Leu Glu Leu Ala Cys Ile
            180                 185                 190

Ala Arg Pro Val Asp Glu Leu Arg Gly Arg Leu Phe Phe
            195                 200                 205

<210> SEQ ID NO 5
<211> LENGTH: 205
<212> TYPE: PRT
<213> ORGANISM: Artificial Sequence
<220> FEATURE:
<223> OTHER INFORMATION: A synthetic amino acid sequence

<400> SEQUENCE: 5

Met Asp His Ala Pro Glu Arg Phe Asp Ala Thr Pro Pro Ala Gly Glu
1               5                   10                  15

Pro Asp Arg Pro Ala Leu Gly Val Leu Glu Leu Thr Ser Ile Ala Arg
            20                  25                  30

Gly Ile Thr Val Ala Asp Ala Ala Leu Lys Arg Ala Pro Ser Leu Leu
        35                  40                  45

Leu Met Ser Arg Pro Val Cys Cys Gly Lys His Leu Leu Met Met Arg
50                  55                  60

Gly Gln Val Ala Glu Val Glu Ser Met Ile Ala Ala Arg Glu Ile
65                  70                  75                  80

Ala Gly Ala Gly Ser Gly Ala Leu Leu Asp Glu Leu Glu Leu Pro Tyr
                85                  90                  95

Ala His Glu Gln Leu Trp Arg Phe Leu Asp Ala Pro Val Val Ala Asp
            100                 105                 110

Ala Trp Glu Glu Asp Thr Glu Ser Val Ile Ile Val Glu Thr Ala Thr
            115                 120                 125

Val Cys Ala Ala Ile Asp Ser Ala Asp Ala Ala Leu Lys Thr Ala Pro
        130                 135                 140

Val Val Leu Arg Asp Met Arg Leu Ala Ile Gly Ile Ala Gly Lys Ala
145                 150                 155                 160

```
Phe Phe Thr Leu Thr Gly Glu Leu Ala Asp Val Glu Ala Ala Glu
            165                 170                 175

Val Val Arg Glu Arg Cys Gly Ala Arg Leu Leu Glu Leu Ala Cys Ile
            180                 185                 190

Ala Arg Pro Val Asp Glu Leu Arg Gly Arg Leu Phe Phe
            195                 200             205

<210> SEQ ID NO 6
<211> LENGTH: 205
<212> TYPE: PRT
<213> ORGANISM: Artificial Sequence
<220> FEATURE:
<223> OTHER INFORMATION: A synthetic amino acid sequence

<400> SEQUENCE: 6

Met Asp His Ala Pro Glu Arg Phe Asp Ala Thr Pro Pro Ala Gly Glu
1               5                   10                  15

Pro Asp Arg Pro Ala Leu Gly Val Leu Glu Leu Thr Ser Ile Ala Arg
            20                  25                  30

Gly Ile Thr Val Ala Asp Ala Ala Leu Lys Arg Ala Pro Ser Leu Leu
        35                  40                  45

Leu Met Ser Arg Pro Val Cys Ser Gly Lys His Leu Leu Met Met Arg
50                  55                  60

Gly Gln Val Ala Glu Val Glu Ser Met Ile Ala Ala Arg Glu Ile
65                  70                  75                  80

Ala Gly Ala Gly Ser Gly Ala Leu Leu Asp Glu Leu Glu Leu Pro Tyr
                85                  90                  95

Ala His Glu Gln Leu Trp Arg Phe Leu Asp Ala Pro Val Val Ala Asp
            100                 105                 110

Ala Trp Glu Glu Asp Thr Glu Ser Val Ile Ile Val Glu Thr Ala Thr
            115                 120                 125

Val Cys Ala Ala Ile Asp Ser Ala Asp Ala Ala Leu Lys Thr Ala Pro
        130                 135                 140

Val Val Leu Arg Asp Met Arg Leu Ala Phe Gly Ile Ala Gly Lys Ala
145                 150                 155                 160

Phe Phe Thr Leu Thr Gly Glu Leu Ala Asp Val Glu Ala Ala Glu
            165                 170                 175

Val Val Arg Glu Arg Cys Gly Ala Arg Leu Leu Glu Leu Ala Cys Ile
            180                 185                 190

Ala Arg Pro Val Asp Glu Leu Arg Gly Arg Leu Phe Phe
            195                 200             205

<210> SEQ ID NO 7
<211> LENGTH: 205
<212> TYPE: PRT
<213> ORGANISM: Artificial Sequence
<220> FEATURE:
<223> OTHER INFORMATION: A synthetic amino acid sequence

<400> SEQUENCE: 7

Met Asp His Ala Pro Glu Arg Phe Asp Ala Thr Pro Pro Ala Gly Glu
1               5                   10                  15

Pro Asp Arg Pro Ala Leu Gly Val Leu Glu Leu Thr Ser Ile Ala Arg
            20                  25                  30

Gly Ile Thr Val Ala Asp Ala Ala Leu Lys Arg Ala Pro Ser Leu Leu
        35                  40                  45

Leu Met Ser Arg Pro Val Ser Cys Gly Lys His Leu Leu Met Met Arg
```

```
                    50                  55                  60
Gly Gln Val Ala Glu Val Glu Ser Met Ile Ala Ala Arg Glu Ile
 65                  70                  75                  80

Ala Gly Ala Gly Ser Gly Ala Leu Leu Asp Glu Leu Glu Leu Pro Tyr
                     85                  90                  95

Ala His Glu Gln Leu Trp Arg Phe Leu Asp Ala Pro Val Val Ala Asp
                    100                 105                 110

Ala Trp Glu Glu Asp Thr Glu Ser Val Ile Ile Val Glu Thr Ala Thr
                    115                 120                 125

Val Cys Ala Ala Ile Asp Ser Ala Asp Ala Ala Leu Lys Thr Ala Pro
                    130                 135                 140

Val Val Leu Arg Asp Met Arg Leu Ala Phe Gly Ile Ala Gly Lys Ala
145                 150                 155                 160

Phe Phe Thr Leu Thr Gly Glu Leu Ala Asp Val Glu Ala Ala Ala Glu
                    165                 170                 175

Val Val Arg Glu Arg Cys Gly Ala Arg Leu Leu Glu Leu Ala Cys Ile
                    180                 185                 190

Ala Arg Pro Val Asp Glu Leu Arg Gly Arg Leu Phe Phe
                    195                 200                 205

<210> SEQ ID NO 8
<211> LENGTH: 205
<212> TYPE: PRT
<213> ORGANISM: Artificial Sequence
<220> FEATURE:
<223> OTHER INFORMATION: A synthetic amino acid sequence

<400> SEQUENCE: 8

Met Asp His Ala Pro Glu Arg Phe Asp Ala Thr Pro Pro Ala Gly Glu
  1                   5                  10                  15

Pro Asp Arg Pro Ala Leu Gly Val Leu Glu Leu Thr Ser Ile Ala Arg
                     20                  25                  30

Gly Ile Thr Val Ala Asp Ala Ala Leu Lys Arg Ala Pro Ser Leu Leu
                 35                  40                  45

Leu Met Ser Arg Pro Val Cys Cys Gly Lys His Leu Leu Met Met Arg
 50                  55                  60

Gly Gln Val Ala Glu Val Glu Ser Met Ile Ala Ala Arg Glu Ile
 65                  70                  75                  80

Ala Gly Ala Gly Ser Gly Ala Leu Leu Asp Glu Leu Glu Leu Pro Tyr
                     85                  90                  95

Ala His Glu Gln Leu Trp Arg Phe Leu Asp Ala Pro Val Val Ala Asp
                    100                 105                 110

Ala Trp Glu Glu Asp Thr Glu Ser Val Ile Ile Val Glu Thr Ala Thr
                    115                 120                 125

Val Cys Ala Ala Ile Asp Ser Ala Asp Ala Ala Leu Lys Thr Ala Pro
                    130                 135                 140

Val Val Leu Arg Asp Met Arg Leu Ala Phe Gly Ile Ala Gly Lys Ala
145                 150                 155                 160

Phe Phe Thr Leu Thr Gly Glu Leu Ala Asp Val Glu Ala Ala Ala Glu
                    165                 170                 175

Val Val Arg Glu Arg Cys Gly Ala Arg Leu Leu Glu Leu Ala Cys Ile
                    180                 185                 190

Ala Arg Pro Val Asp Glu Leu Arg Gly Arg Leu Phe Phe
                    195                 200                 205
```

<210> SEQ ID NO 9
<211> LENGTH: 99
<212> TYPE: PRT
<213> ORGANISM: Haliangium ochraceum

<400> SEQUENCE: 9

Met Ala Asp Ala Leu Gly Met Ile Glu Val Arg Gly Phe Val Gly Met
1               5                   10                  15

Val Glu Ala Ala Asp Ala Met Val Lys Ala Ala Lys Val Glu Leu Ile
            20                  25                  30

Gly Tyr Glu Lys Thr Gly Gly Tyr Val Thr Ala Val Val Arg Gly
        35                  40                  45

Asp Val Ala Ala Val Lys Ala Ala Thr Glu Ala Gly Gln Arg Ala Ala
    50                  55                  60

Glu Arg Val Gly Glu Val Val Ala Val His Val Ile Pro Arg Pro His
65                  70                  75                  80

Val Asn Val Asp Ala Ala Leu Pro Leu Gly Arg Thr Pro Gly Met Asp
                85                  90                  95

Lys Ser Ala

<210> SEQ ID NO 10
<211> LENGTH: 300
<212> TYPE: DNA
<213> ORGANISM: Haliangium ochraceum

<400> SEQUENCE: 10
atggcggacg cactgggtat gattgaagtt cgtggttttg ttggtatggt ggaagcggcg      60
gatgctatgg tgaaagcggc taaagttgaa ctgattggtt atgaaaaaac cggcggtggc     120
tacgtgacgg cagtggttcg tggtgatgtc gcagcagtta aggcagctac cgaagcggt      180 cagcgtgcag cagaacgtgt tggtgaagtc gtggcagttc atgtcatccc gcgtccgcac     240
gtgaacgttg atgcagctct gccgctgggt cgtacgccgg gtatggacaa aagcgcgtaa     300

<210> SEQ ID NO 11
<211> LENGTH: 206
<212> TYPE: PRT
<213> ORGANISM: Haliangium ochraceum

<400> SEQUENCE: 11

Met Glu Leu Arg Ala Tyr Thr Val Leu Asp Ala Leu Gln Pro Gln Leu
1               5                   10                  15

Val Ala Phe Leu Gln Thr Val Ser Thr Gly Phe Met Pro Met Glu Gln
            20                  25                  30

Gln Ala Ser Val Leu Val Glu Ile Ala Pro Gly Ile Ala Val Asn Gln
        35                  40                  45

Leu Thr Asp Ala Ala Leu Lys Ala Thr Arg Cys Gln Pro Gly Leu Gln
    50                  55                  60

Ile Val Glu Arg Ala Tyr Gly Leu Ile Glu Met His Asp Asp Gln
65                  70                  75                  80

Gly Gln Val Arg Ala Ala Gly Asp Ala Met Leu Ala His Leu Gly Ala
                85                  90                  95

Arg Glu Ala Asp Arg Leu Ala Pro Arg Val Val Ser Ser Gln Ile Ile
                100                 105                 110

Thr Gly Ile Asp Gly His Gln Ser Gln Leu Ile Asn Arg Met Arg His
            115                 120                 125

Gly Asp Met Ile Gln Ala Gly Gln Thr Leu Tyr Ile Leu Glu Val His
        130                 135                 140

Pro Ala Gly Tyr Ala Ala Leu Ala Ala Asn Glu Ala Glu Lys Ala Ala
145                 150                 155                 160

Pro Ile Lys Leu Leu Glu Val Val Thr Phe Gly Ala Phe Gly Arg Leu
            165                 170                 175

Trp Leu Gly Gly Gly Glu Ala Glu Ile Ala Glu Ala Ala Arg Ala Ala
            180                 185                 190

Glu Gly Ala Leu Ala Gly Leu Ser Gly Arg Asp Asn Arg Gly
        195                 200                 205

<210> SEQ ID NO 12
<211> LENGTH: 621
<212> TYPE: DNA
<213> ORGANISM: Haliangium ochraceum

<400> SEQUENCE: 12
atggaactgc gtgcttatac ggtcctggat gccctgcagc cgcaactggt cgcctttctg      60
caaacggtgt caacgggttt catgccgatg aacagcaag cgagcgttct ggtcgaaatt     120
gcaccgggta tcgctgtcaa ccagctgacc gacgcagcac tgaaagcaac gcgttgccag     180
ccgggtctgc aaattgtgga acgtgcgtat ggcctgatcg aaatgcatga tgacgatcag     240
ggtcaagttc gtgcagctgg tgacgcaatg ctggcacacc tgggtgcacg tgaagctgat     300
cgtctggcac gcgtgtggt tagctctcag attatcaccg gtattgacgg ccatcagagt     360
caactgatca accgtatgcg ccacggtgat atgattcagg caggccaaac gctgtatatc     420
ctggaagttc atccggcagg ttacgcagca ctggcagcta atgaagccga aaaagcggcc     480
ccgattaagc tgctggaagt cgtgaccttt ggtgcattcg gtcgtctgtg gctgggtggt     540
ggtgaagcag aaatcgcaga agcagctcgt gcggcagaag gtgcactggc tggtctgtcc     600
ggccgtgata atcgcggcta a                                              621

<210> SEQ ID NO 13
<211> LENGTH: 212
<212> TYPE: PRT
<213> ORGANISM: Haliangium ochraceum

<400> SEQUENCE: 13

Met Ser Ile Thr Leu Arg Thr Tyr Ile Phe Leu Asp Ala Leu Gln Pro
1               5                   10                  15

Gln Leu Ala Thr Phe Ile Gly Lys Thr Ala Arg Gly Phe Leu Pro Val
            20                  25                  30

Pro Gly Gln Ala Ser Leu Trp Val Glu Ile Ala Pro Gly Ile Ala Ile
        35                  40                  45

Asn Arg Val Thr Asp Ala Ala Leu Lys Ala Thr Lys Val Gln Pro Ala
    50                  55                  60

Val Gln Val Val Glu Arg Ala Tyr Gly Leu Leu Glu Val His His Phe
65                  70                  75                  80

Asp Gln Gly Glu Val Leu Ala Ala Gly Ser Thr Ile Leu Asp Lys Leu
                85                  90                  95

Glu Val Arg Glu Glu Gly Arg Leu Lys Pro Gln Val Met Thr His Gln
            100                 105                 110

Ile Ile Arg Ala Val Glu Ala Tyr Gln Thr Gln Ile Ile Asn Arg Asn
        115                 120                 125

Ser Gln Gly Met Met Ile Leu Pro Gly Glu Ser Leu Phe Ile Leu Glu
    130                 135                 140

Thr Gln Pro Ala Gly Tyr Ala Val Leu Ala Ala Asn Glu Ala Glu Lys

|     |     |     |     | 145 |     |     |     |     | 150 |     |     |     |     | 155 |     |     |     |     | 160 |
| --- | --- | --- | --- | --- | --- | --- | --- | --- | --- | --- | --- | --- | --- | --- | --- | --- | --- | --- | --- |
| Ala | Ala | Asn | Val | His | Leu | Val | Asn | Val | Thr | Pro | Tyr | Gly | Ala | Phe | Gly |

Ala Ala Asn Val His Leu Val Asn Val Thr Pro Tyr Gly Ala Phe Gly
            165                 170                 175

Arg Leu Tyr Leu Ala Gly Ser Glu Ala Glu Ile Asp Ala Ala Glu
        180                 185                 190

Ala Ala Glu Ala Ala Ile Arg Ser Val Ser Gly Val Ala Gln Glu Ser
        195                 200                 205

Phe Arg Asp Arg
    210

<210> SEQ ID NO 14
<211> LENGTH: 639
<212> TYPE: DNA
<213> ORGANISM: Haliangium ochraceum

<400> SEQUENCE: 14

```
atgtcaatca ccctgcgcac ctatatcttt ctggacgccc tgcaaccgca actggcaacc    60
ttcatcggca aaacggctcg tggcttcctg ccggtcccgg gtcaggcaag cctgtgggtg   120
gaaattgctc cgggtattgc gatcaaccgt gtgaccgatg cggccctgaa agctacgaag   180
gtgcagccgg cggttcaagt ggttgaacgc gcgtatggcc tgctggaagt tcatcacttc   240
gatcagggcg aagtcctggc agctggtagt accatcctgg acaaactgga agttcgtgaa   300
gaaggtcgcc tgaagccgca ggtgatgacc atcaaatta tccgtgctgt tgaagcgtat   360
cagacgcaaa ttatcaaccg caatagtcag ggcatgatga ttctgccggg tgaatccctg   420
tttatcctgg aaacccaacc ggcaggttac gcagtcctgg cagccaatga agccgaaaaa   480
gcagctaacg ttcacctggt caatgtgacg ccgtatggcg cattcggtcg tctgtacctg   540
gccggctcag aagcagaaat tgatgcggcc gcagaagctg cggaagccgc aatccgcagc   600
gtttctggtg tcgcgcagga atcgtttcgt gaccgctaa                           639
```

<210> SEQ ID NO 15
<211> LENGTH: 92
<212> TYPE: PRT
<213> ORGANISM: Haliangium ochraceum

<400> SEQUENCE: 15

Met Tyr Leu Gly Arg Val Ile Gly Thr Val Val Ala Glu Arg Lys Val
1               5                   10                  15

Ala Gly Leu Glu Gly Ala Lys Leu Leu Leu Val Gln Pro Leu Asp Asp
            20                  25                  30

Ala Leu Ser Pro Val Gly Gly Val Gln Ala Ala Val Asp Thr Val Gln
        35                  40                  45

Ala Gly Pro Asp Asp Leu Val Tyr Leu Val Gly Ser Arg Glu Ala Ala
    50                  55                  60

Leu Ala Leu Thr Pro Ser Phe Val Pro Val Asp Ala Ala Ile Val Gly
65                  70                  75                  80

Ile Val Asp Asp Val His Ala Pro Glu Arg Ala Ser
                85                  90

<210> SEQ ID NO 16
<211> LENGTH: 279
<212> TYPE: DNA
<213> ORGANISM: Haliangium ochraceum

<400> SEQUENCE: 16

```
atgtatctgg gtcgtgtgat tggtaccgtg gtggctgaac gcaaagtggc gggtctggaa    60
```

```
ggcgcaaaac tgctgctggt gcaaccgctg gatgacgcac tgagtccggt cggtggtgtg     120
caggcagcag ttgataccgt ccaagcaggt ccggatgacc tggtgtatct ggttggtagc     180
cgtgaagcag ctctggcgct gacgccgtct tttgtgccgg ttgatgcggc cattgtcggc     240
atcgttgatg acgtgcatgc accggaacgc gctagctaa                            279
```

```
<210> SEQ ID NO 17
<211> LENGTH: 127
<212> TYPE: PRT
<213> ORGANISM: Haliangium ochraceum

<400> SEQUENCE: 17

Met Arg Leu Cys Arg Val Leu Gly Ser Val Val Ala Thr Val Lys His
1               5                   10                  15

Pro Val Tyr Asn Gly Leu Pro Leu Met Ile Val Gln Pro Leu Asp Asp
            20                  25                  30

Ala Gly Arg Asp Ala Gly Ala Ser Phe Leu Ala Val Asp Asn Val Gln
        35                  40                  45

Ser Gly Pro Gly Asp Arg Val Leu Val Leu Thr Glu Gly Gly Gly Val
    50                  55                  60

Arg Gln Ile Leu Ala Leu Gly Asp Gln Val Pro Ile Arg Ser Leu Ile
65                  70                  75                  80

Val Gly Val Val Asp Ala Val Asp Gly Val Ala Ala Thr Gly Val Asp
                85                  90                  95

Asp Ala Gly Gly Ala Ala Asp Ser Ala Ala Ala Lys Ser Val Arg
            100                 105                 110

Ala Asp Glu Leu Pro Ala Asp Ala Ser Ala Ala Gly Arg Gly Glu
        115                 120                 125
```

```
<210> SEQ ID NO 18
<211> LENGTH: 384
<212> TYPE: DNA
<213> ORGANISM: Haliangium ochraceum

<400> SEQUENCE: 18
atgcgtctgt gtcgtgttct gggctccgtc gtcgccaccg tcaagcaccc ggtctacaat      60
ggtctgccgc tgatgatcgt tcaaccgctg gatgacgcag tcgtgatgc aggcgctagt     120 tttctggctg ttgataacgt ccagtccggt ccgggtgacc gtgtcctggt gctgaccgaa     180
ggtggtggtg tgcgtcagat tctggcactg ggtgatcaag tcccgattcg cagcctgatc     240
gtgggcgtgg ttgatgcagt ggacggtgtt gcagcaacgg tgttgatga cgcaggtggt     300 gcagctgata gcgcagcagc agctaaatct gtccgtgcag atgaactgcc ggcagacgca     360
agcgcggccg gtcgcggcga ataa                                            384
```

```
<210> SEQ ID NO 19
<211> LENGTH: 96
<212> TYPE: PRT
<213> ORGANISM: Haliangium ochraceum

<400> SEQUENCE: 19

Met Val Leu Gly Lys Val Val Gly Thr Val Val Ala Ser Arg Lys Glu
1               5                   10                  15

Pro Arg Ile Glu Gly Leu Ser Leu Leu Leu Val Arg Ala Cys Asp Pro
            20                  25                  30

Asp Gly Thr Pro Thr Gly Gly Ala Val Val Cys Ala Asp Ala Val Gly
        35                  40                  45
```

```
Ala Gly Val Gly Glu Val Val Leu Tyr Ala Ser Gly Ser Ser Ala Arg
     50                  55                  60

Gln Thr Glu Val Thr Asn Asn Arg Pro Val Asp Ala Thr Ile Met Ala
 65                  70                  75                  80

Ile Val Asp Leu Val Glu Met Gly Gly Asp Val Arg Phe Arg Lys Asp
                 85                  90                  95

<210> SEQ ID NO 20
<211> LENGTH: 291
<212> TYPE: DNA
<213> ORGANISM: Haliangium ochraceum

<400> SEQUENCE: 20
atggtcctgg gtaaagtcgt gggtacggtg gtggcgagcc gcaaagaacc gcgcattgaa      60
ggtctgagcc tgctgctggt ccgtgcctgc gatccggacg gtaccccgac gggtggtgca     120
gtggtttgtg cagatgcagt gggtgcaggt gttggtgaag tcgtgctgta tgcgagtggc     180
agctctgccc gtcagaccga agtcacgaac aatcgcccgg ttgatgcaac cattatggct     240
atcgttgacc tggtcgaaat gggcggtgat gtgcgttttc gcaaagacta a              291

<210> SEQ ID NO 21
<211> LENGTH: 28
<212> TYPE: DNA
<213> ORGANISM: Artificial Sequence
<220> FEATURE:
<223> OTHER INFORMATION: A synthetic nucleic acid sequence

<400> SEQUENCE: 21
tctagagaaa gaggagaaat actagatg                                         28

<210> SEQ ID NO 22
<211> LENGTH: 31
<212> TYPE: DNA
<213> ORGANISM: Artificial Sequence
<220> FEATURE:
<223> OTHER INFORMATION: A synthetic nucleic acid sequence

<400> SEQUENCE: 22
tctagagatt aaagaggaga atactagat g                                      31

<210> SEQ ID NO 23
<211> LENGTH: 30
<212> TYPE: DNA
<213> ORGANISM: Artificial Sequence
<220> FEATURE:
<223> OTHER INFORMATION: A synthetic nucleic acid sequence

<400> SEQUENCE: 23
tctagagtca cacaggaaac ctactagatg                                       30

<210> SEQ ID NO 24
<211> LENGTH: 3332
<212> TYPE: DNA
<213> ORGANISM: Haliangium ochraceum

<400> SEQUENCE: 24
aataattttg tttagagaaa gaggagaaat actagatggc ggacgcactg ggtatgattg      60
aagttcgtgg ttttgttggt atggtggaag cggcggatgc tatggtgaaa gcggctaaag     120
ttgaactgat tggttatgaa aaaccggcg gtggctacgt gacggcagtg gttcgtggtg      180
atgtcgcagc agttaaggca gctaccgaag ccggtcagcg tgcagcagaa cgtgttggtg     240
```

```
aagtcgtggc agttcatgtc atcccgcgtc cgcacgtgaa cgttgatgca gctctgccgc      300
tgggtcgtac gccgggtatg gacaaaagcg cgtaatttag agattaaaga ggagaaatac      360
tagatggacc acgctccgga acgctttgat gcgaccccgc cggcaggtga accggaccgc      420
ccggcactgg gtgtgctgga actgacctca attgctcgtg gtatcaccgt tgcggatgcg      480
gccctgaaac gtgcaccgag tctgctgctg atgtcccgcc cggtcagctc tggcaagcat      540
ctgctgatga tgcgtggcca ggtggcagaa gttgaagaat caatgattgc agctcgcgaa      600
atcgctggtg caggttcggg tgctctgctg gatgaactgg aactgccgta tgcgcacgaa      660
caactgtggc gctttctgga cgcaccggtg gttgcagatg catgggaaga agacaccgaa      720
agcgtcatta tcgtggaaac cgcgacggtg tgcgcggcca ttgatagtgc cgacgcagct      780
ctgaaaacgg caccggtcgt gctgcgtgat atgcgcctgg ccattggtat cgctggcaag      840 gcgttttttca ccctgacggg tgaactggca gacgtggaag cggccgcaga agttgtccgt      900
gaacgttgcg gtgcacgtct gctggaactg gcatgtatcg cacgcccggt tgatgaactg      960
cgtggccgcc tgtttttcta atttagagat taaagaggag aaatactaga tggaactgcg     1020
tgcttatacg gtcctggatg ccctgcagcc gcaactggtc gccttttctgc aaacggtgtc     1080 aacgggtttc atgccgatgg aacagcaagc gagcgttctg gtcgaaattg caccgggtat     1140
cgctgtcaac cagctgaccg acgcagcact gaaagcaacg cgttgccagc cgggtctgca     1200
aattgtggaa cgtgcgtatg gcctgatcga aatgcatgat gacgatcagg gtcaagttcg     1260
tgcagctggt gacgcaatgc tggcacacct gggtgcacgt gaagctgatc gtctggcacc     1320
gcgtgtggtt agctctcaga ttatcaccgg tattgacggc catcagagtc aactgatcaa     1380
ccgtatgcgc cacggtgata tgattcaggc aggccaaacg ctgtatatcc tggaagttca     1440
tccggcaggt tacgcagcac tggcagctaa tgaagccgaa aaagcggccc cgattaagct     1500
gctggaagtc gtgacctttg gtgcattcgg tcgtctgtgg ctgggtggtg gtgaagcaga     1560
aatcgcagaa gcagctcgtg cggcagaagg tgcactggct ggtctgtccg gccgtgataa     1620
tcgcggctaa tttagagatt aaagaggaga aatactagat gtcaatcacc ctgcgcacct     1680
atatctttct ggacgccctg caaccgcaac tggcaacctt catcggcaaa acggctcgtg     1740
gcttcctgcc ggtcccgggt caggcaagcc tgtgggtgga aattgctccg ggtattgcga     1800
tcaaccgtgt gaccgatgcg gccctgaaag ctacgaaggt gcagccggcg gttcaagtgg     1860
ttgaacgcgc gtatggcctg ctggaagttc atcacttcga tcagggcgaa gtcctggcag     1920
ctggtagtac catcctggac aaactggaag ttcgtgaaga aggtcgcctg aagccgcagg     1980
tgatgaccca tcaaattatc cgtgctgttg aagcgtatca gacgcaaatt atcaaccgca     2040
atagtcaggg catgatgatt ctgccggggtg aatccctgtt tatcctggaa acccaaccgg     2100
caggttacgc agtcctggca gccaatgaag ccgaaaaagc agctaacgtt cacctggtca     2160
atgtgacgcc gtatggcgca ttcggtcgtc tgtacctggc cggctcagaa gcagaaattg     2220
atgcggccgc agaagctgcg gaagccgcaa tccgcagcgt ttctggtgtc gcgcaggaat     2280
cgtttcgtga ccgctaattt agagtcacac aggaaaccta ctagatgtat ctgggtcgtg     2340
tgattggtac cgtggtggct gaacgcaaag tggcgggtct ggaaggcgca aaactgctgc     2400
tggtgcaacc gctggatgac gcactgagtc cggtcggtgg tgtgcaggca gcagttgata     2460
ccgtccaagc aggtccggat gacctggtgt atctggttgg tagccgtgaa gcagctctgg     2520
cgctgacgcc gtcttttgtg ccggttgatg cggccattgt cggcatcgtt gatgacgtgc     2580
```

```
atgcaccgga acgcgctagc taatttagag tcacacagga aacctactag atgcgtctgt    2640
gtcgtgttct gggctccgtc gtcgccaccg tcaagcaccc ggtctacaat ggtctgccgc    2700
tgatgatcgt tcaaccgctg gatgacgcag gtcgtgatgc aggcgctagt tttctggctg    2760
ttgataacgt ccagtccggt ccgggtgacc gtgtcctggt gctgaccgaa ggtggtggtg    2820
tgcgtcagat tctggcactg ggtgatcaag tcccgattcg cagcctgatc gtgggcgtgg    2880
ttgatgcagt ggacggtgtt gcagcaacgg gtgttgatga cgcaggtggt gcagctgata    2940
gcgcagcagc agctaaatct gtccgtgcag atgaactgcc ggcagacgca agcgcggccg    3000
gtcgcggcga ataatttaga gtcacacagg aaacctacta gatggtcctg ggtaaagtcg    3060
tgggtacggt ggtggcgagc cgcaaagaac gcgcattga aggtctgagc ctgctgctgg     3120
tccgtgcctg cgatccggac ggtaccccga cgggtggtgc agtggtttgt gcagatgcag    3180
tgggtgcagg tgttggtgaa gtcgtgctgt atgcgagtgg cagctctgcc cgtcagaccg    3240
aagtcacgaa caatcgcccg gttgatgcaa ccattatggc tatcgttgac ctggtcgaaa    3300
tgggcggtga tgtgcgtttt cgcaaagact aa                                  3332

<210> SEQ ID NO 25

<400> SEQUENCE: 25

000

<210> SEQ ID NO 26
<211> LENGTH: 297
<212> TYPE: PRT
<213> ORGANISM: Rhizobium phaseoli

<400> SEQUENCE: 26

Met Ser Asp Leu Arg Gln Ile Ala Phe Tyr Gly Lys Gly Gly Ile Gly
1               5                   10                  15

Lys Ser Thr Thr Ser Gln Asn Thr Leu Ala Ala Leu Val Asp Leu Gly
            20                  25                  30

Gln Lys Ile Leu Ile Val Gly Cys Asp Pro Lys Ala Asp Ser Thr Arg
        35                  40                  45

Leu Ile Leu Asn Ala Lys Ala Gln Asp Thr Val Leu His Leu Ala Ala
    50                  55                  60

Gln Glu Gly Ser Val Glu Asp Leu Glu Leu Glu Asp Val Leu Lys Ala
65                  70                  75                  80

Gly Tyr Lys Gly Ile Lys Cys Val Glu Ser Gly Gly Pro Glu Pro Gly
                85                  90                  95

Val Gly Cys Ala Gly Arg Gly Val Ile Thr Ser Ile Asn Phe Leu Glu
            100                 105                 110

Glu Asn Gly Ala Tyr Asp Asp Val Asp Tyr Val Ser Tyr Asp Val Leu
        115                 120                 125

Gly Asp Val Val Cys Gly Gly Phe Ala Met Pro Ile Arg Glu Asn Lys
    130                 135                 140

Ala Gln Glu Ile Tyr Ile Val Met Ser Gly Glu Met Met Ala Leu Tyr
145                 150                 155                 160

Ala Ala Asn Asn Ile Ala Lys Gly Ile Leu Lys Tyr Ala His Ser Gly
                165                 170                 175

Gly Val Arg Leu Gly Gly Leu Ile Cys Asn Glu Arg Gln Thr Asp Arg
            180                 185                 190

Glu Leu Asp Leu Ser Glu Ala Leu Ala Ala Arg Leu Asn Ser Lys Leu
        195                 200                 205
```

Ile His Phe Val Pro Arg Asp Asn Ile Val Gln His Ala Glu Leu Arg
    210                 215                 220

Lys Met Thr Val Ile Gln Tyr Ala Pro Asp Ser Lys Gln Ala Gly Glu
225                 230                 235                 240

Tyr Arg Ala Leu Ala Glu Lys Ile His Ala Asn Ser Gly Gln Gly Thr
                245                 250                 255

Ile Pro Thr Pro Ile Thr Met Glu Glu Leu Glu Asp Met Leu Leu Asp
                260                 265                 270

Phe Gly Ile Met Lys Ser Asp Glu Gln Met Leu Ala Glu Leu Gln Ala
                275                 280                 285

Lys Glu Ser Ala Val Val Ala Ala Gln
290                 295

<210> SEQ ID NO 27
<211> LENGTH: 291
<212> TYPE: PRT
<213> ORGANISM: Bacteroidales bacterium

<400> SEQUENCE: 27

Met Ser Lys Lys Ile Lys Gln Ile Ala Val Tyr Gly Lys Gly Gly Ile
1               5                   10                  15

Gly Lys Ser Thr Thr Thr Ser Asn Ile Ser Ala Ala Leu Val Glu Ala
                20                  25                  30

Gly His Lys Val Leu Gln Phe Gly Cys Asp Pro Lys Ser Asp Ser Thr
                35                  40                  45

Asn Thr Leu Arg Asp Gly Lys Tyr Ile Pro Thr Val Leu Asp Leu Leu
50                  55                  60

Arg Glu Lys Pro Lys Val Asp Ala His Glu Ala Ile Phe Gln Gly Phe
65                  70                  75                  80

Lys Gly Val Tyr Cys Val Glu Ala Gly Gly Pro Ala Pro Gly Val Gly
                85                  90                  95

Cys Ala Gly Arg Gly Ile Ile Thr Ala Val Glu Leu Leu Lys Ser Gln
                100                 105                 110

His Ile Phe Glu Glu Leu Asp Leu Asp Tyr Val Ile Tyr Asp Val Leu
                115                 120                 125

Gly Asp Val Val Cys Gly Gly Phe Ala Val Pro Ile Arg Glu Gly Ile
                130                 135                 140

Ala Glu His Val Phe Thr Val Ser Ser Ser Asp Phe Met Ser Ile Tyr
145                 150                 155                 160

Ala Ala Asn Asn Leu Met Lys Gly Ile Lys Lys Tyr Ser Asn Ser Gly
                165                 170                 175

Gly Ala Leu Phe Gly Gly Ile Ala Asn Ser Ile Asn Ser Ser Tyr
                180                 185                 190

Gln Arg Ala Ile Ile Asp Asp Phe Thr Gln Gln Thr Gly Thr Gln Val
                195                 200                 205

Val Glu Tyr Val Pro Arg Ser Ile Thr Val Thr Gln Ala Glu Leu Ser
                210                 215                 220

Gly Arg Thr Thr Ile Glu Ala Gln Pro Ile Ser Val Gln Ala Asp Ile
225                 230                 235                 240

Tyr Arg Ser Leu Ala Lys Lys Ile His Glu His Thr Glu Ser Arg Val
                245                 250                 255

Pro Thr Pro Leu Glu Ile Asp Ala Leu Arg Glu Trp Ser Ala Arg Trp
                260                 265                 270

Ala Asp Gln Leu Leu Ala Ile Glu Ala Gly Glu Val Arg Gly Thr Gln

Ala Gly Ile
    290

<210> SEQ ID NO 28
<211> LENGTH: 511
<212> TYPE: PRT
<213> ORGANISM: Gluconacetobacter diazotrophicus

<400> SEQUENCE: 28

Met Pro Gln Asn Val Asp Lys Ile Leu Asp His Ala Pro Leu Phe Arg
1               5                   10                  15

Glu Pro Glu Tyr Gln Glu Met Leu Ala Gly Lys Ala Lys Leu Glu Asn
            20                  25                  30

Met Pro Pro Ala Asp Lys Val Val Glu Ile Ala Asp Trp Thr Lys Ser
        35                  40                  45

Trp Glu Tyr Arg Glu Lys Asn Phe Ala Arg Glu Ser Leu Ser Val Asn
    50                  55                  60

Pro Ala Lys Ala Cys Gln Pro Leu Gly Ala Val Phe Val Ala Ser Gly
65                  70                  75                  80

Phe Glu Arg Thr Met Ser Phe Val His Gly Ser Gln Gly Cys Val Ala
                85                  90                  95

Tyr Tyr Arg Ser His Leu Ser Arg His Phe Lys Glu Pro Ser Ser Ala
            100                 105                 110

Val Ser Ser Ser Met Thr Glu Asp Ala Ala Val Phe Gly Gly Leu Asn
        115                 120                 125

Asn Met Val Asp Gly Leu Ala Asn Thr Tyr Lys Leu Tyr Asp Pro Lys
130                 135                 140

Met Ile Ala Val Ser Thr Thr Cys Met Ala Glu Val Ile Gly Asp Asp
145                 150                 155                 160

Leu His Ala Phe Ile Gln Thr Ala Lys Gly Lys Gly Ser Val Pro Glu
                165                 170                 175

Glu Phe Asp Val Pro Phe Ala His Thr Pro Ala Phe Val Gly Ser His
            180                 185                 190

Val Thr Gly Tyr Asp Asn Met Leu Lys Gly Ile Leu Glu His Phe Trp
        195                 200                 205

Lys Gly Arg Thr Pro Val Pro Asn Arg Ser Val Asn Ile Ile Pro Gly
    210                 215                 220

Phe Asp Gly Phe Ala Val Gly Asn Asn Arg Glu Leu Lys Arg Ile Leu
225                 230                 235                 240

Gly Met Met Gly Val Gln Tyr Thr Ile Leu Ser Asp Val Ser Asp Gln
                245                 250                 255

Phe Asp Thr Pro Ser Asp Gly Glu Tyr Arg Met Tyr Asp Gly Gly Thr
            260                 265                 270

Lys Ile Glu Ala Ala Arg Asp Ala Val Asn Ala Asp Tyr Thr Ile Ser
        275                 280                 285

Leu Gln Glu Tyr Cys Thr Pro Lys Thr Leu Glu Tyr Cys Gln Ser Phe
    290                 295                 300

Gly Gln Lys Thr Ala Ser Phe His Tyr Pro Leu Gly Ile Gly Ala Thr
305                 310                 315                 320

Asp Asp Leu Leu Gln Lys Leu Ser Glu Ile Ser Gly Lys Pro Val Pro
                325                 330                 335

Gln Glu Leu Glu Met Glu Arg Gly Arg Leu Val Asp Ala Leu Ala Asp
            340                 345                 350

```
Ser Gln Ala Tyr Leu His Gly Lys Thr Tyr Ala Ile Tyr Gly Asp Pro
        355                 360                 365

Asp Phe Val Tyr Gly Met Ala Arg Phe Ile Leu Glu Thr Gly Gly Glu
    370                 375                 380

Pro Lys His Cys Leu Ala Thr Asn Gly Ser Lys Ala Trp Glu Ala Gln
385                 390                 395                 400

Met Gln Glu Leu Phe Asp Ser Ser Pro Phe Gly Val Gly Cys Lys Ala
                405                 410                 415

Trp Gly Gly Lys Asp Leu Trp His Met Arg Ser Leu Leu Ala Thr Glu
                420                 425                 430

Lys Val Asp Leu Leu Ile Gly Asn Ser Tyr Gly Lys Tyr Leu Glu Arg
                435                 440                 445

Asp Thr Asp Thr Pro Leu Ile Arg Leu Met Phe Pro Ile Phe Asp Arg
    450                 455                 460

His His His His Arg Phe Pro Val Trp Gly Tyr Gln Gly Ala Leu Arg
465                 470                 475                 480

Val Leu Val Thr Leu Leu Asp Lys Ile Phe Asp Lys Leu Asp Asp Asp
                485                 490                 495

Thr Ile Gln Ala Gly Val Thr Asp Tyr Ser Phe Asp Leu Thr Arg
                500                 505                 510

<210> SEQ ID NO 29
<211> LENGTH: 460
<212> TYPE: PRT
<213> ORGANISM: Bacteroidales bacterium

<400> SEQUENCE: 29

Met Leu Leu Arg His Thr Thr Ala Gln Glu Ile Glu Arg Lys Ala Leu
1               5                   10                  15

Thr Ile Asn Pro Ala Lys Thr Cys Gln Pro Val Gly Ala Met Tyr Ala
                20                  25                  30

Ala Leu Gly Leu His Gly Cys Leu Pro His Ser His Gly Ser Gln Gly
            35                  40                  45

Cys Cys Ser Tyr His Arg Ser Ala Leu Thr Arg His Phe Lys Glu Pro
        50                  55                  60

Val Met Ala Ala Thr Ser Ser Phe Ser Glu Gly Ser Ser Val Phe Gly
65                  70                  75                  80

Gly Ser Ala Asn Leu Val Thr Ala Ile Glu Thr Ile Phe Thr Val Tyr
                85                  90                  95

Asn Pro Asp Val Val Ala Val His Thr Thr Cys Leu Ser Glu Thr Ile
                100                 105                 110

Gly Asp Asp Leu Thr Gln Ile Val Ser Lys Ala His Glu Asp Gly Leu
            115                 120                 125

Val Pro Glu Gly Lys Lys Val Ile Tyr Cys Asn Thr Pro Ser Tyr Val
        130                 135                 140

Gly Thr His Val Thr Gly Tyr Ser Asn Gln Val Ala Ala Phe Val Lys
145                 150                 155                 160

Phe Phe Ser Thr Ala Thr Pro Lys Lys Lys Asn Val Val Asn Leu Val
                165                 170                 175

Ala Gly Trp Met Glu Pro Ser Asp Met Arg Glu Ile Lys Arg Leu Ala
                180                 185                 190

Gln Glu Met Glu Ala Arg Ile Ile Leu Phe Pro Asp Met Ser Gly Val
            195                 200                 205

Leu Asp Ala Pro Leu Thr Gly Lys Phe Glu Met Tyr Pro Lys Gly Gly
        210                 215                 220
```

Thr Thr Gln Ala Gln Leu Ile Ala Thr Gly Asp Ser Lys Phe Thr Ile
225                 230                 235                 240

Gly Leu Gly Ala Tyr Thr Thr Glu Asp Ala Cys Val Lys Leu Glu Asn
            245                 250                 255

Lys Cys Lys Val Lys Phe Glu Val Val Glu Ile Pro Ile Gly Leu Lys
        260                 265                 270

Ala Thr Asp Arg Phe Ile Thr Ser Leu Ser Arg His Ala Asn Val Pro
    275                 280                 285

Val Pro Asp Ser Ile Thr Glu Glu Arg Gly Arg Leu Val Asp Leu Ile
290                 295                 300

Ala Asp Asn Ser Lys Tyr Phe Tyr Gly Lys Arg Val Ala Leu Phe Gly
305                 310                 315                 320

Asp Pro Asp Thr Leu Ile Pro Leu Thr Glu Phe Leu Leu Thr Leu Asp
            325                 330                 335

Met Lys Pro Val Tyr Ile Val Thr Gly Thr Pro Gly Lys His Phe Asp
            340                 345                 350

Glu Ser Met Lys Thr Leu Leu Ser Glu Lys Val Pro Glu Ala Lys Tyr
        355                 360                 365

Lys Ser Gly Pro Asn Ala Asp Met Phe Gln Leu His Gln Trp Ile Lys
370                 375                 380

Gln Glu Pro Val Asp Leu Leu Ile Gly Asn Thr Tyr Gly Lys Tyr Ile
385                 390                 395                 400

Ala Arg Asp Glu Asn Ile Pro Phe Val Arg Leu Gly Phe Pro Ile Val
            405                 410                 415

Asp Arg Ala Gly His Asn Tyr Phe Pro Asn Thr Gly Tyr Val Gly Ala
            420                 425                 430

Thr Asn Leu Val Ile Lys Ile Leu Glu Lys Glu Leu Asp His Leu Asp
            435                 440                 445

Arg Asn Cys Pro Asp Glu Lys Val Glu Trp Gln Leu
    450                 455                 460

<210> SEQ ID NO 30
<211> LENGTH: 384
<212> TYPE: PRT
<213> ORGANISM: Streptomyces clavuligerus

<400> SEQUENCE: 30

Met Thr Ala Ile Ser Leu Gly Met Pro Ser Val Pro Thr Lys Leu Ala
1               5                   10                  15

Asp Arg Arg Val Ser Arg Lys Ile Gln Val Gly Ser Val Ala Val Gly
            20                  25                  30

Gly Asp Ala Pro Val Ser Val Gln Ser Met Thr Thr Thr Arg Thr Ser
        35                  40                  45

Asp Ile Gly Ala Thr Leu Gln Gln Ile Ala Glu Leu Thr Ala Ser Gly
    50                  55                  60

Cys Gln Ile Val Arg Val Ala Cys Pro Thr Gln Asp Asp Ala Asp Ala
65                  70                  75                  80

Leu Ala Thr Ile Ala Arg Lys Ser Gln Ile Pro Val Ile Ala Asp Ile
                85                  90                  95

His Phe Gln Pro Lys Tyr Val Phe Ala Ala Ile Asp Ala Gly Cys Ala
            100                 105                 110

Ala Val Arg Val Asn Pro Gly Asn Ile Lys Gln Phe Asp Asp Lys Val
        115                 120                 125

Lys Glu Ile Ala Lys Ala Ala Ser Ala Ser Gly Thr Pro Ile Arg Ile

```
            130                 135                 140
Gly Val Asn Ala Gly Ser Leu Asp Ala Arg Leu Leu Lys Lys Tyr Gly
145                 150                 155                 160

Lys Ala Thr Pro Glu Ala Leu Val Glu Ser Ala Leu Trp Glu Ala Ser
                165                 170                 175

Leu Phe Glu Glu His Gly Phe Gln Asp Ile Lys Ile Ser Val Lys His
            180                 185                 190

Asn Asp Pro Val Val Met Val Asn Ala Tyr Arg Gln Leu Ala Ala Gln
        195                 200                 205

Cys Asp Tyr Pro Leu His Leu Gly Val Thr Glu Ala Gly Pro Ala Phe
    210                 215                 220

Gln Gly Thr Ile Lys Ser Ala Val Ala Phe Gly Ala Leu Leu Ser Glu
225                 230                 235                 240

Gly Ile Gly Asp Thr Ile Arg Val Ser Leu Ser Ala Pro Pro Ala Glu
                245                 250                 255

Glu Val Lys Val Gly Ile Gln Ile Leu Glu Ser Leu Asn Leu Arg Gln
            260                 265                 270

Arg Arg Leu Glu Ile Val Ser Cys Pro Ser Cys Gly Arg Ala Gln Val
        275                 280                 285

Asp Val Tyr Lys Leu Ala Asp Glu Val Thr Ala Gly Leu Glu Gly Met
    290                 295                 300

Glu Val Pro Leu Arg Val Ala Val Met Gly Cys Val Val Asn Gly Pro
305                 310                 315                 320

Gly Glu Ala Arg Glu Ala Asp Leu Gly Val Ala Ser Gly Asn Gly Lys
                325                 330                 335

Gly Gln Ile Phe Val Lys Gly Glu Val Ile Lys Thr Val Pro Glu Ala
            340                 345                 350

Lys Ile Val Glu Thr Leu Ile Glu Glu Ala Met Lys Ile Ala Glu Glu
        355                 360                 365

Met Glu Lys Ala Gly Val Met Ser Gly Glu Pro Gln Val Ser Ile Gly
    370                 375                 380

<210> SEQ ID NO 31
<211> LENGTH: 385
<212> TYPE: PRT
<213> ORGANISM: Streptomyces roseus

<400> SEQUENCE: 31

Met Thr Ala Ile Ser Leu Gly Met Pro Ala Val Pro Thr Lys Leu Ala
1               5                   10                  15

Asp Arg Arg Val Ser Arg Lys Ile Gln Val Gly Ser Val Ala Val Gly
                20                  25                  30

Gly Asp Ser Gln Ile Ser Val Gln Ser Met Thr Thr Thr Arg Thr Ser
            35                  40                  45

Asp Ile Gly Ala Thr Leu Gln Gln Ile Ala Glu Leu Thr Ala Ser Gly
        50                  55                  60

Cys Asp Ile Val Arg Val Ala Cys Pro Thr Gln Asp Ala Asp Ala
65                  70                  75                  80

Leu Ala Val Ile Ala Lys Lys Ser Gln Ile Pro Val Ile Ala Asp Ile
                85                  90                  95

His Phe Gln Pro Lys Tyr Val Phe Ala Ala Ile Asp Ala Gly Cys Ala
            100                 105                 110

Ala Val Arg Val Asn Pro Gly Asn Ile Lys Gln Phe Asp Asp Lys Val
        115                 120                 125
```

Lys Glu Ile Ala Arg Ala Ala Lys Asp Ala Gly Thr Pro Ile Arg Ile
    130                 135                 140

Gly Val Asn Ala Gly Ser Leu Asp Ala Arg Leu Leu Lys Lys Tyr Gly
145                 150                 155                 160

Lys Ala Thr Pro Glu Ala Leu Val Glu Ser Ala Leu Trp Glu Ala Ser
                165                 170                 175

Leu Phe Glu Glu His Gly Phe Ser Asp Ile Lys Ile Ser Val Lys His
            180                 185                 190

Asn Asp Pro Val Val Met Val Asn Ala Tyr Arg Gln Leu Ala Ala Gln
        195                 200                 205

Cys Glu Tyr Pro Leu His Leu Gly Val Thr Glu Ala Gly Pro Ala Phe
210                 215                 220

Gln Gly Thr Ile Lys Ser Ala Val Ala Phe Gly Ala Leu Leu Ser Glu
225                 230                 235                 240

Gly Ile Gly Asp Thr Ile Arg Val Ser Leu Ser Ala Pro Pro Val Glu
                245                 250                 255

Glu Val Lys Val Gly Ile Gln Ile Leu Glu Ser Leu Asn Leu Lys Pro
            260                 265                 270

Arg Arg Leu Glu Ile Val Ser Cys Pro Ser Cys Gly Arg Ala Gln Val
        275                 280                 285

Asp Val Tyr Lys Leu Ala Glu Glu Val Thr Ala Gly Leu Thr Gly Met
290                 295                 300

Glu Val Pro Leu Arg Val Ala Val Met Gly Cys Val Val Asn Gly Pro
305                 310                 315                 320

Gly Glu Ala Arg Glu Ala Asp Leu Gly Val Ala Ser Gly Asn Gly Lys
                325                 330                 335

Gly Gln Ile Phe Val Lys Gly Glu Val Ile Lys Thr Val Pro Glu Ser
            340                 345                 350

Lys Ile Val Glu Thr Leu Ile Glu Glu Ala Met Lys Ile Ala Glu Gln
        355                 360                 365

Met Glu Lys Asp Gly Ile Ala Ser Gly Glu Pro Thr Val Ala Ile Gly
    370                 375                 380

Val
385

<210> SEQ ID NO 32
<211> LENGTH: 336
<212> TYPE: PRT
<213> ORGANISM: Streptomyces clavuligerus

<400> SEQUENCE: 32

Met Leu Ala Ala Pro Arg Gly Tyr Cys Ala Gly Val Asp Arg Ala Val
1               5                   10                  15

Ile Ala Val Glu Lys Ala Leu Glu Gln Tyr Gly Ala Pro Val Tyr Val
            20                  25                  30

Arg His Glu Ile Val His Asn Lys Tyr Val Val Gln Thr Leu Glu Arg
        35                  40                  45

Lys Gly Ala Val Phe Val Asp Lys Thr Ala Glu Val Pro Glu Gly Ser
    50                  55                  60

Ile Val Met Phe Ser Ala His Gly Val Ala Pro Val His Glu Glu
65                  70                  75                  80

Ala Ala Arg Arg Lys Leu Ala Thr Ile Asp Ala Thr Cys Pro Leu Val
                85                  90                  95

Thr Lys Val His Lys Glu Ala Val Arg Phe Ala Asn Glu Asp Tyr Asp
            100                 105                 110

```
Ile Leu Leu Ile Gly His Glu Gly His Glu Val Ile Gly Thr Ser
            115                 120                 125
Gly Glu Ala Pro Asp His Ile Thr Leu Val Asp Gly Pro Asp Asp Val
130                 135                 140
Asp Lys Val Glu Val Arg Asp Glu Ser Lys Val Val Trp Leu Ser Gln
145                 150                 155                 160
Thr Thr Leu Ser Val Asp Glu Thr Met Glu Thr Val Asp Arg Leu Lys
                165                 170                 175
Glu Lys Phe Pro Gln Leu Ile Ser Pro Pro Ser Asp Asp Ile Cys Tyr
                180                 185                 190
Ala Thr Gln Asn Arg Gln Thr Ala Val Lys Gln Met Gly Ala Asp Ala
                195                 200                 205
Asp Leu Val Ile Val Gly Ser Lys Asn Ser Ser Asn Ser Val Arg
210                 215                 220
Leu Val Glu Val Ala Leu Gly Ala Gly Ala Arg Asp Ala His Leu Val
225                 230                 235                 240
Asp Phe Ala Glu Glu Ile Asp Glu Ala Trp Leu Glu Gly Val Ala Thr
                245                 250                 255
Val Gly Leu Thr Ser Gly Ala Ser Val Pro Glu Ile Leu Val Glu Gly
                260                 265                 270
Val Leu Glu Trp Leu Ser Gln Arg Gly Phe Gln Asp Val Glu Leu Val
                275                 280                 285
Lys Ala Ala Glu Glu Ser Ile Thr Phe Ser Leu Pro Lys Glu Leu Arg
                290                 295                 300
Arg Asp Leu Arg Ala Glu Ala Ala Leu Val Glu Arg Ala Glu Ala
305                 310                 315                 320
Val Ala Ala Gly Ser Ala Ser Ala His Pro Gly Ser Ala Ser Gly Ala
                325                 330                 335

<210> SEQ ID NO 33
<211> LENGTH: 331
<212> TYPE: PRT
<213> ORGANISM: Streptomyces roseus

<400> SEQUENCE: 33

Met Thr Ala Ala Ala Pro Val Pro Ala Ser Arg Arg Val Leu Leu Ala
1               5                   10                  15
Ala Pro Arg Gly Tyr Cys Ala Gly Val Asp Arg Ala Val Ile Ala Val
                20                  25                  30
Glu Lys Ala Leu Glu Gln Tyr Gly Ala Pro Val Tyr Val Arg His Glu
            35                  40                  45
Ile Val His Asn Lys Tyr Val Val Gln Thr Leu Glu Arg Lys Gly Ala
50                  55                  60
Ile Phe Val Glu Arg Thr Glu Glu Val Pro Glu Gly Ser Ile Val Met
65                  70                  75                  80
Phe Ser Ala His Gly Val Ala Pro Val Val His Glu Glu Ala Ala Arg
                85                  90                  95
Gly Lys Leu Ala Thr Ile Asp Ala Thr Cys Pro Leu Val Thr Lys Val
                100                 105                 110
His Lys Glu Ala Ile Arg Tyr Ala Asn Glu Asp Phe Asp Ile Leu Leu
            115                 120                 125
Ile Gly His Glu Gly His Glu Glu Val Ile Gly Thr Ser Gly Glu Ala
            130                 135                 140
Pro Asp His Ile Thr Ile Val Asp Gly Pro His Asp Val Glu Lys Val
```

```
145                 150                 155                 160
Thr Val Arg Asp Glu Ser Lys Val Val Trp Leu Ser Gln Thr Thr Leu
                165                 170                 175

Ser Val Asp Glu Thr Met Glu Thr Val Asp Ala Leu Lys Thr Lys Phe
            180                 185                 190

Pro Leu Leu Val Ser Pro Pro Ser Asp Asp Ile Cys Tyr Ala Thr Ser
        195                 200                 205

Asn Arg Gln Ala Ala Val Lys Val Met Gly Ala Asp Ser Asp Leu Val
    210                 215                 220

Ile Val Val Gly Ser Lys Asn Ser Ser Asn Ser Ile Arg Leu Val Glu
225                 230                 235                 240

Val Ala Lys Asp Ala Gly Ala Arg Ala Ala His Leu Val Asp Phe Ala
                245                 250                 255

Ser Glu Ile Asp Glu Ala Trp Leu Glu Gly Val Ser Thr Val Gly Leu
            260                 265                 270

Thr Ser Gly Ala Ser Val Pro Glu Val Leu Val Glu Glu Val Leu Glu
        275                 280                 285

Trp Leu Ala Ala Arg Gly Tyr Ala Asp Val Glu Ile Val Lys Thr Ala
    290                 295                 300

Glu Glu Ser Ile Thr Phe Ser Leu Pro Lys Glu Leu Arg Arg Asp Leu
305                 310                 315                 320

Arg Ala Glu Ala Ala Glu Leu Val Ala Glu Lys
                325                 330

<210> SEQ ID NO 34
<211> LENGTH: 316
<212> TYPE: PRT
<213> ORGANISM: Haliangium ochraceum

<400> SEQUENCE: 34

Met Gln Arg Val Gly Phe Ile Leu Lys Pro Gly Gln Ser Ser Asn Glu
1               5                   10                  15

Arg Leu Leu Thr Glu Leu Ala Thr Trp Val Leu Glu Leu Gly His Leu
            20                  25                  30

Pro Val Ile Ala Ala Glu Asp Arg Pro Val Ile Gln Asn Val Val Ile
        35                  40                  45

Val Pro Arg Glu His Ile Gly Gln Glu Ile Asp Met Ala Val Val Leu
    50                  55                  60

Gly Gly Asp Gly Thr Met Leu Gly Ala Ser Asn Leu Val Ala Asp Gln
65                  70                  75                  80

Gly Val Pro Val Leu Gly Ile Asn Leu Gly Arg Leu Gly Phe Leu Thr
                85                  90                  95

Pro Phe Asp Leu Glu Asp Ala Glu Asp Ala Ile Ala Asp Ala Leu Ala
            100                 105                 110

Gly Lys Leu Arg Thr Ser Glu Arg Met Arg Leu Ala Val Thr Tyr Thr
        115                 120                 125

Ser Asp Gly Glu Ala Pro Val Thr Arg Thr Gly Leu Asn Asp Ala Val
    130                 135                 140

Ile His Gln Gly Ala Met Ala Arg Leu Ile Glu Val Glu Ala Gln Leu
145                 150                 155                 160

Asp Gly Asp Met Val Ser Leu Tyr Arg Ala Asp Gly Leu Ile Ile Ala
                165                 170                 175

Thr Pro Thr Gly Ser Thr Ala Tyr Asn Leu Ala Ala Gly Gly Pro Ile
            180                 185                 190
```

```
Ile Glu Pro Gly Gln Arg Ala Met Val Leu Thr Pro Val Cys Pro His
            195                 200                 205

Ser Leu Thr Asn Arg Ser Leu Val Val Pro Gly Ser Ser Ile Thr
    210                 215                 220

Ile His Leu Asp Arg Ser Ala Arg Gly Val Val Leu Thr Val Asp Gly
225                 230                 235                 240

Gln Trp Ala His Ser Phe Ser Pro Asp Asp Glu Ile Glu Ile Ala Ala
                245                 250                 255

Ala Ala Arg Pro Leu Val Val Phe Lys Ser Asp Lys Arg Tyr Phe Asp
            260                 265                 270

Ile Leu Arg Glu Lys Leu His Trp Gly Ala Arg Leu Asp Arg Ser His
            275                 280                 285

Glu Gln Ile Asp Glu Ala Val Gly Arg Arg Ser Gly Arg Ile Ser Thr
            290                 295                 300

Arg Gln Asp Ala Val Ser Asp Pro Asp Asp Asp
305                 310                 315

<210> SEQ ID NO 35
<211> LENGTH: 334
<212> TYPE: PRT
<213> ORGANISM: Haliangium ochraceum

<400> SEQUENCE: 35

Met Ala Gln Leu Ser Val Ile Gly Ala Gly Ser Tyr Gly Thr Ser Leu
1               5                   10                  15

Ala Leu Val Phe Ala Lys Ala Gly His Ser Val Ser Met Trp Cys His
            20                  25                  30

Glu Ala Glu Leu Ala Glu Arg Met Gln Arg Thr Arg Glu Asn Asp Ile
        35                  40                  45

Tyr Leu Pro Gly Phe Ala Leu Pro Pro Gly Ile Ser Val Ser Ser Glu
    50                  55                  60

Leu Ala Glu Val Val Asp Gly Ala Asp Ile Val Leu Gly Val Thr Pro
65                  70                  75                  80

Thr His Ala Val Arg Lys Val Leu Gly Glu Ala Ala Gly His Leu Ser
                85                  90                  95

Gly Ser Ala Ile Val Val Asn Cys Ser Lys Gly Leu Glu Glu Gly Thr
            100                 105                 110

Leu Gly Arg Val Asp Glu Ile Tyr Arg Asp Ile Leu Pro Pro His Val
        115                 120                 125

Tyr Glu Arg Ala Val Tyr Leu Ser Gly Pro Thr Phe Ala Lys Glu Leu
    130                 135                 140

Ala Ala Gly Leu Pro Ala Ala Leu Val Val Ala Ser Arg Asp Ala Asp
145                 150                 155                 160

Ser Ala Ala Ser Val Gln His Ala Leu Ser Thr Asp Arg Leu Arg Leu
                165                 170                 175

Tyr Thr Ala Pro Asp Val Val Gly Val Leu Ile Gly Gly Ala Leu Lys
            180                 185                 190

Asn Val Val Ala Ile Ala Ala Gly Met Ser Asp Gly Met Gly Leu Gly
        195                 200                 205

Leu Asn Ala Arg Ala Ala Ile Ile Thr Arg Gly Leu Ala Glu Leu Thr
    210                 215                 220

Arg Leu Gly Thr His Val Gly Ala Asp Pro Leu Thr Phe Ala Gly Leu
225                 230                 235                 240

Ser Gly Met Gly Asp Leu Val Leu Thr Cys Ser Gly Asp Leu Ser Arg
                245                 250                 255
```

Asn Arg Gln Val Gly Leu Ala Leu Gly Ala Gly Lys Lys Arg Ala Glu
            260                 265                 270

Ile Val Ala Glu Met Arg Met Val Ala Glu Gly Val Asn Thr Thr Arg
        275                 280                 285

Val Ala Arg Ala Leu Ala Glu Arg Leu Gly Val Glu Ala Pro Ile Thr
    290                 295                 300

Glu Val Met His Arg Val Leu Phe Glu Asp Leu Pro Ala Ser Ala Ala
305                 310                 315                 320

Leu Ala Asp Leu Thr Gly Arg Ala Leu Arg Ser Glu Arg Ala
                325                 330

<210> SEQ ID NO 36
<211> LENGTH: 204
<212> TYPE: PRT
<213> ORGANISM: Deltaproteobacteria bacterium

<400> SEQUENCE: 36

Met Pro Asn Asp Leu Arg His Ile Gly Asn Gly Asp Ser Ala Pro Ser
1               5                   10                  15

Glu Ala Leu Gly Val Ile Glu Leu Gly Thr Ile Ile Arg Gly Tyr Arg
            20                  25                  30

Val Leu Asp Ala Met Val Lys Arg Ser Pro Ile Thr Val Arg Ala Ala
        35                  40                  45

Tyr Pro Val Ser Thr Gly Lys Phe Leu Ile Phe Val Glu Gly Gly Val
    50                  55                  60

Ala Glu Val Asp Glu Ala Met Gln Ala Gly Arg Pro Ala Ala Gly Asn
65                  70                  75                  80

Gln Leu Leu Ala Asp Leu Phe Leu Pro Tyr Cys His Pro Gln Leu Trp
                85                  90                  95

Asp Gly Leu Phe Gln Lys Phe Lys Arg Thr Pro Ile Asp Ala Leu Gly
            100                 105                 110

Leu Phe Glu Cys His Thr Val Val Asp Ala Ile Leu Gly Ala Asp Val
        115                 120                 125

Ala Leu Lys Ala Ala Glu Val Asn Leu Ala Ala Leu His Leu Ala Ala
    130                 135                 140

Gly Ile Gly Gly Arg Ala Tyr Phe Val Val Ser Gly Glu Leu Phe Asp
145                 150                 155                 160

Ala Glu Ala Ala Ile Glu Ala Ala Leu Asp Arg Ile Asp Glu Pro Arg
                165                 170                 175

Ile Ile Glu His Asp Val Leu Cys Ala Pro His Asp Asp Met Thr Leu
            180                 185                 190

Glu Leu Leu Gly Leu Gln Thr Val His Glu Lys Tyr
        195                 200

<210> SEQ ID NO 37
<211> LENGTH: 188
<212> TYPE: PRT
<213> ORGANISM: Hyalangium minutum

<400> SEQUENCE: 37

Met Ser Asp Pro Leu Pro Leu Pro Gly Pro Ala Leu Ala Leu Leu Glu
1               5                   10                  15

Leu Asp Ser Ile Ala Arg Gly Tyr Val Val Ala Asp Ala Val Val Lys
            20                  25                  30

Arg Ala Pro Val Thr Leu Ala Met Ala Glu Ala Val Thr Pro Gly Lys
        35                  40                  45

-continued

```
Tyr Leu Leu Leu Phe Ser Gly Gly Val Ala Glu Val Gln Glu Ser Phe
     50              55              60

Gln Glu Gly Leu Glu Val Ala Gly Arg Thr Leu Leu Asp Lys Leu Leu
 65              70              75                      80

Leu Pro Met Ala Ala Asp Gly Leu Val Ala Gly Leu Gln Gly Arg Phe
             85              90                      95

Pro Gly Thr Phe Gly Glu Ser Val Gly Ile Val Glu Thr His Thr Val
             100             105             110

Ala Ala Ala Leu Leu Cys Ala Asp Thr Ala Leu Lys Arg Ala Glu Val
         115             120             125

Val Leu Glu Arg Leu Gln Leu Ala Arg Gly Ile Gly Gly Lys Gly Val
     130             135             140

Phe Val Leu Ala Gly Glu Leu His Met Val Glu Ala Ala Leu Glu Gly
145             150             155                     160

Ala Ala Ala Ala Val Glu Pro His Leu Leu Leu Thr Thr Glu Ile Ile
             165             170             175

Gln Arg Pro Ser Pro Glu Leu Arg Gly Arg Val Leu
             180             185
```